US011472824B2

United States Patent
Cai et al.

(10) Patent No.: US 11,472,824 B2
(45) **Date of Patent: *Oct. 18, 2022**

(54) PROCESSES FOR PREPARING PHOSPHORODIAMIDATE MORPHOLINO OLIGOMERS

(71) Applicant: SAREPTA THERAPEUTICS, INC., Cambridge, MA (US)

(72) Inventors: Baozhong Cai, Cambridge, MA (US); Mitchell Martini, Cambridge, MA (US); Katie Thomas, Cambridge, MA (US); Ross Shimabuku, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 724 days.

This patent is subject to a terminal disclaimer.

(21) Appl. No.: 16/302,529

(22) PCT Filed: Jun. 30, 2017

(86) PCT No.: PCT/US2017/040318

§ 371 (c)(1),
(2) Date: Nov. 16, 2018

(87) PCT Pub. No.: WO2017/205880

PCT Pub. Date: Nov. 30, 2017

(65) Prior Publication Data

US 2019/0292208 A1 Sep. 26, 2019

Related U.S. Application Data

(60) Provisional application No. 62/357,134, filed on Jun. 30, 2016, provisional application No. 62/357,166, filed on Jun. 30, 2016, provisional application No. 62/508,256, filed on May 18, 2017, provisional application No. 62/341,049, filed on May 24, 2016, provisional application No. 62/340,053, filed on May 24, 2016.

(51) Int. Cl.

| | |
|---|---|
| ***C12N 15/11*** | (2006.01) |
| ***C07F 9/6533*** | (2006.01) |
| ***C07F 9/6512*** | (2006.01) |
| ***C07F 9/6561*** | (2006.01) |
| ***C12N 15/113*** | (2010.01) |
| ***C07F 9/6558*** | (2006.01) |

(52) U.S. Cl.

CPC .......... *C07F 9/6533* (2013.01); *C07F 9/6512* (2013.01); *C07F 9/65583* (2013.01); *C07F 9/65616* (2013.01); *C12N 15/113* (2013.01); *C12N 2310/11* (2013.01); *C12N 2310/314* (2013.01); *C12N 2310/3233* (2013.01); *C12N 2310/51* (2013.01)

(58) Field of Classification Search

CPC .......... C12N 15/111; C12N 2310/3233; A61K 31/7088; A61K 31/7125

See application file for complete search history.

(56) References Cited

U.S. PATENT DOCUMENTS

| | | | |
|---|---|---|---|
| 5,034,506 | A | 7/1991 | Summerton et al. |
| 5,142,047 | A | 8/1992 | Summerton et al. |
| 5,166,315 | A | 11/1992 | Summerton et al. |
| 5,185,444 | A | 2/1993 | Summerton et al. |
| 5,217,866 | A | 6/1993 | Summerton et al. |
| 5,506,337 | A | 4/1996 | Summerton et al. |
| 5,521,063 | A | 5/1996 | Summerton et al. |
| 5,698,685 | A | 12/1997 | Summerton et al. |
| 6,355,640 | B1 | 3/2002 | Akahane et al. |
| 6,670,461 | B1 | 12/2003 | Wengel et al. |
| 6,794,499 | B2 | 9/2004 | Wengel et al. |
| 7,034,133 | B2 | 4/2006 | Wengel et al. |
| 7,053,207 | B2 | 5/2006 | Wengel |
| 7,060,809 | B2 | 6/2006 | Wengel et al. |
| 7,084,125 | B2 | 8/2006 | Wengel |
| 7,569,575 | B2 | 8/2009 | Sorensen et al. |
| 7,572,582 | B2 | 8/2009 | Wengel et al. |
| 7,807,816 | B2 | 10/2010 | Wilton et al. |
| 7,960,541 | B2 | 6/2011 | Wilton et al. |
| 8,067,571 | B2 | 11/2011 | Weller et al. |
| 8,076,476 | B2 | 12/2011 | Reeves et al. |
| 8,232,384 | B2 | 7/2012 | Wilton et al. |
| 8,299,206 | B2 | 10/2012 | Fox et al. |
| 8,450,474 | B2 | 5/2013 | Wilton et al. |
| 8,455,634 | B2 | 6/2013 | Wilton et al. |

(Continued)

FOREIGN PATENT DOCUMENTS

| | | | |
|---|---|---|---|
| WO | WO 1990/02749 | A1 | 3/1990 |
| WO | WO-2004043977 | A2 | 5/2004 |

(Continued)

OTHER PUBLICATIONS

Alul, R.H., et al., "Oxalyl-CPG: A Labile Support for Synthesis of Sensitive Oligonucleotide Derivatives," *Nucleic Acids Research*, 19(7): 1527-1532, Oxford University Press, England (1991).

(Continued)

*Primary Examiner* — Dana H Shin

(74) *Attorney, Agent, or Firm* — Sterne, Kessler, Goldstein & Fox P.L.L.C.

(57) ABSTRACT

Provided herein are processes for preparing an oligomer (e.g., a morpholino oligomer). The synthetic processes described herein may be advantageous to scaling up oligomer synthesis while maintaining overall yield and purity of a synthesized oligomer.

13 Claims, 6 Drawing Sheets

Specification includes a Sequence Listing.

(56) References Cited

U.S. PATENT DOCUMENTS

| | | | |
|---|---|---|---|
| 8,455,635 | B2 | 6/2013 | Wilton et al. |
| 8,455,636 | B2 | 6/2013 | Wilton et al. |
| 8,476,423 | B2 | 7/2013 | Wilton et al. |
| 8,486,907 | B2 | 7/2013 | Wilton et al. |
| 8,524,880 | B2 | 9/2013 | Wilton et al. |
| 8,637,483 | B2 | 1/2014 | Wilton et al. |
| 8,865,883 | B2 | 10/2014 | Sazani et al. |
| 8,871,918 | B2 | 10/2014 | Sazani et al. |
| 8,969,551 | B2 | 3/2015 | Ueda |
| 9,018,368 | B2 | 4/2015 | Wilton et al. |
| 9,024,007 | B2 | 5/2015 | Wilton et al. |
| 9,035,040 | B2 | 5/2015 | Wilton et al. |
| 9,175,286 | B2 | 11/2015 | Wilton et al. |
| 9,228,187 | B2 | 1/2016 | Wilton et al. |
| 9,234,198 | B1 | 1/2016 | Sazani et al. |
| 9,249,416 | B2 | 2/2016 | Wilton et al. |
| 9,416,361 | B2 | 8/2016 | Iversen et al. |
| 9,422,555 | B2 | 8/2016 | Wilton et al. |
| 9,434,948 | B2 | 9/2016 | Sazani et al. |
| 9,441,229 | B2 | 9/2016 | Wilton et al. |
| 9,447,415 | B2 | 9/2016 | Wilton et al. |
| 9,447,416 | B2 | 9/2016 | Sazani et al. |
| 9,447,417 | B2 | 9/2016 | Sazani et al. |
| 9,453,225 | B2 | 9/2016 | Sazani et al. |
| 9,506,058 | B2 | 11/2016 | Kaye |
| 9,605,262 | B2 | 3/2017 | Wilton et al. |
| 9,758,783 | B2 | 9/2017 | Wilton et al. |
| 9,944,926 | B2 | 4/2018 | Linsley et al. |
| 9,994,851 | B2 | 6/2018 | Wilton et al. |
| 10,227,590 | B2 | 3/2019 | Wilton et al. |
| 10,266,827 | B2 | 4/2019 | Wilton et al. |
| 10,287,586 | B2 | 5/2019 | Wilson et al. |
| 10,337,003 | B2 | 7/2019 | Kaye |
| 10,364,431 | B2 | 7/2019 | Kaye |
| 10,421,966 | B2 | 9/2019 | Wilton et al. |
| RE47,691 | E | 11/2019 | Wilton et al. |
| RE47,751 | E | 12/2019 | Wilton et al. |
| RE47,769 | E | 12/2019 | Wilton et al. |
| 10,875,880 | B2 | 12/2020 | Cai et al. |
| 2008/0227742 | A1 | 9/2008 | Dmochowski et al. |
| 2010/0292458 | A1 | 11/2010 | Bühler et al. |
| 2011/0263686 | A1 | 10/2011 | Wilton et al. |
| 2013/0211062 | A1 | 8/2013 | Watanabe et al. |
| 2014/0256926 | A1 | 9/2014 | Damha et al. |
| 2014/0330006 | A1 | 11/2014 | Hanson et al. |
| 2015/0197786 | A1 | 7/2015 | Osborn et al. |
| 2016/0076033 | A1 | 3/2016 | Torii et al. |
| 2018/0163205 | A1 | 6/2018 | Wilton et al. |
| 2018/0271993 | A1 | 9/2018 | Passini et al. |
| 2019/0127738 | A1 | 5/2019 | Sazani et al. |
| 2019/0270994 | A1 | 9/2019 | Wilton et al. |
| 2019/0276480 | A1 | 9/2019 | Cai et al. |
| 2019/0323010 | A1 | 10/2019 | Wilton et al. |
| 2019/0359982 | A1 | 11/2019 | Kaye |
| 2020/0040337 | A1 | 2/2020 | Kaye |
| 2020/0080079 | A1 | 3/2020 | Cai et al. |

FOREIGN PATENT DOCUMENTS

| | | | |
|---|---|---|---|
| WO | WO-2006000057 | A1 | 1/2006 |
| WO | WO 2009/064471 | A1 | 5/2009 |
| WO | WO-2010115993 | A1 | 10/2010 |
| WO | WO-2011150408 | A2 | 12/2011 |
| WO | WO 2012/043730 | A1 | 4/2012 |
| WO | WO-2013053928 | A1 | 4/2013 |
| WO | WO 2013/082551 | A1 | 6/2013 |
| WO | WO-2014153240 | A2 | 9/2014 |
| WO | WO-2017205496 | A1 | 11/2017 |
| WO | WO-2017205513 | A1 | 11/2017 |
| WO | WO-2017205880 | A1 | 11/2017 |

OTHER PUBLICATIONS

Atherton, E., et al., "Polyamide supports for polypeptide synthesis," *J Am. Chem. Soc.*, 97(22):6584-6585, American Chemical Society, United States (1975).

Atherton, E., et al., "The polyamide method of solid phase peptide and oligonucleotide synthesis," *Bioorg. Chem.*, 8(3): 351-370, Elsevier, Netherlands (1979).

Atherton, E., et al., "Peptide synthesis. Part 2. Procedures for solid-phase synthesis using $N^{\alpha}$-fluorenylmethoxycarbonylamonio-acids on polyamide supports. Synthesis of substance P and of acyl carrier protein 65-74 decapeptide," *J. Chem. Soc., Perkin Trans.* 1, 0: 538-546, Royal Society of Chemistry, United Kingdom (1981).

Bayer, E., et al., "A new support for polypeptide synthesis in columns," *Tetrahedron Letters*, 11(51): 4503-4505. Elsevier, Netherlands (1970).

Berg, R.H., et al., "Long-chain polystyrene-grafted polyethylene film matrix: a new support for solid-phase peptide synthesis," *J Am. Chem. Soc.*, 111(20): 8024-8026, American Chemical Society, United States (1989).

Bonora, G.M., et al., "A Liquid-Phase Process Suitable for Large-Scale Synthesis of Phosphorothioate Oligonucleotides," *Organic Process Research & Development*, 4(3): 225-231, American Chemical Society, United States (2000).

Cirak, S., et al., "Exon skipping and dystrophin restoration in patients with Duchenne muscular dystrophy after systemic phosphorodiamidate morpholino oligomer treatment: an open-label, phase 2, dose-escalation study," *Lancet*, 378: 595-605, Elsevier, Netherlands (2011).

Daniels, S.B., et al., "Membranes as solid supports for peptide synthesis," *Tetrahedron Letters*, 30(33): 4345-4348, Elsevier, Netherlands (1989).

Eliel, E.L., and Wilen, S.H., (Eds.), "Chirality in Molecules Devoid of Chiral Center," Chapter 14 in *Stereochemistry of Carbon Compounds*, pp. 1119-1190, John Wiley & Sons, New York, (1994).

Geysen, H.M., et al., "Use of peptide synthesis to probe viral antigens for epitopes to a resolution of a single amino acid," *Proc. Natl. Acad Sci. USA*, 81: 3998-4002, National Academy of Sciences, United States (1984).

Goemans, N.M., et al., "Systemic Administration of PRO051 in Duchenne's Muscular Dystrophy," *N. Engl. J. Med.*, 364(16): 1513-1522, Massachusetts Medical Society, United States (2011).

Gravert, D.J., and Janda, K.D., Organic Synthesis on Soluble Polymeer Supports: Liquid-Phase Methodologies, *Chem. Rev.*, 97(2): 489-510, American Chemical Society, United States (1997).

Houghten, R.A., "General method for the rapid solid-phase synthesis of large numbers of peptides: specificity of antigen-antibody interaction at the level of individual amino acids," *Proc. Natl. Acad Sci. USA*, 82(15): 5131-5135, National Academy of Science, United States (1985).

International Search Report and Written Opinion for International Application No. PCT/US2017/040318, United States Patent and Trademark Office, United States, dated Sep. 26, 2017, 10 pages.

Johnsson, R., et al., "New Light Labile Linker for Solid Phase Synthesis of 2'-O-Acetalester Oligonucleotides and Applications to Sirna Prodrug Development," *Bioorganic & Medicinal Chemistry Letters*, 21(12): 3721-3725, Elsevier, Netherlands (2011).

Kent, S.B.H. and Merrifield, R.B., "Preparation anf Properties of tert-Butyloxycarbonylaminoacyl-4-(oxymethyl) phenlyacetamidomethyl-(Kel F-g-styrene) Resin, an Insoluble, Noncrosslinked Support for Solid Phase Peptide Synthesis," *Israel J Chem.*, 17(4): 243-247, John Wiley & Sons, Inc., United States (1978).

Kinali, M., et al., "Local restoration of dystrophin expression with the morpholino oligomer AVI-4658 in Duchenne muscular dystrophy: a single-blind, placebo-controlled, dose-escalation, proof-of-concept study," The Lancet, 8(10): P918-928, Elsevier, Netherlands (2009).

March, J, (Ed.) "Stereochemistry," Chapter 4 in *Advanced Organic Chemistry*, Third Edition, John Wiley & Sons, United State (1985).

Parr, W., and Grohmann, D.K., "Solid-Phase Peptide Synthesis on an Inorganic Matrix having Oiganic Groups on the Surface," *Angew. Chem. Internal.*, 11(4): 314-315, John Wiley & Sons, Inc., United States (1972).

(56) References Cited

OTHER PUBLICATIONS

Scott, R.P.W., et al., "The Use of Resin Coated Glass Beads in the Form of a Packed Bed for the Solid Phase Synthesis of Peptides," *J Chrom. Sci.*, 9(10): 577-591, Oxford University Press, England (1971).
Summerton, J., and Weller, D., "Morpholino Antisense Oligomers: Design, Preparation, and Properties," *Antisense and Nucleic Acid Drug Development*, 7(3):187-195, Mary Ann Liebert, United States (1997).
Van Deutekom, J.C., et al., "Local Dystophin Restoration with Antisense Oligonucleotide PRO051," N. Engl. J. Med., 357: 2677-2686, Massachusetts Medical Society, United Stated (2007).
Van Rietschoten, et al., "Simultaneous Synthesis of Two Peptide Analogs on Different Insoluble Supports" in *Peptides*, pp. 113-116, Y. Wolman, Ed., Wiley and Sons, United States (1974).
Wright, P., et al., "Large Scale Synthesis of Oligonucleotides via Phosphoramidite Nucleosides and a High-Loaded Polystyrene Support," *Tetrahedron Letters*, 34(21): 3373-3376, Elsevier, Netherlands (1993).
Office Action dated Feb. 6, 2020, in U.S. Appl. No. 16/302,018, Cai, B., et al., filed Nov. 15, 2018, 15 pages.
International Preliminary Report on Patentability for Application No. PCT/US2017/034284, WIPO, Switzerland, dated Nov. 27, 2018, 6 pages.
International Search Report and Written opinion for International Application No. PCT/US2017/034284, European Patent Office, Netherlands, dated Jul. 27, 2017, 9 pages.
International Search Report and Written Opinion for International Application No. PCT/US2017/034235, European Patent Office, Netherlands, dated Jul. 31, 2017, 9 pages.
International Preliminary Report on Patentability for International Application No. PCT/US2017/034235, WIPO, Switzerland, dated Nov. 27, 2018, 6 pages.
Notice of Allowance dated Apr. 29, 2020, in U.S. Appl. No. 16/303,356, Cai, B. et al., filed Nov. 20, 2018.
Singh, Sanjay K., et al., "LNA (locked nucleic acids): synthesis and high-affinity nucleic acid recognition," Chemical communications 4: 455-456, Royal Society of Chemistry, United Kingdom (1998).
Koshkin, Alexei A, et al., "LNA (Locked Nucleic Acids): Synthesis of the adenine, cytosine, guanine, 5-methylcytosine, thymine and uracil bicyclonucleoside monomers, oligomerisation, and unprecedented nucleic acid recognition," Tetrahedron 54(14): 3607-3630, Elsevier, United Kingdom (1998).
Wengel, Jesper, "Synthesis of 3'-C- and 4'-C-branched oligodeoxynucleoiides and the development of locked nucleic acid (LNA)," Accounts of Chemical Research 32: 301-310, American Chemical Society, United States (1999).
Obika, S., et al., "Synthesis of 2'-0, 4'-C-methyleneuridine and-cytidine. Novel bicyclic nucleosides having a fixed C3,-endo sugar puckering," Tetrahedron Letters 38 (50): 8735-8738, Elsevier, United Kingdom (1997).
Obika, Satoshi, et al., "Stability and structural features of the duplexes containing nucleoside analogues with a fixed N-type conformation, 2'-O, 4'-C-methyleneribonucleosides," Tetrahedron Letters 39:5401-5404, Elsevier, United Kingdom (1998).
Obika, Satoshi, et al., "Synthesis and properties of 3'-amino-2',4'-BNA, a bridged nucleic acid with a N3'→ P5' phosphoramidate linkage," Bioorganic & Medicinal Chemistry 16: 9230-9237, Elsevier, United Kingdom (2008).
Iyer, R. P., et al., "The automated synthesis of sulfur-containing oligodeoxyribonucleotides using 3H-1,2-benzodithiol-3-one 1,1-dioxide as a sulfur-transfer reagent," The Journal of Organic Chemistry 55: 4693-4699, American Chemical Society, United States (1990).
Yoo, B.,et al., "2'-O-methyl-modified phosphorothioate antisense oligonucleotides have reduced non-specific effects in vitro," Nucleic Acids Research 32:2008-2016, Oxford University Press, United States (2004).
Martin, Pierre, "New Access to 2'-O-alkylated Oligoribonucleotides," Helvetica Chimica Acta 78(2): 486-504, John Wiley & Sons, Switzerland(1995).
Yamada, T., et al., "Synthesis of 2'-O-[2-(N-methylcarbamoyl) ethyl] ribonucleosides using oxa-Michael reaction and chemical and biological properties of nucleotide derivatives incorporating these modified ribonucleosides," The Journal of Organic Chemistry 76:3042-3053, American Chemical Society, United States (2011).
Office Action dated Apr. 28, 2020, in U.S. Appl. No. 16/302,443, Cai, B. et al., filed Nov. 16, 2018.
Restriction Requirement dated Jan. 27, 2020, in U.S. Appl. No. 16/302,443, Cai, B. et al., filed Nov. 16, 2018, 9 pages.
International Search Report and Written opinion for International Application No. PCT/US2017/040311, International Search Authority, United States, dated Dec. 8, 2017, 10 pages.
International Preliminary Report on Patentability for Application No. PCT/US2017/040311, International Search Authority, United States, dated Nov. 27, 2018, 10 pages.
Virta, Pasi, et al., "Solid-supported synthesis of oligomeric bioconjugates," Tetrahedron 59(28): 5137-5174, Pergamon, England (2003).

PROCESSES FOR PREPARING PHOSPHORODIAMIDATE MORPHOLINO OLIGOMERS

RELATED APPLICATIONS

This patent application claims the benefit of U.S. Provisional Patent Application Ser. No. 62/508,256, filed May 18, 2017, U.S. Provisional Patent Application Ser. No. 62/341,049, filed May 24, 2016, U.S. Provisional Patent Application Ser. No. 62/340,953, filed May 24, 2016, U.S. Provisional Patent Application Ser. No. 62/357,134, filed Jun. 30, 2016, and U.S. Provisional Patent Application Ser. No. 62/357,166, filed Jun. 30, 2016. The entire contents of the above-referenced provisional patent applications are incorporated herein by reference.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing or translation through any one of a number of antisense mechanisms. The sequence specificity of antisense compounds makes them attractive as tools for target validation and gene functionalization, as well as therapeutics to selectively modulate the expression of genes involved in disease.

Duchenne muscular dystrophy (DMD) is caused by a defect in the expression of the protein dystrophin. The gene encoding the protein contains 79 exons spread out over more than 2 million nucleotides of DNA. Any exonic mutation that changes the reading frame of the exon, or introduces a stop codon, or is characterized by removal of an entire out of frame exon or exons, or duplications of one or more exons, has the potential to disrupt production of functional dystrophin, resulting in DMD.

Recent clinical trials testing the safety and efficacy of splice switching oligonucleotides (SSOs) for the treatment of DMD are based on SSO technology to induce alternative splicing of pre-mRNAs by steric blockade of the spliceosome (Cirak et al., 2011; Goemans et al., 2011; Kinali et al., 2009; van Deutekom et al., 2007). However, despite these successes, the pharmacological options available for treating DMD are limited.

Golodirsen is a phosphorodiamidate morpholino oligomer (PMO) designed to skip exon 53 of the human dystrophin gene in patients with DMD who are amendable to exon 53 skipping to restore the read frame and produce a functional shorter form of the dystrophin protein.

Although significant progress has been made in the field of antisense technology, there remains a need in the art for methods of preparing phosphorodiamidate morpholino oligomers with improved antisense or antigene performance.

SUMMARY

Provided herein are processes for preparing phosphorodiamidate morpholino oligomers (PMOs). The synthetic processes described herein allow for a scaled-up PMO synthesis while maintaining overall yield and purity of a synthesized PMO.

Accordingly, in one aspect, provided herein is a process for preparing an oligomeric compound of Formula (A):

(A)

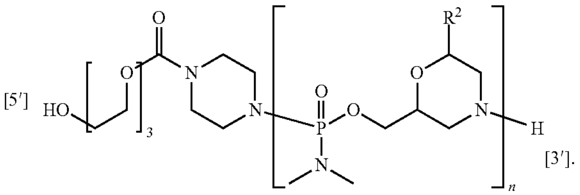

In certain embodiments, provided herein is a process for preparing an oligomeric compound of Formula (G):

(G)

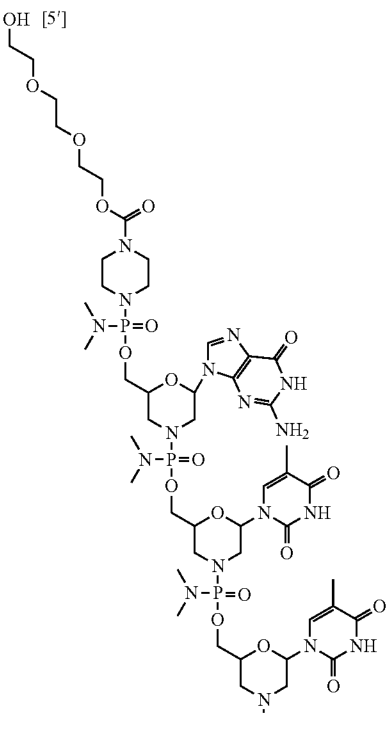

-continued
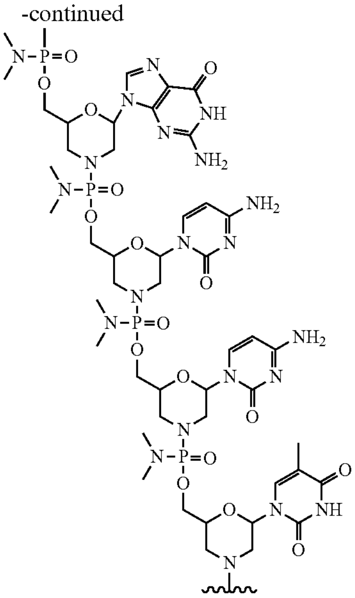
BREAK A
BREAK A
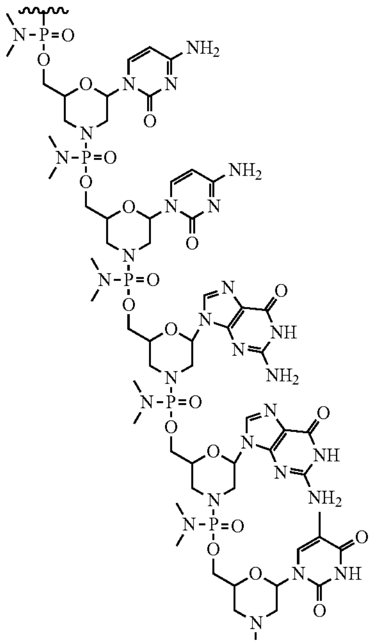
-continued
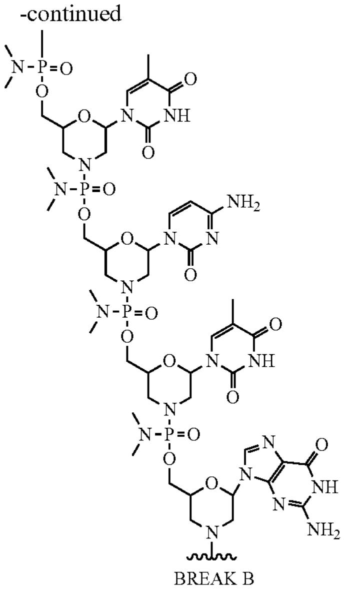
BREAK B
BREAK B
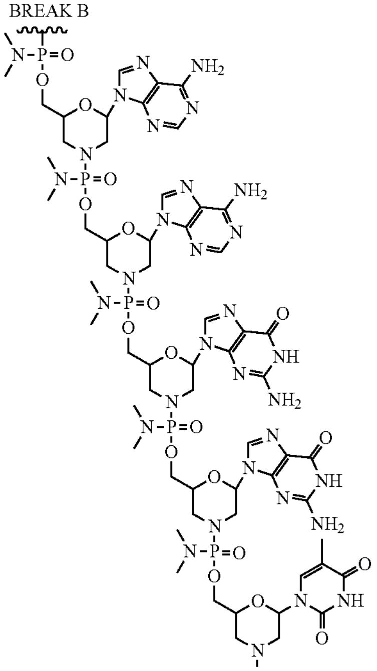

-continued
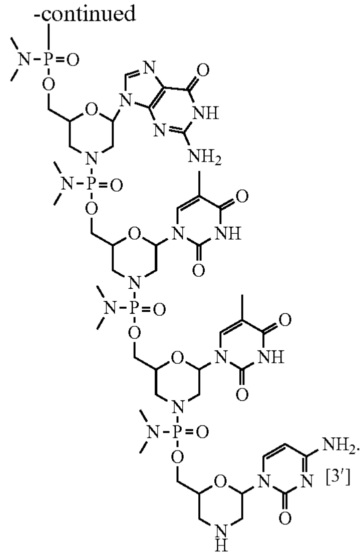
In yet another embodiment, the oligomeric compound of the disclosure including, for example, some embodiments of an oligomeric compound of Formula (G), is an oligomeric compound of Formula (XII):
-continued
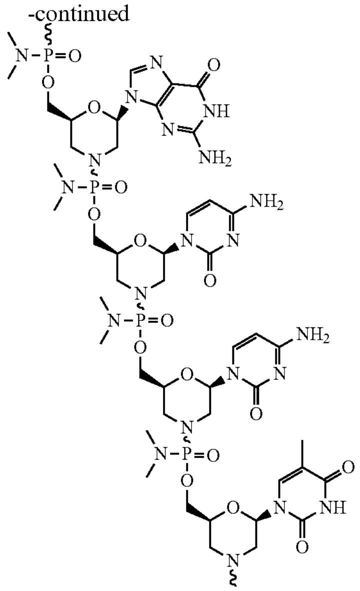
BREAK A
(XII)
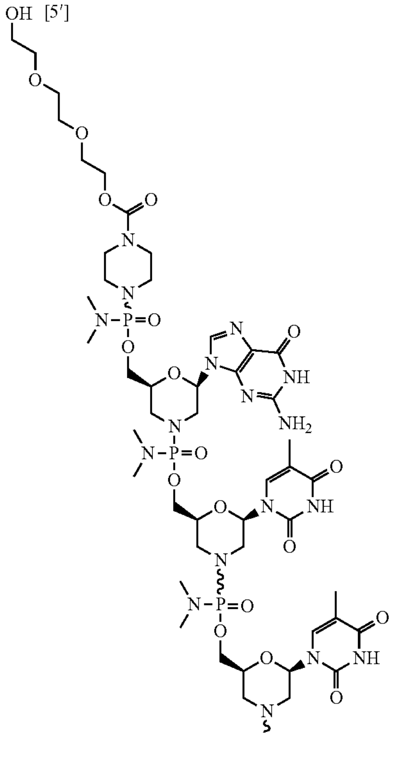
BREAK A
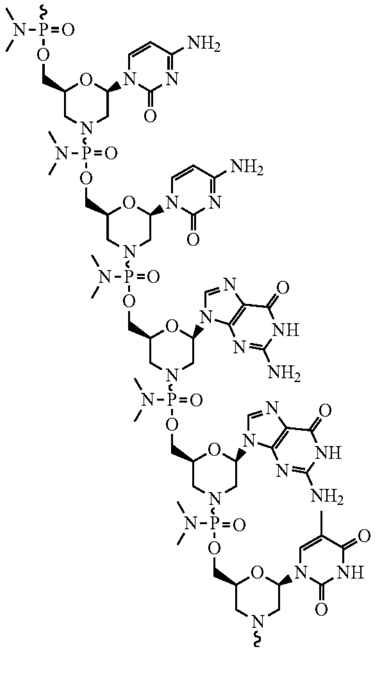

-continued

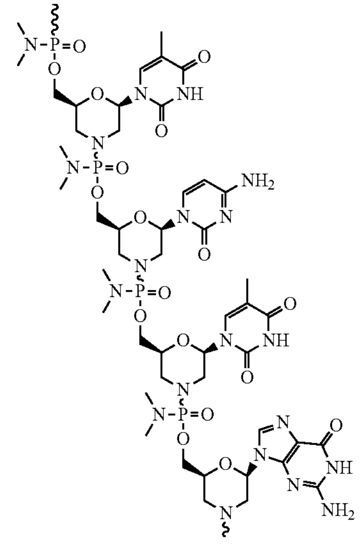

BREAK B

-continued

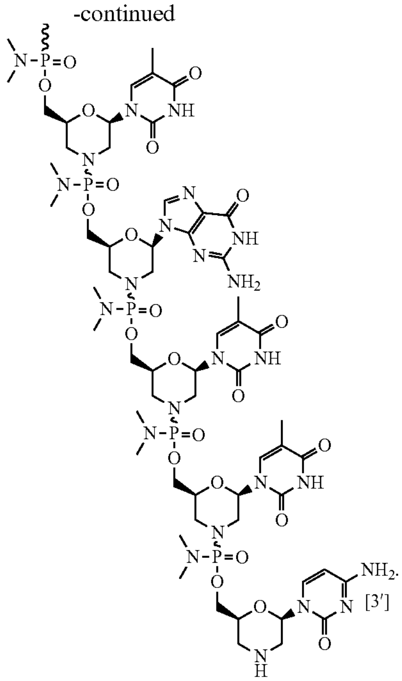

[3']

BREAK B

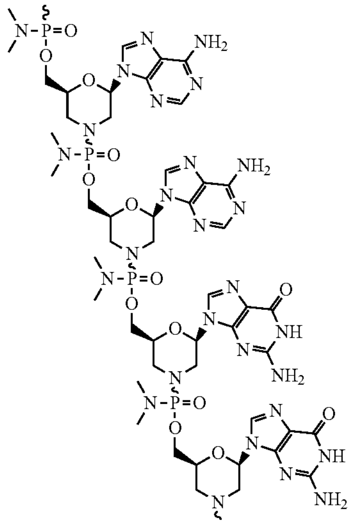

For clarity, the structural formulas including, for example, oligomeric compound of Formula (C) and Golodirsen depicted by Formula (XII), are a continuous structural formula from 5' to 3', and, for the convenience of depicting the entire formula in a compact form in the above structural formulas, Applicants have included various illustration breaks labeled "BREAK A" and "BREAK B." As would be understood by the skilled artisan, for example, each indication of "BREAK A" shows a continuation of the illustration of the structural formula at these points. The skilled artisan understands that the same is true for each instance of "BREAK B" in the structural formulas above including Golodirsen. None of the illustration breaks, however, are intended to indicate, nor would the skilled artisan understand them to mean, an actual discontinuation of the structural formulas above including Golodirsen.

DETAILED DESCRIPTION

Figure 1:
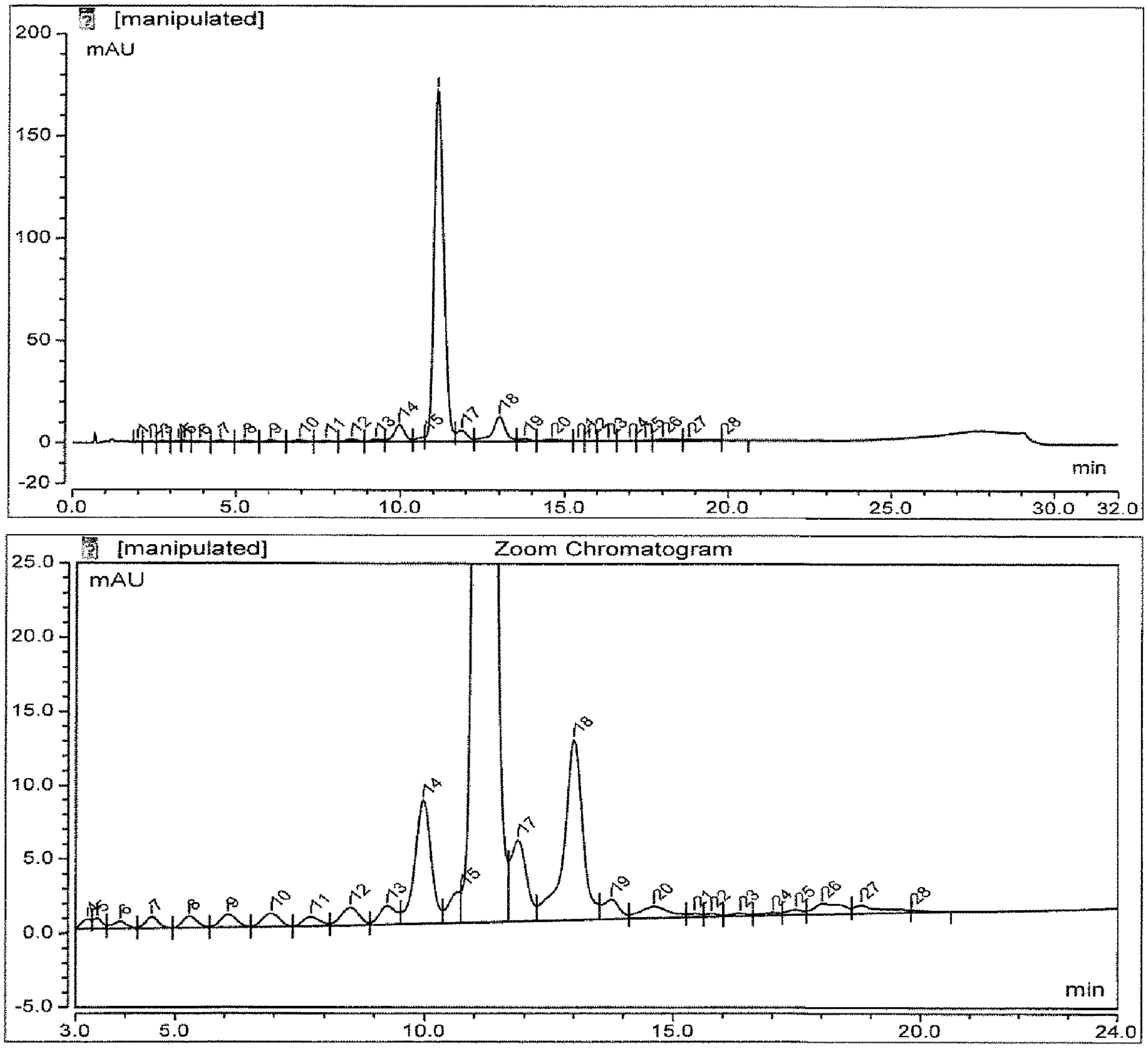
FIG. 1 and FIG. 2 show a representative analytical high performance liquid chromatography (HPLC) chromatogram of a synthesized and deprotected Golodirsen (SRP-4053) crude drug substance (see Example 4).

Provided herein are processes for preparing a morpholino oligomer. The a morpholino oligomer described herein displays stronger affinity for DNA and RNA without compromising sequence selectivity, relative to native or unmodified oligonucleotides. In some embodiments, the morpholino oligomer of the disclosure minimizes or prevents cleavage by RNase H. In some embodiments, the morpholino oligomer of the disclosure does not activate RNase H.

The processes described herein are advantageous in an industrial-scale process and can be applied to preparing quantities of a morpholino oligomer in high yield and scale (e.g., about 1 kg, about 1-10 kg, about 2-10 kg, about 5-20 kg, about 10-20 kg, or about 10-50 kg).

Definitions

Listed below are definitions of various terms used to describe this disclosure. These definitions apply to the terms as they are used throughout this specification and claims, unless otherwise limited in specific instances, either individually or as part of a larger group.

"Base-protected" or "base protection" refers to protection of the base-pairing groups, eg purine or pyrimidine bases, on the morpholino subunits with protecting groups suitable to prevent reaction or interference of the base-pairing groups during stepwise oligomer synthesis. (An example of a base-protected morpholino subunit is the activated C subunit Compound (C) having a CBZ protecting group on the cytosine amino group depicted below.)

An "activated phosphoramidate group" is typically a chlorophosphoramidate group, having substitution at nitrogen which is desired in the eventual phosphorodiamidate linkage in the oligomer. An example is (dimethylamino) chlorophosphoramidate, i.e. —O—P(═O)($NMe_2$)Cl.

The term "support-bound" refers to a chemical entity that is covalently linked to a support-medium.

The term "support-medium" refers to any material including, for example, any particle, bead, or surface, upon which an oligomer can be attached or synthesized upon, or can be modified for attachment or synthesis of an oligomer. Representative substrates include, but are not limited to, inorganic supports and organic supports such as glass and modified or functionalized glass, plastics (including acrylics, polystyrene and copolymers of styrene and other materials, polypropylene, polyethylene, polybutylene, polyurethanes, TEFLON, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. Particularly useful support-medium and solid surfaces for some embodiments are located within a flow cell apparatus. In some embodiments of the processes described herein, the support-medium comprises polystyrene with 1% crosslinked divinylbenzene.

In some embodiments, representative support-medium comprise at least one reactive site for attachment or synthesis of an oligomer. For example, in some embodiments, a support-medium of the disclosure comprises one or more terminal amino or hydroxyl groups capable of forming a chemical bond with an incoming subunit or other activated group for attaching or synthesizing an oligomer.

Some representative support-medium that are amenable to the processes described herein include, but are not limited to, the following: controlled pore glass (CPG); oxalyl-controlled pore glass (see, e.g., Alul, et al., Nucleic Acids Research 1991, 19, 1527); silica-containing particles, such as porous glass beads and silica gel such as that formed by the reaction of trichloro-[3-(4-chloromethyl)phenyl]propylsilane and porous glass beads (see Parr and Grohmann, *Angew. Chem. Internal.* Ed. 1972, 11, 314, sold under the trademark "PORASIL E" by Waters Associates, Framingham, Mass., USA); a mono ester of 1,4-dihydroxymethylbenzene and silica (see Bayer and Jung, *Tetrahedron Lett.,* 1970, 4503, sold under the trademark "BIOPAK" by Waters Associates); TENTAGEL (see, e.g., Wright, et al., Tetrahedron Letters 1993, 34, 3373); cross-linked styrene/divinylbenzene copolymer beaded matrix, or POROS, a copolymer of polystyrene/divinylbenzene (available from Perceptive Biosystems); soluble support-medium such as polyethylene glycol PEG's (see Bonora et al., Organic Process Research & Development, 2000, 4, 225-231); PEPS support, which is a polyethylene (PE) film with pendant long-chain polystyrene (PS) grafts (see Berg, et al., *J. Am. Chem. Soc.,* 1989, 111, 8024 and International Patent Application WO 1990/02749); copolymers of dimethylacrylamide cross-linked with N,N'-bisacryloylethylenediamine, including a known amount of N-tertbutoxycarbonyl-beta-alanyl-N'-acryloylhexamethylenediamine (see Atherton, et al., *J. Am. Chem. Soc.,* 1975, 97, 6584, *Bioorg. Chem.* 1979, 8, 351, and J. C. S. Perkin I 538 (1981)); glass particles coated with a hydrophobic cross-linked styrene polymer (see Scott, et al., *J. Chrom. Sci.,* 1971, 9, 577); fluorinated ethylene polymer onto which has been grafted polystyrene (see Kent and Merrifield, *Israel J. Chem.* 1978, 17, 243 and van Rietschoten in *Peptides* 1974, Y. Wolman, Ed., Wiley and Sons, New York, 1975, pp. 113-116); hydroxypropylacrylate-coated polypropylene membranes (Daniels, et al., *Tetrahedron Lett.* 1989, 4345); acrylic acid-grafted polyethylene-rods (Geysen, et al., *Proc. Natl. Acad. Sci. USA,* 1984, 81, 3998); a "tea bag" containing traditionally-used polymer beads (Houghten, *Proc. Natl. Acad. Sci. USA,* 1985, 82, 5131); and combinations thereof.

The term "flow cell apparatus" refers to a chamber comprising a surface (e.g., solid surface) across which one or more fluid reagents (e.g., liquid or gas) can be flowed.

The term "deblocking agent" refers to a composition (e.g., a solution) comprising a chemical acid or combination of chemical acids for removing protecting groups. Exemplary chemical acids used in deblocking agents include halogenated acids, e.g., chloroacetic acid, dichloroacetic acid, trichloroacetic acid, fluoroacetic acid, difluoroacetic acid, and trifluoroacetic acid. In some embodiments, a deblocking agent removes one or more trityl groups from, for example, an oligomer, a support-bound oligomer, a support-bound subunit, or other protected nitrogen or oxygen moiety.

The terms "halogen" and "halo" refer to an atom selected from the group consisting of fluorine, chlorine, bromine, and iodine.

The term "capping agent" refers to a composition (e.g., a solution) comprising an acid anhydride (e.g., benzoic anhydride, acetic anhydride, phenoxyacetic anhydride, and the like) useful for blocking a reactive cite of, for example, a support-medium forming a chemical bond with an incoming subunit or other activated group.

The term "cleavage agent" refers to a composition (e.g., a liquid solution or gaseous mixture) comprising a chemical base (e.g., ammonia or 1,8-diazabicycloundec-7-ene) or a combination of chemical bases useful for cleaving, for example, a support-bound oligomer from a support-medium.

The term "deprotecting agent" refers to a composition (e.g., a liquid solution or gaseous mixture) comprising a chemical base (e.g., ammonia, 1,8-diazabicycloundec-7-ene or potassium carbonate) or a combination of chemical bases useful for removing protecting groups. For example, a deprotecting agent, in some embodiments, can remove the base protection from, for example, a morpholino subunit, morpholino subunits of a morpholino oligomer, or support-bound versions thereof.

The term "solvent" refers to a component of a solution or mixture in which a solute is dissolved. Solvents may be inorganic or organic (e.g., acetic acid, acetone, acetonitrile, acetyl acetone, 2-aminoethanol, aniline, anisole, benzene, benzonitrile, benzyl alcohol, 1-butanol, 2-butanol, i-butanol, 2-butanone, t-butyl alcohol, carbon disulfide, carbon tetrachloride, chlorobenzene, chloroform, cyclohexane, cyclohexanol, cyclohexanone, di-n-butylphthalate, 1,1-dichloroethane, 1,2-dichloroethane, diethylamine, diethylene glycol, diglyme, dimethoxyethane (glyme), N,N-dimethylaniline, dimethylformamide, dimethylphthalate, dimethylsulfoxide, dioxane, ethanol, ether, ethyl acetate, ethyl acetoacetate, ethyl benzoate, ethylene glycol, glycerin, heptane, 1-heptanol, hexane, 1-hexanol, methanol, methyl acetate, methyl t-butyl ether, methylene chloride, 1-octanol, pentane, 1-pentanol, 2-pentanol, 3-pentanol, 2-pentanone, 3-pentanone, 1-propanol, 2-propanol, pyridine, tetrahydrofuran, toluene, water, p-xylene).

The phrases "morpholino oligomer" and "phosphorodiamidate morpholino oligomer" or "PMO" refers to an oligomer having morpholino subunits linked together by phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The term "EG3 tail" refers to triethylene glycol moieties conjugated to the oligomer, e.g., at its 3'- or 5'-end. For example, in some embodiments, "EG3 tail" conjugated to the 3' end of an oligomer can be of the structure:

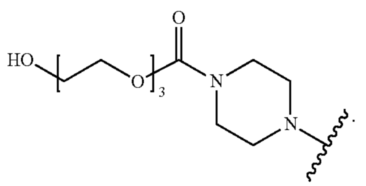

The terms "about" or "approximately" are generally understood by persons knowledgeable in the relevant subject area, but in certain circumstances can mean within ±10%, or within ±5%, of a given value or range.

Processes for Preparing Morpholino Oligomers

Synthesis is generally prepared, as described herein, on a support-medium. In general a first synthon (e.g. a monomer, such as a morpholino subunit) is first attached to a support-medium, and the oligomer is then synthesized by sequentially coupling subunits to the support-bound synthon. This iterative elongation eventually results in a final oligomeric compound. Suitable support-media can be soluble or insoluble, or may possess variable solubility in different solvents to allow the growing support-bound polymer to be either in or out of solution as desired. Traditional support-media are for the most part insoluble and are routinely placed in reaction vessels while reagents and solvents react with and/or wash the growing chain until the oligomer has reached the target length, after which it is cleaved from the support, and, if necessary, further worked up to produce the final polymeric compound. More recent approaches have introduced soluble supports including soluble polymer supports to allow precipitating and dissolving the iteratively synthesized product at desired points in the synthesis (Gravert et al., Chem. Rev., 1997, 97,489-510).

Provided herein are processes for preparing morpholino oligomers).

Thus, in one aspect, provided herein is a process for preparing a compound of Formula (II):

(II)

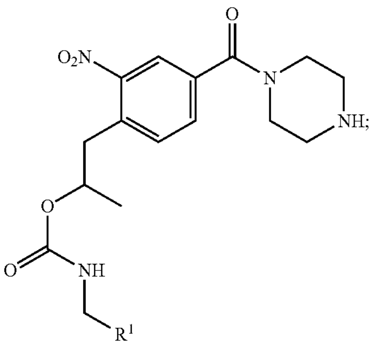

wherein $R^1$ is a support-medium;

wherein the process comprises contacting a compound of Formula (A1):

(A1)

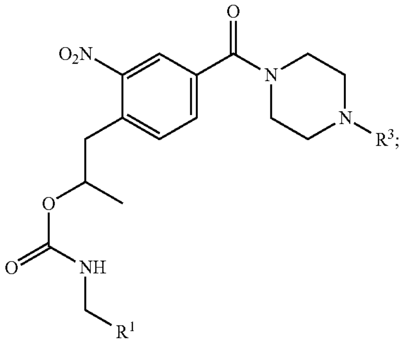

wherein $R^1$ is a support-medium and $R^3$ is selected from the group consisting of trityl, monomethoxytrityl, dimethoxytrityl and trimethoxytrityl;

with a deblocking agent to form the compound of Formula (II).

In another aspect, provided herein is a process for preparing a compound of Formula (A3):

(A3)

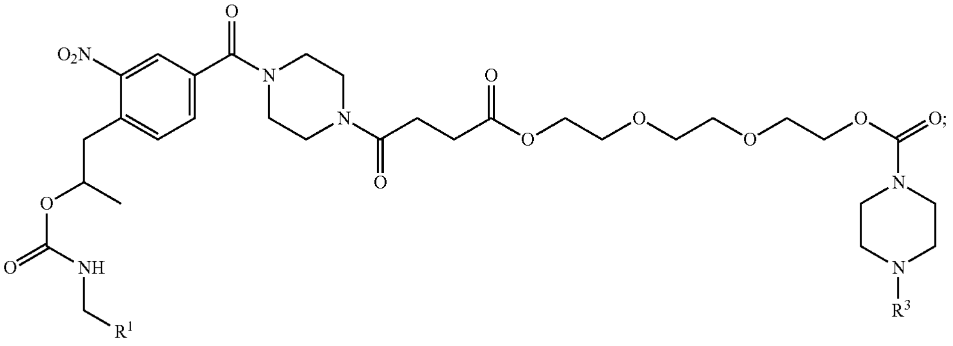

wherein $R^1$ is a support-medium, and $R^3$ is selected from the group consisting of trityl, monomethoxytrityl, dimethoxytrityl and trimethoxytrityl;
wherein the process comprises contacting a compound of Formula (II):

(II)

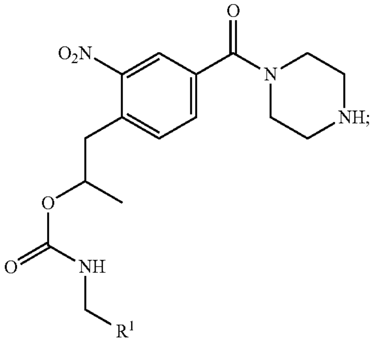

wherein $R^1$ is a support-medium;
with a compound of Formula (A2):

(A2)

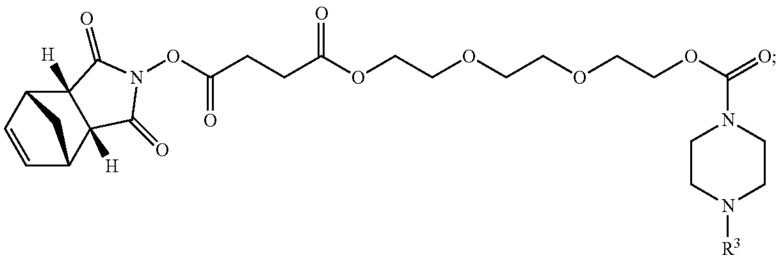

wherein $R^3$ is selected from the group consisting of trityl, monomethoxytrityl, dimethoxytrityl and trimethoxytrityl;

to form the compound of Formula (A3).

In still another aspect, provided herein is a process for preparing a compound of Formula (IV):

(IV)

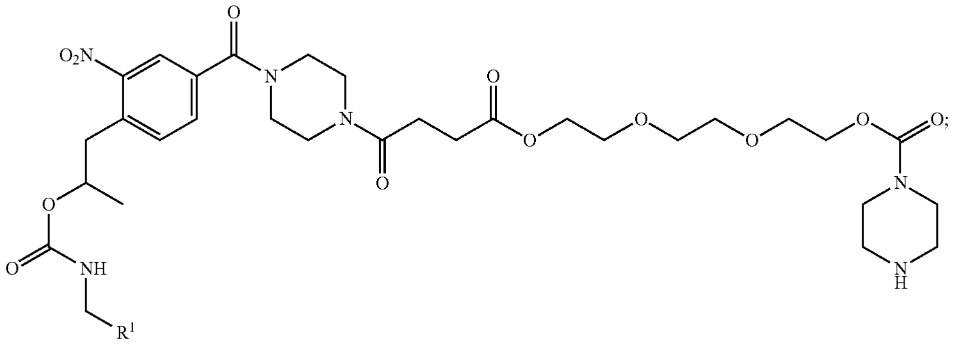

wherein $R^1$ is a support-medium;

wherein the process comprises contacting a compound of Formula (A3):

(A3)

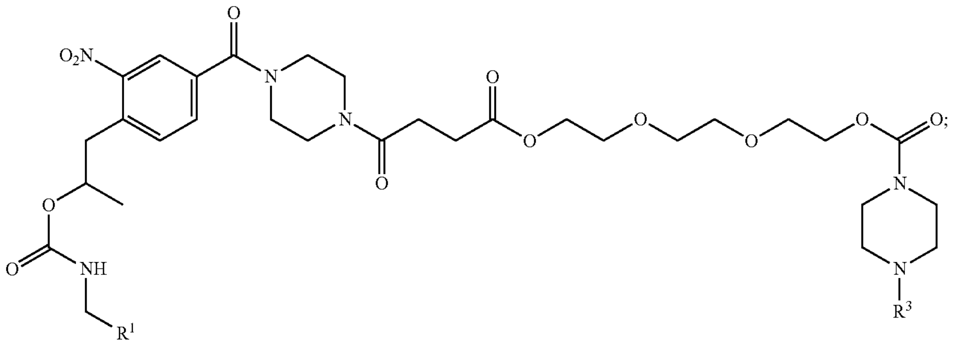

wherein $R^1$ is a support-medium, and $R^3$ is selected from the group consisting of trityl, monomethoxytrityl, dimethoxytrityl and trimethoxytrityl;

with a deblocking agent to form a compound of Formula (IV).

In yet another aspect, provided herein is a process for preparing a compound of Formula (A5):

(A5)

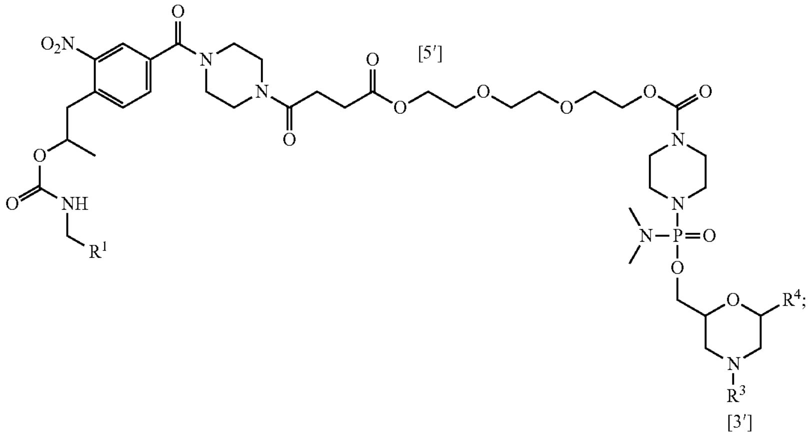

wherein $R^1$ is a support-medium, $R^3$ is selected from the group consisting of trityl, monomethoxytrityl, dimethoxytrityl and trimethoxytrityl, and
$R^4$ is selected from the group consisting of:
(PC)
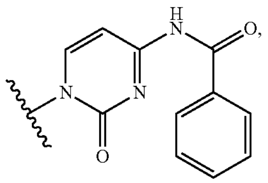
(DPG)
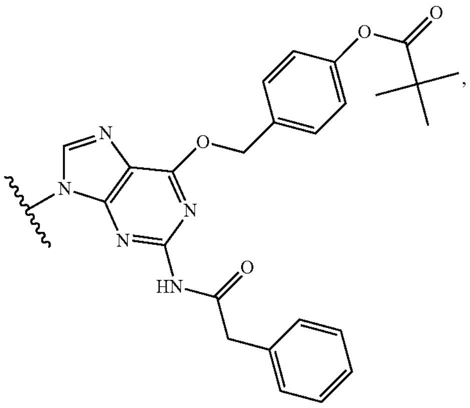
(T)
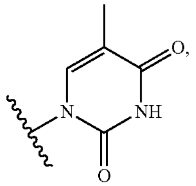
(PA)
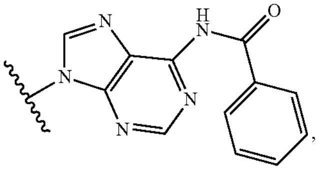
-continued
(P5mC)
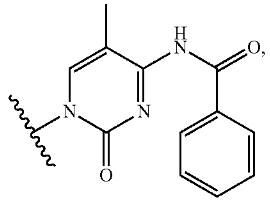
(U)
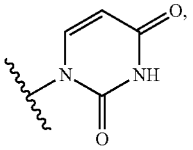
(I)
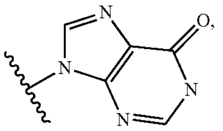 and
(PG)
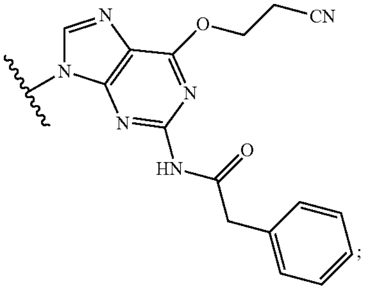
wherein the process comprises contacting a compound of Formula (IV):
(IV)
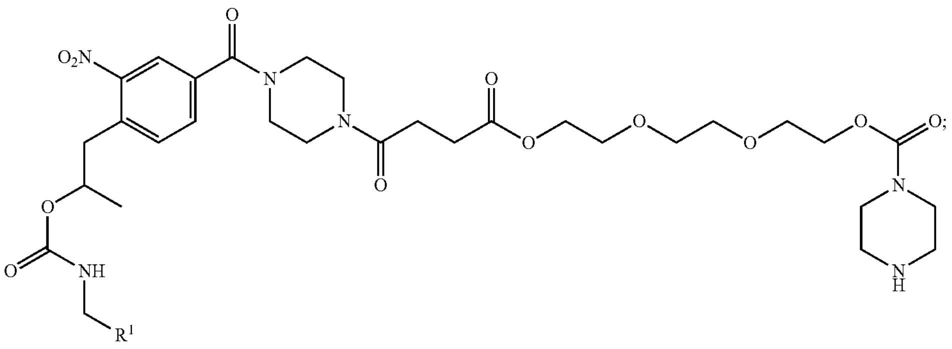

wherein $R^1$ is a support-medium;
with a compound of Formula (A4):
(A4)
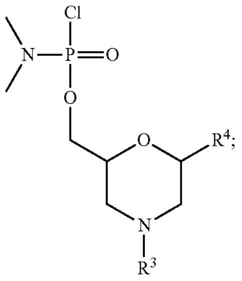
wherein $R^3$ is selected from the group consisting of trityl, monomethoxytrityl, dimethoxytrityl and trimethoxytrityl, and $R^4$ is selected from the group consisting of:
(PC)
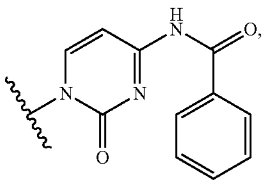
(DPG)
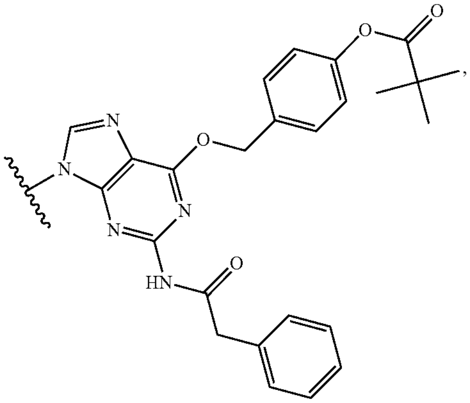
(T)
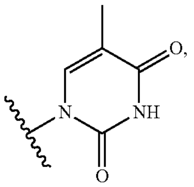
-continued
(PA)
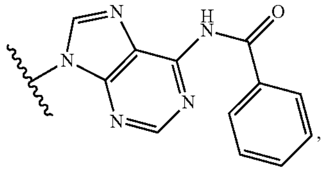
(P5mC)
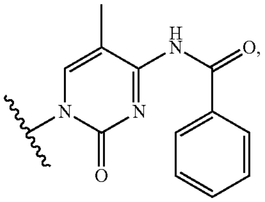
(U)
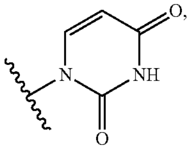
(I)
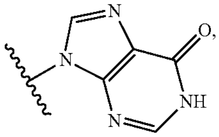
and
(PG)
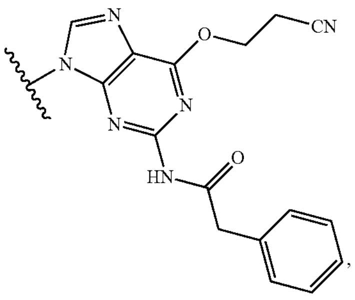
to form a compound of Formula (A5).

In another aspect, provided herein is a process for preparing a compound of Formula (A9):

(A9)

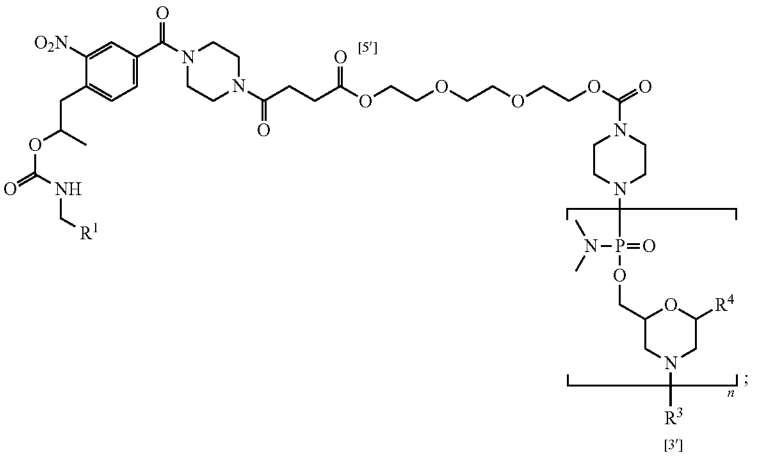

wherein n is an integer from 10 to 40, $R^1$ is a support-medium, $R^3$ is selected from the group consisting of trityl, monomethoxytrityl, dimethoxytrityl and trimethoxytrityl, and $R^4$ is, independently for each occurrence, selected from the group consisting of:

(PC)

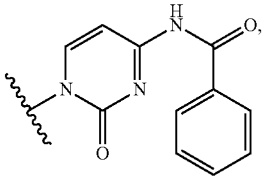

(DPG)

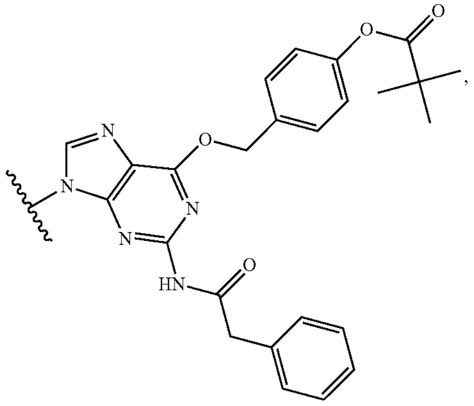

(T)

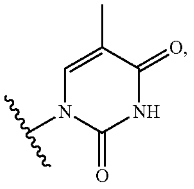

-continued (PA)

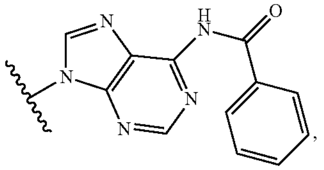

(P5mC)

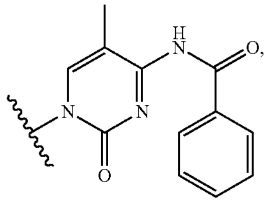

(U)

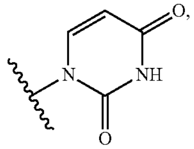

(I)

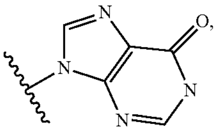

and (PG)

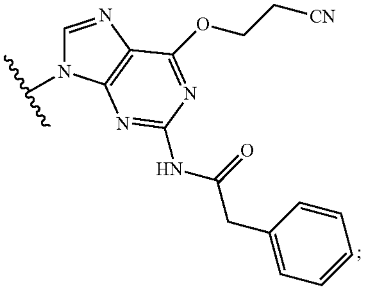

and wherein the process comprises the sequential steps of:

(a) contacting a compound of Formula (IV):

(IV)

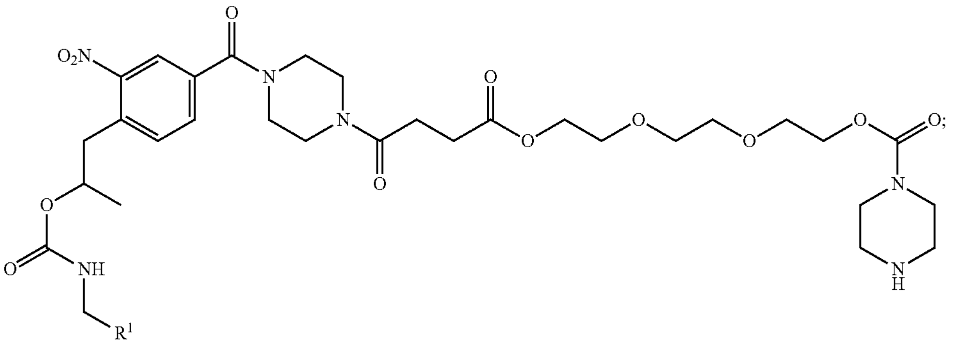

wherein $R^1$ is a support-medium;

with a compound of Formula (A4):

(A4)

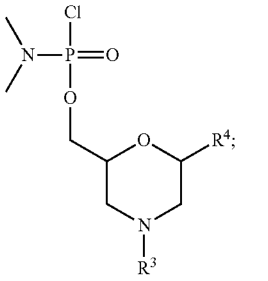

wherein $R^3$ is selected from the group consisting of trityl, monomethoxytrityl, dimethoxytrityl and trimethoxytrityl, and $R^4$ is selected from the group consisting of:

(PC)

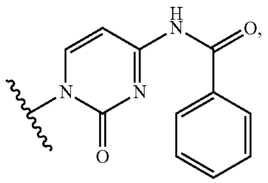

(DPG)

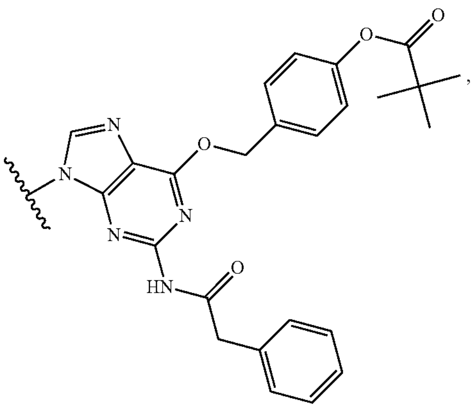

-continued (T)

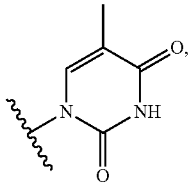

(PA)

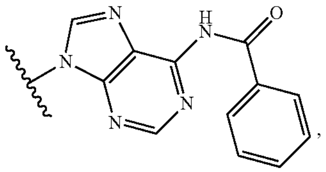

(P5mC)

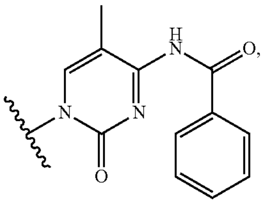

(U)

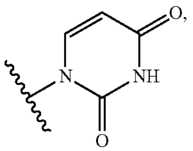

(I)

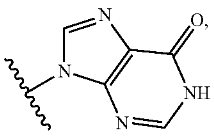

and

-continued
(PG)
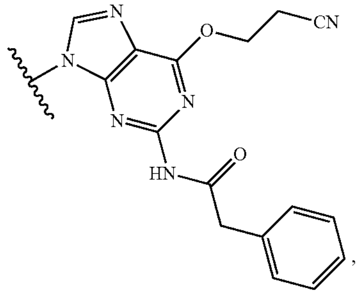
to form a compound of Formula (A5):
(A5)
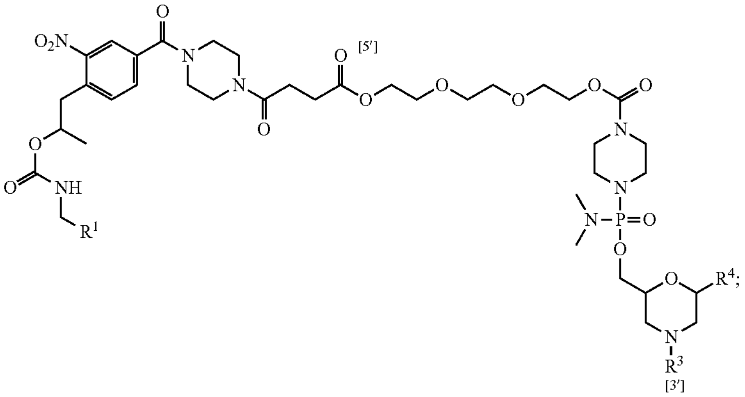
wherein $R^1$ is a support-medium, $R^3$ is selected from the group consisting of trityl, monomethoxytrityl, dimethoxytrityl and trimethoxytrityl, and
$R^4$ is selected from the group consisting of:
(PC)
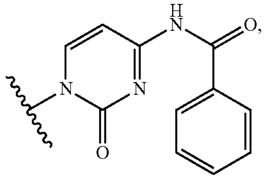
(DPG)
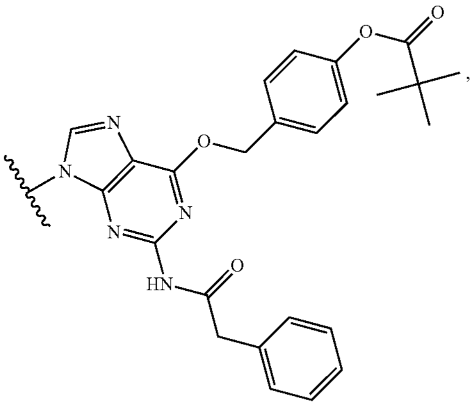
-continued
(T)
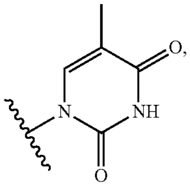
(PA)
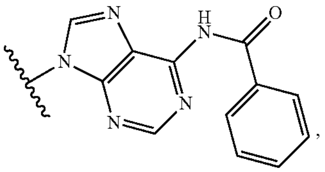
(P5mC)
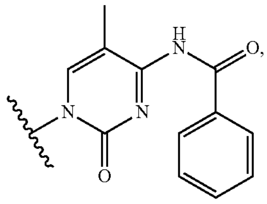
(U)
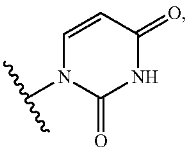

-continued (I)

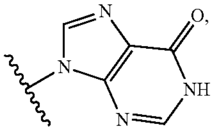

and (PG)

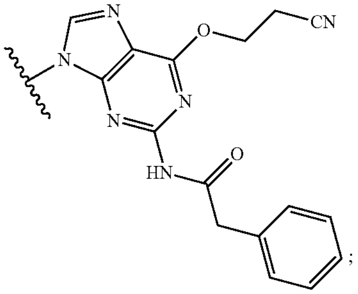

and (b) performing n−1 iterations of the sequential steps of:

(b1) contacting the product formed by the immediately prior step with a deblocking agent; and (b2) contacting the compound formed by the immediately prior step with a compound of Formula (A8):

(A8)

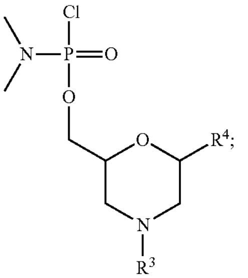

wherein $R^3$ is selected from the group consisting of trityl, monomethoxytrityl, dimethoxytrityl and trimethoxytrityl, and $R^4$ is selected from the group consisting of:

(PC)

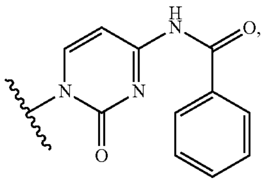

-continued (DPG)

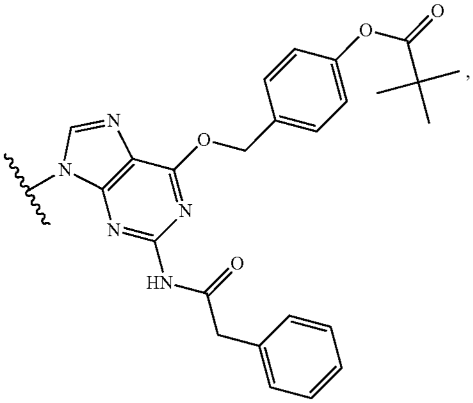

(T)

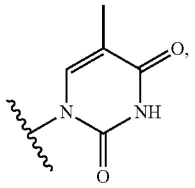

(PA)

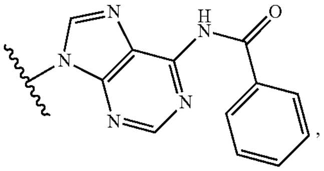

(P5mC)

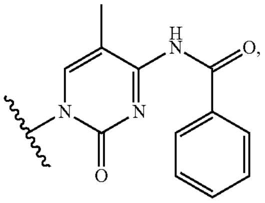

(U)

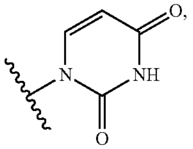

(I)

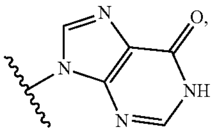

and (PG)

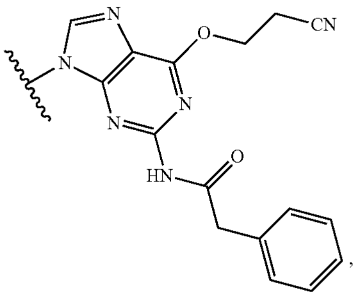

to form a compound of Formula (A9).

In yet another aspect, provided herein is a process for preparing a compound of Formula (A10):
(A10)
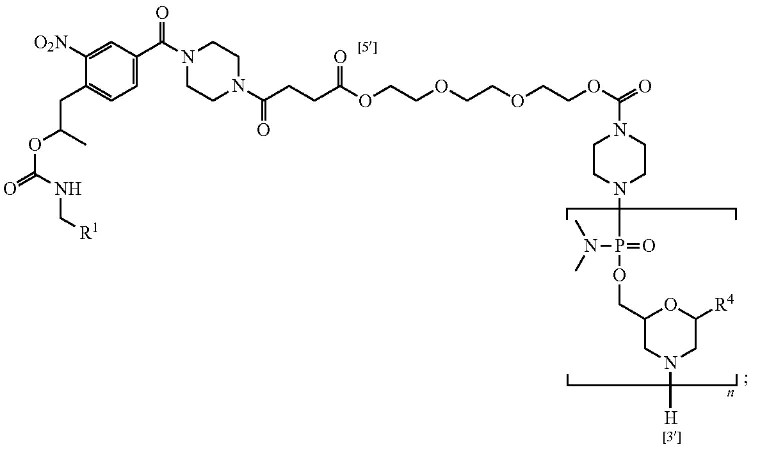
wherein n is an integer from 10 to 40, $R^1$ is a support-medium, and $R^4$ is,
independently for each occurrence, selected from the group consisting of:
(PC)
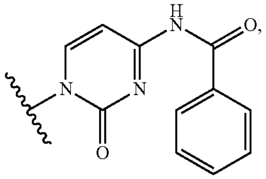
(DPG)
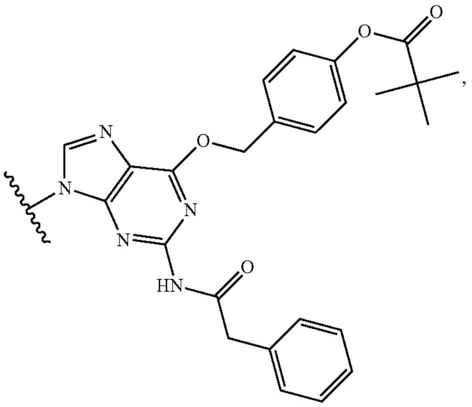
(T)
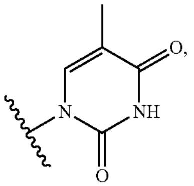
-continued
(PA)
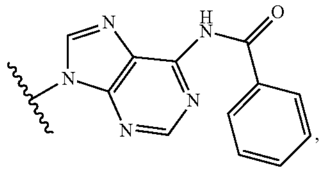
(P5mC)
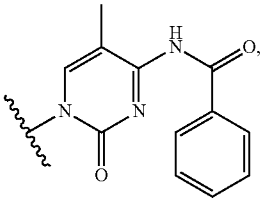
(U)
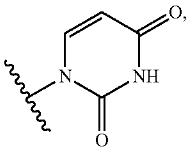
(I)
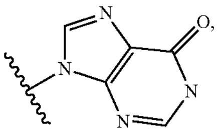
and
(PG)
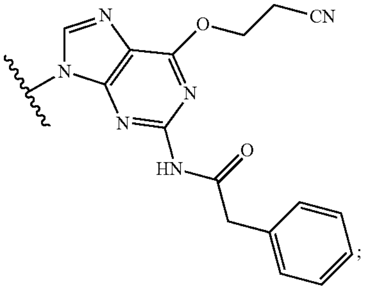

wherein the process comprises contacting a compound of Formula (A9):
(A9)
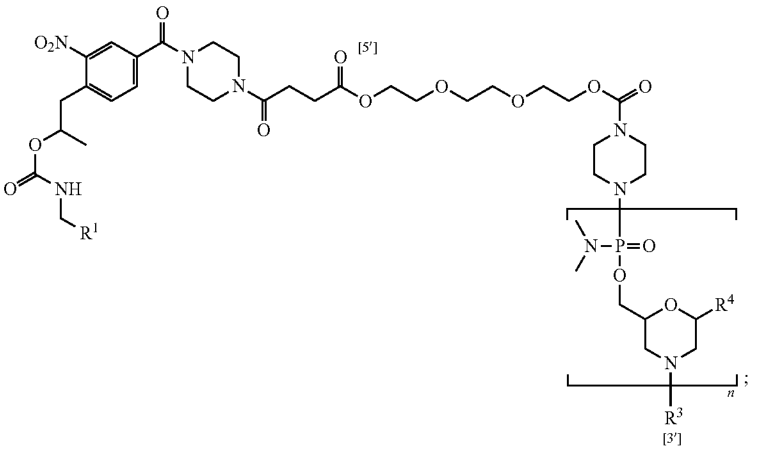
wherein n is an integer from 10 to 40, $R^1$ is a support-medium, $R^3$ is selected from the group consisting of trityl, monomethoxytrityl, dimethoxytrityl and trimethoxytrityl, and $R^4$ is,
independently for each occurrence, selected from the group consisting of:
(PC)
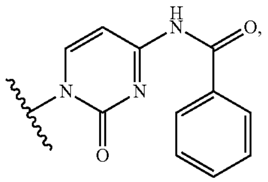
(DPG)
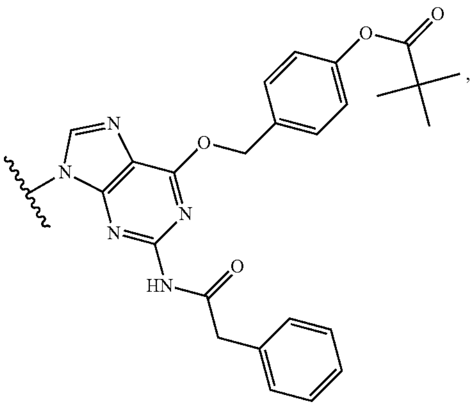
(T)
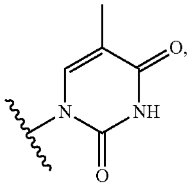
-continued
(PA)
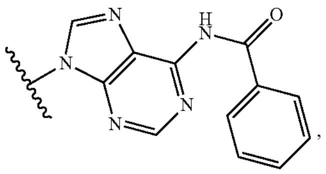
(P5mC)
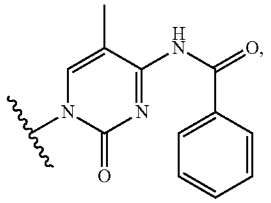
(U)
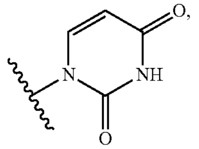
(I)
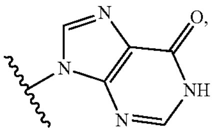
and
(PG)
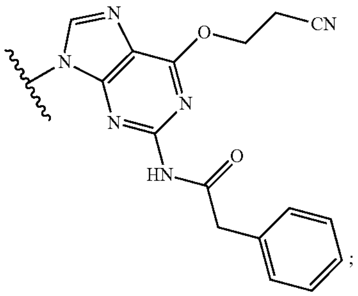

and
with a deblocking agent to form a compound of Formula (A10).
In still another aspect, provided herein is a process for preparing a compound of Formula (A11):
(A11)
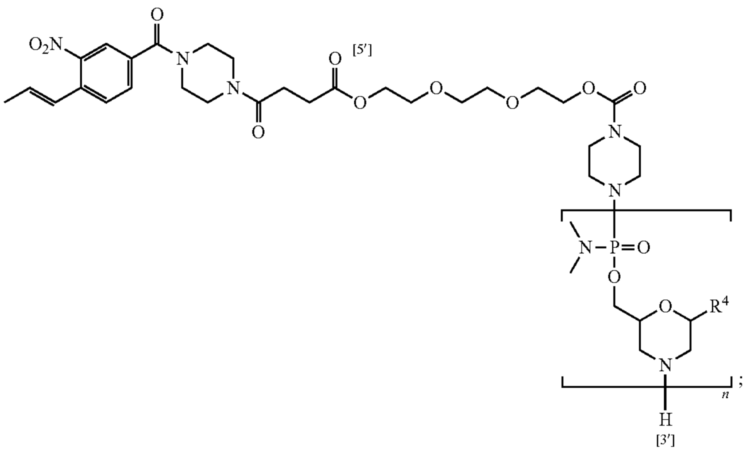
wherein n is an integer from 10 to 40, and $R^4$ is, for each occurrence independently selected from the group consisting of:
(PC)
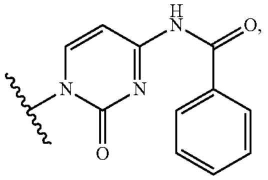
(DPG)
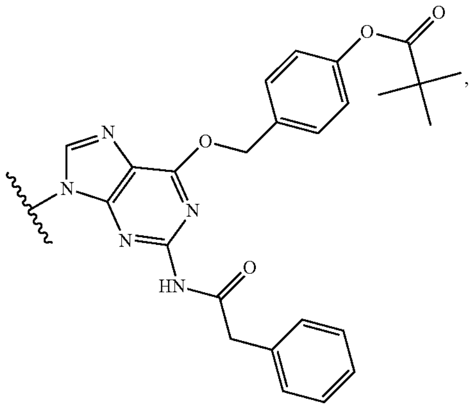
(T)
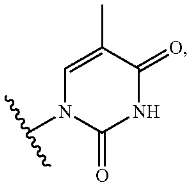
-continued
(PA)
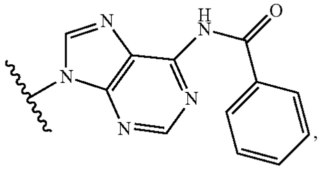
(P5mC)
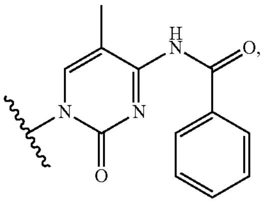
(U)
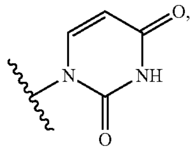
(I)
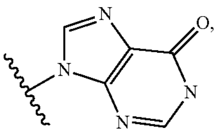
and
(PG)
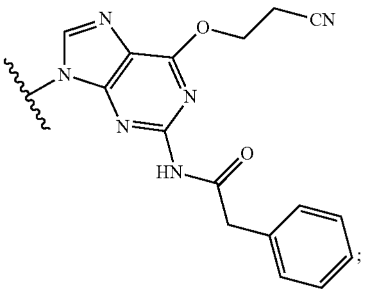

and
wherein the process comprises contacting the compound of Formula (A10):
(A10)
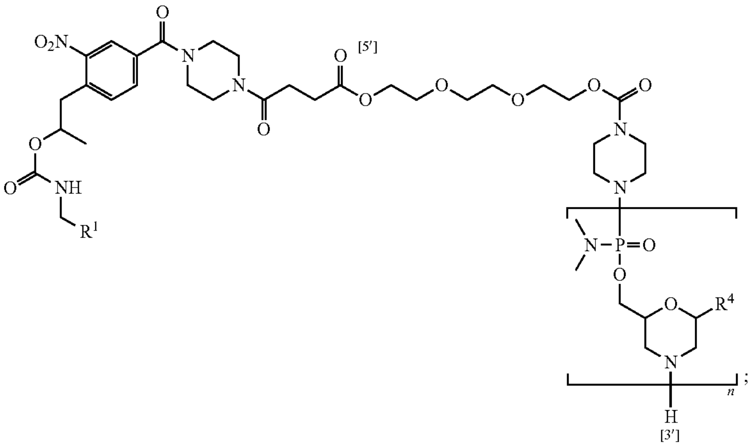
wherein n is an integer from 10 to 40, $R^1$ is a support-medium, and $R^4$ is,
independently for each occurrence, selected from the group consisting of:
(PC)
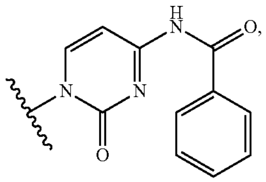
(DPG)
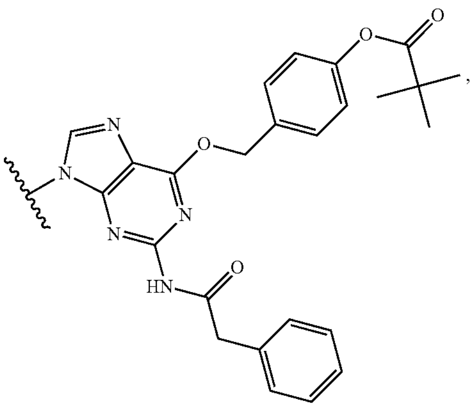
(T)
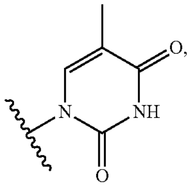
-continued
(PA)
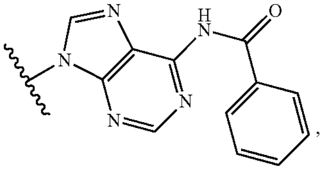
(P5mC)
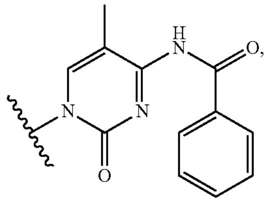
(U)
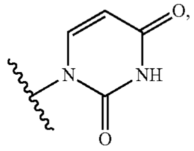
(I)
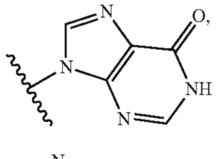
and
(PG)
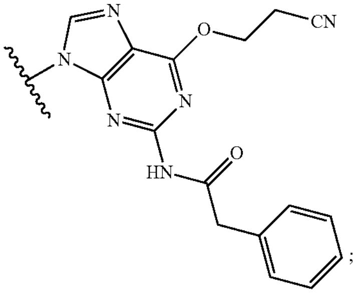
with a cleaving agent to form a compound of Formula (A11).

In another aspect, provided herein is a process for preparing an oligomeric compound of Formula (A):
(A)
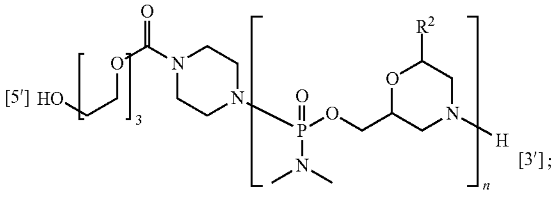
wherein n is an integer from 10 to 40, and each $R^2$ is, independently for each occurrence, selected from the group consisting of:
(C)
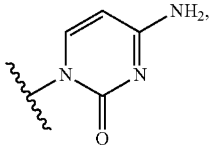
(G)
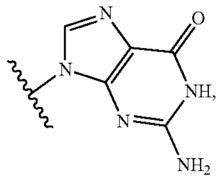
(T)
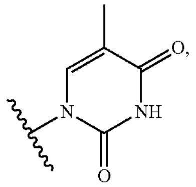
-continued
(A)
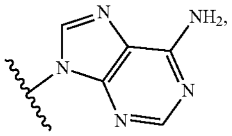
(5mC)
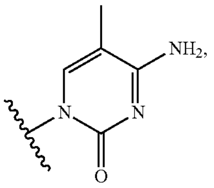
(U)
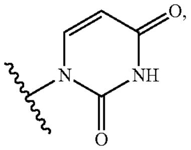
and
(I)
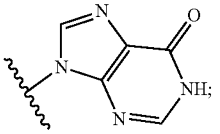
wherein the process comprises contacting a compound of Formula (A11):
(A11)
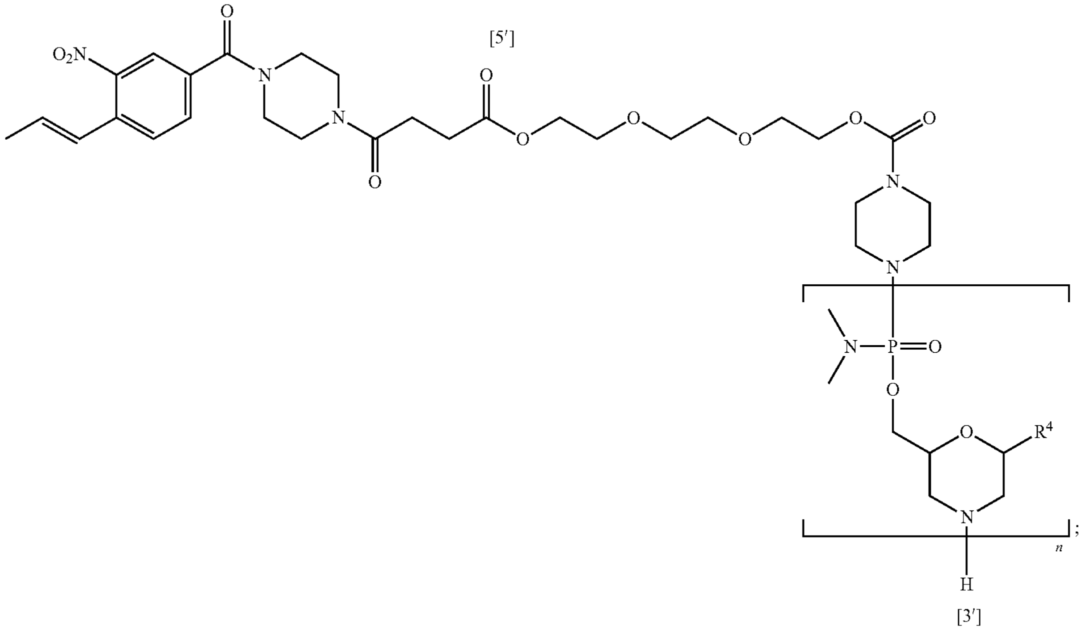

wherein n is an integer from 10 to 40, and $R^4$ is, independently for each occurrence, selected from the group consisting of:

(PC)

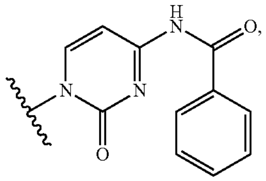

(DPG)

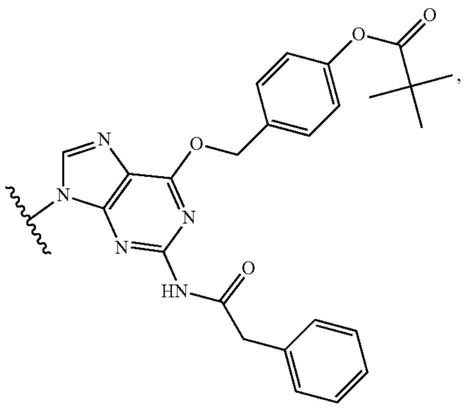

(T)

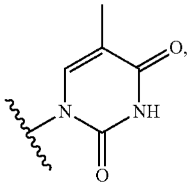

(PA)

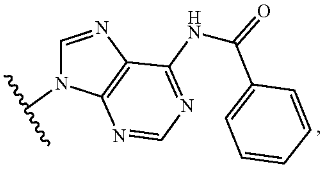

(P5mC)

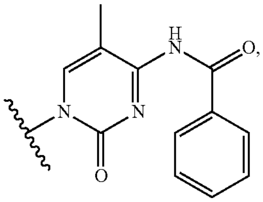

(U)

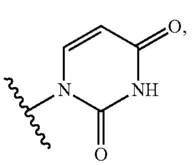

(I)

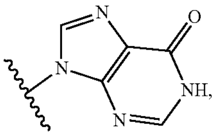

and

-continued (PG)

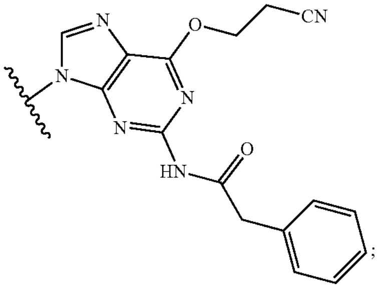

and with a deprotecting agent to form the oligomeric compound of Formula (A).

In another aspect, provided herein is a process for preparing an oligomeric compound of Formula (A):

(A)

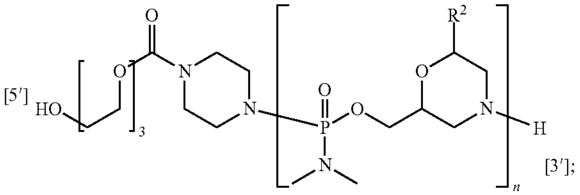

wherein n is an integer from 10 to 40, and each $R^2$ is, independently for each occurrence, selected from the group consisting of:

(C)

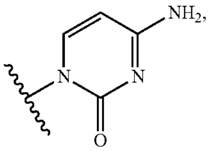

(G)

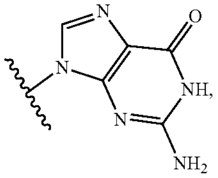

(T)

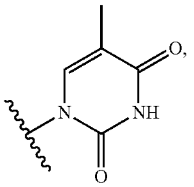

(A)

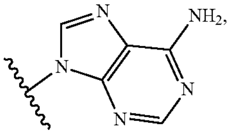

-continued (5mC)

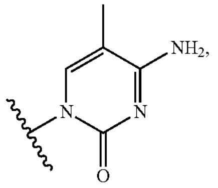

(U)

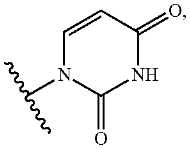

and (I)

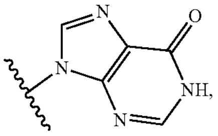

wherein the process comprises the sequential steps of:

(a) contacting a compound of Formula (A1):

(A1)

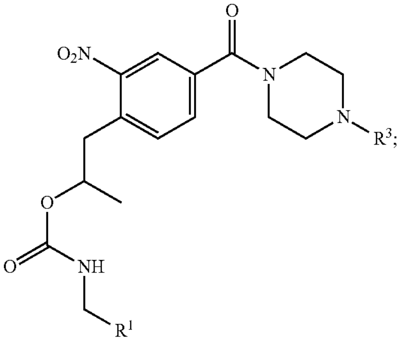

wherein $R^1$ is a support-medium and $R^3$ is selected from the group consisting of trityl, monomethoxytrityl, dimethoxytrityl and trimethoxytrityl;

with a deblocking agent to form the compound of Formula (II):

(II)

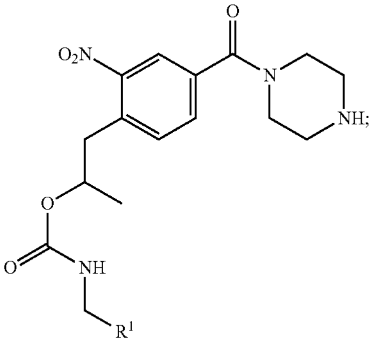

wherein $R^1$ is a support-medium;

(b) contacting the compound of Formula (II) with a compound of Formula (A2):

(A2)

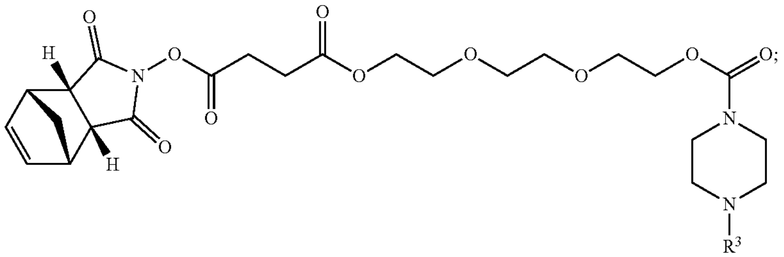

wherein $R^3$ is selected from the group consisting of trityl, monomethoxytrityl, dimethoxytrityl and trimethoxytrityl;

to form a compound of Formula (A3):

(A3)

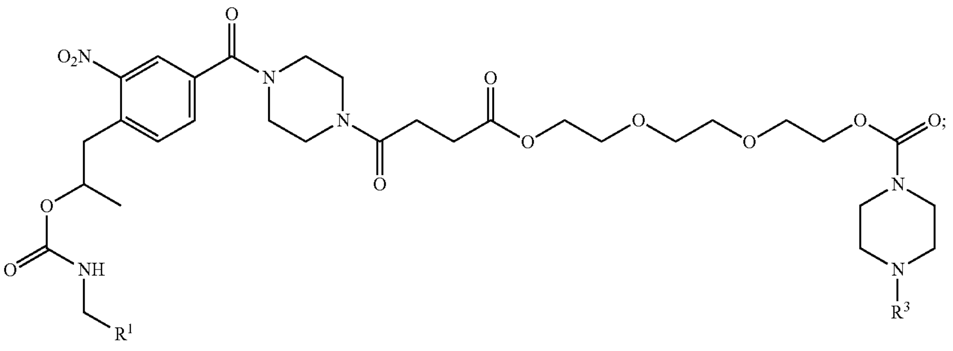

wherein $R^1$ is a support-medium, and $R^3$ is selected from the group consisting of trityl, monomethoxytrityl, dimethoxytrityl and trimethoxytrityl;

(c) contacting the compound of Formula (A3) with a deblocking agent to form a compound of Formula (IV):

(IV)

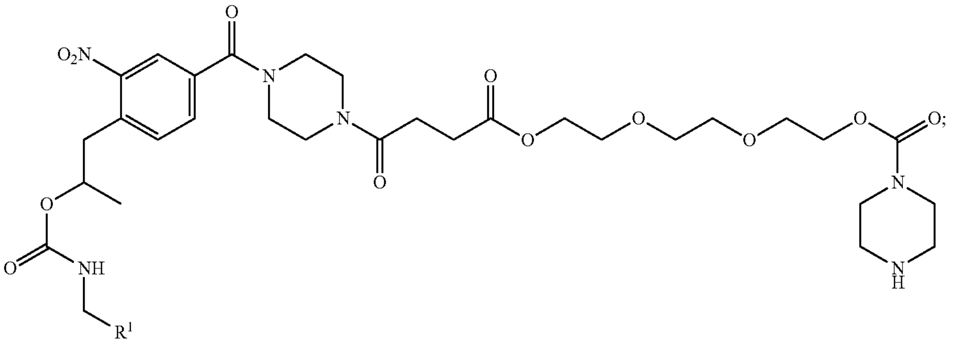

wherein $R^1$ is a support-medium;

(d) contacting the compound of Formula (IV) with a compound of Formula (A4):

(A4)

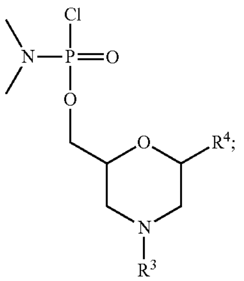

wherein $R^3$ is selected from the group consisting of trityl, monomethoxytrityl, dimethoxytrityl and trimethoxytrityl, and $R^4$ is selected from the group consisting of:

(PC)

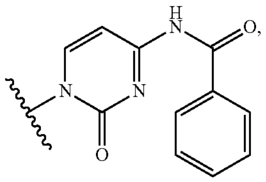

(DPG)

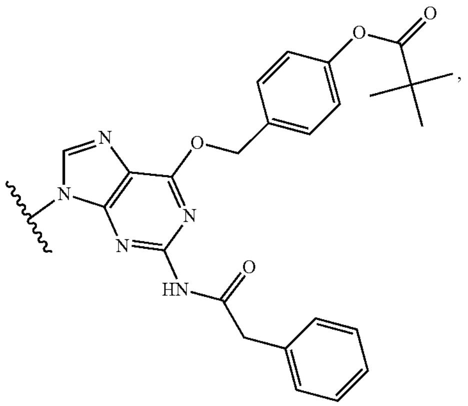

-continued
(T)
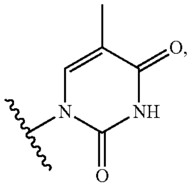
(PA)
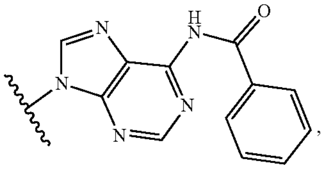
(P5mC)
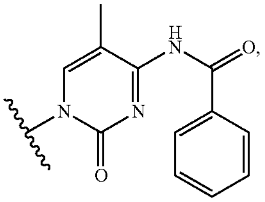
-continued
(U)
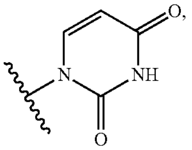
(I)
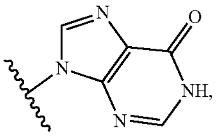
and
(PG)
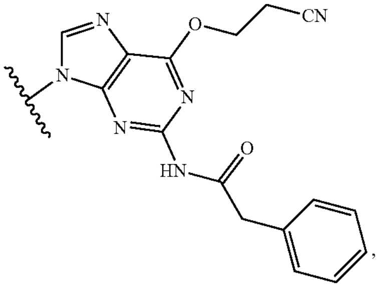
to form a compound of Formula (A5):
(A5)
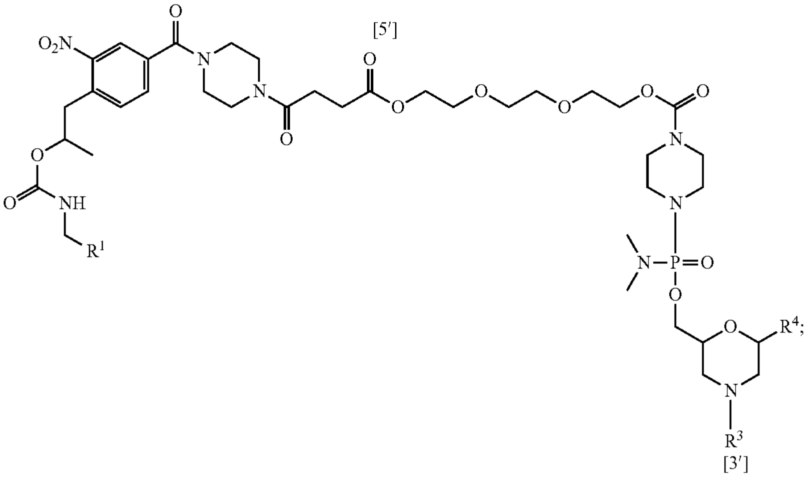

wherein $R^1$ is a support-medium, $R^3$ is selected from the group consisting of trityl, monomethoxytrityl, dimethoxytrityl and trimethoxytrityl, and $R^4$ is selected from the group consisting of:

(PC)

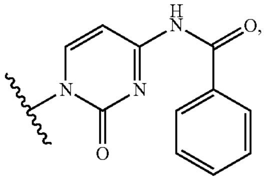

(DPG)

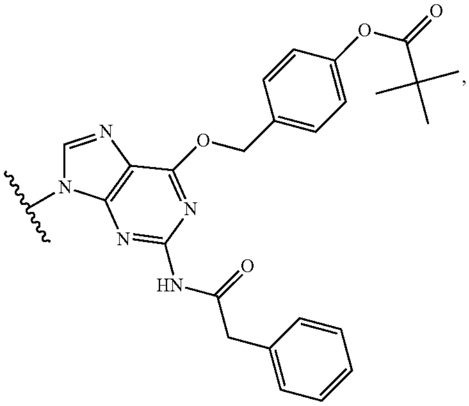

(T)

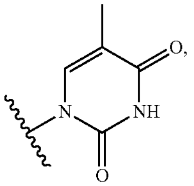

(PA)

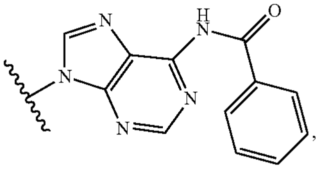

(P5mC)

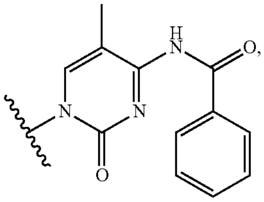

(U)

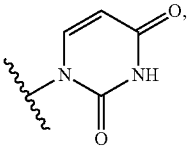

(I)

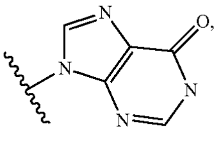

and

-continued (PG)

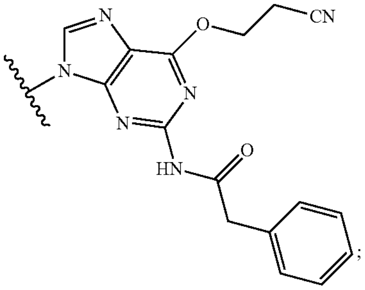

(e) performing n−1 iterations of the sequential steps of:

(e1) contacting the product formed by the immediately prior step with a deblocking agent; and (e2) contacting the compound formed by the immediately prior step with a compound of Formula (A8):

(A8)

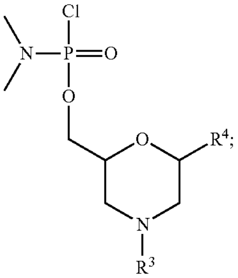

wherein $R^3$ is selected from the group consisting of trityl, monomethoxytrityl, dimethoxytrityl and trimethoxytrityl, and $R^4$ is, independently for each compound of Formula (A8), selected from the group consisting of:

(PC)

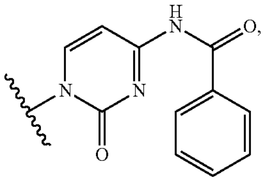

(DPG)

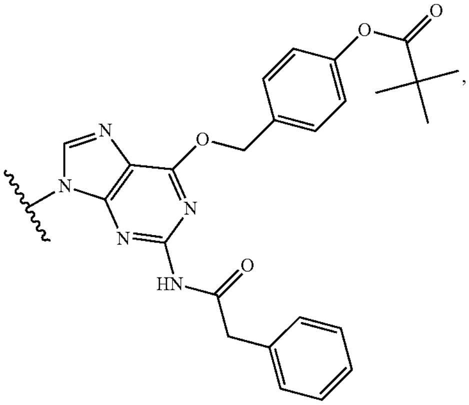

-continued
(T)
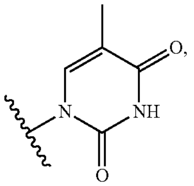
(U)
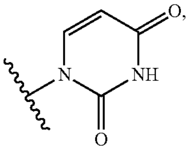
(PA)
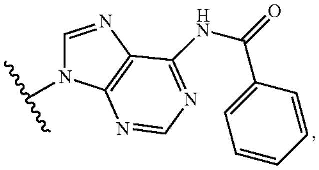
(I)
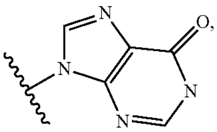
and
(PG)
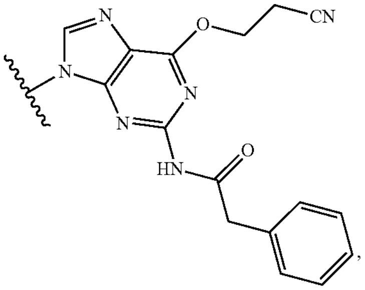
(P5mC)
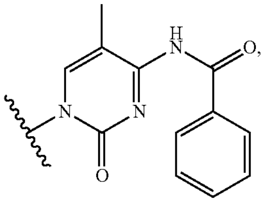
to form a compound of Formula (A9):
(A9)
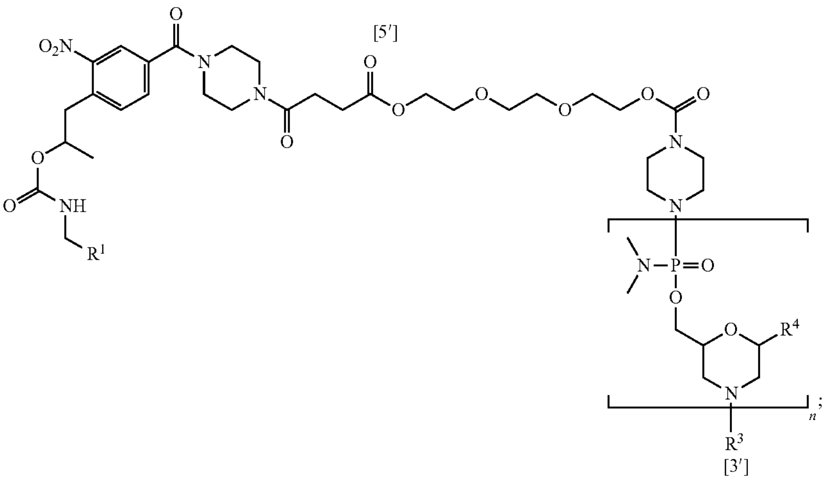
;

wherein n is an integer from 10 to 40, $R^1$ is a support-medium, $R^3$ is selected from the group consisting of trityl, monomethoxytrityl, dimethoxytrityl and trimethoxytrityl, and $R^4$ is, independently for each occurrence, selected from the group consisting of:

(PC)

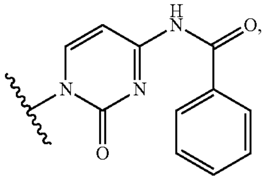

(DPG)

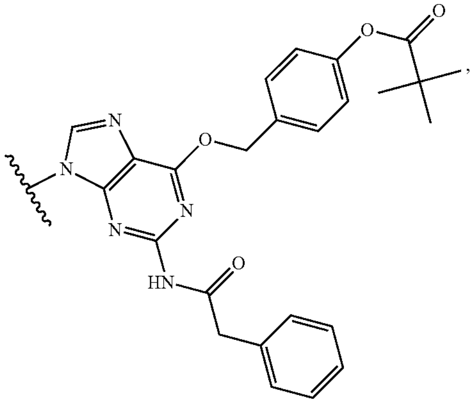

(T)

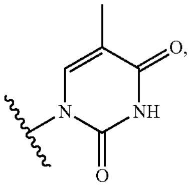

(PA)

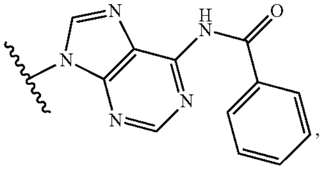

-continued (P5mC)

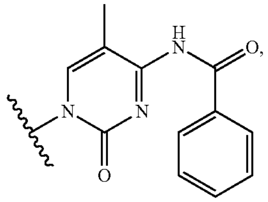

(U)

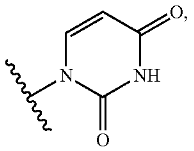

(I)

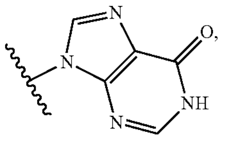

and (PG)

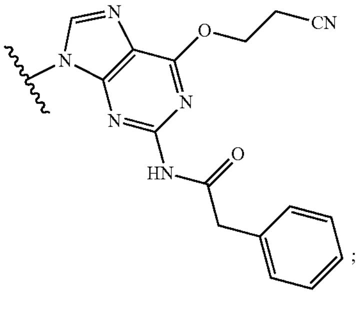

and (f) contacting the compound of Formula (A9) with a deblocking agent to form a compound of Formula (A10):

(A10)

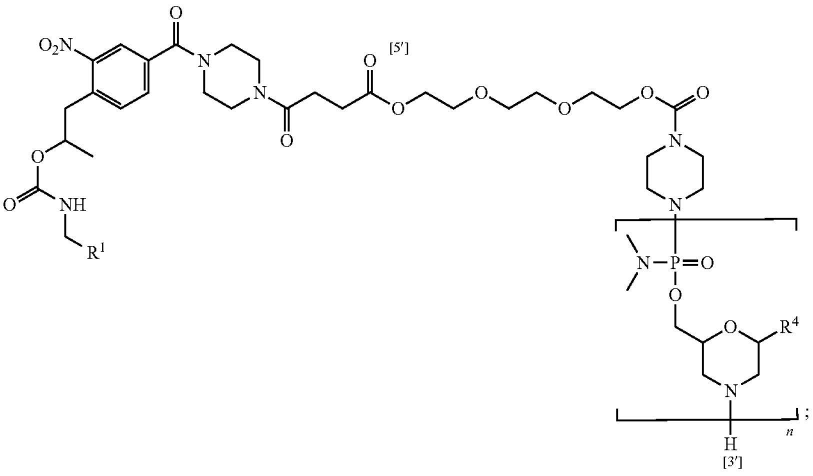

wherein n is an integer from 10 to 40, $R^1$ is a support-medium, and $R^4$ is, independently for each occurrence, selected from the group consisting of:
(PC)
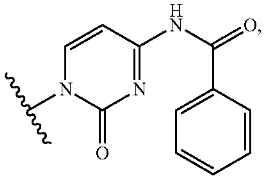
(DPG)
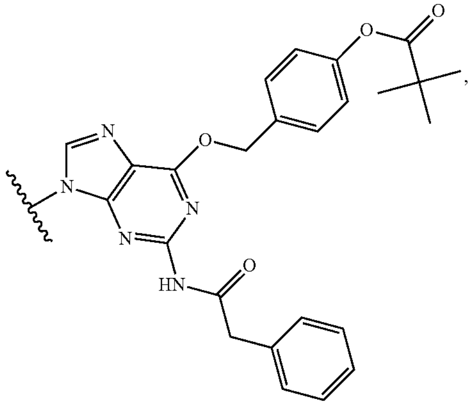
(T)
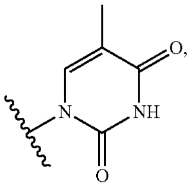
(PA)
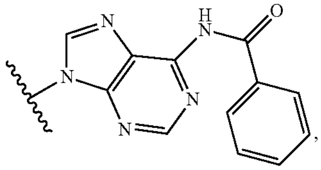
-continued
(P5mC)
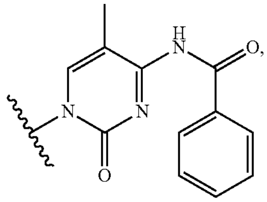
(U)
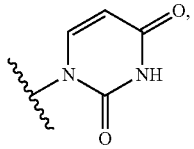
(I)
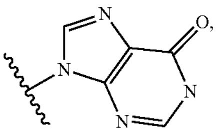
and
(PG)
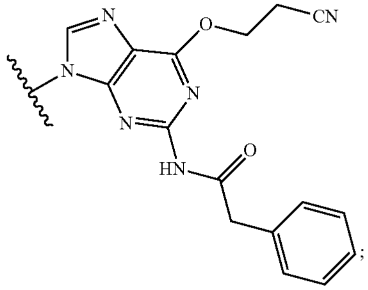
(g) contacting the compound of Formula (A10) with a cleaving agent to form a compound of Formula (A11):
(A11)
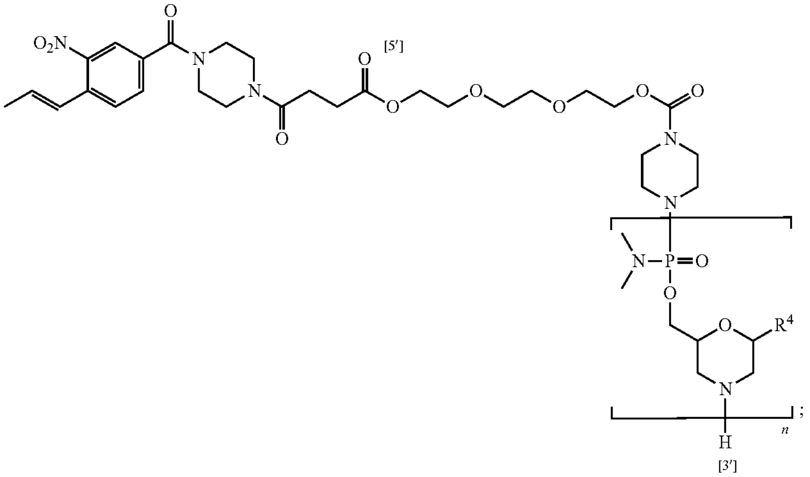

wherein n is an integer from 10 to 40, and $R^4$ is, independently for each occurrence, selected from the group consisting of:

(PC)

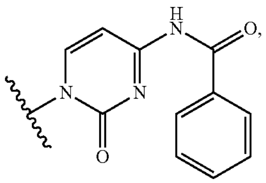

(DPG)

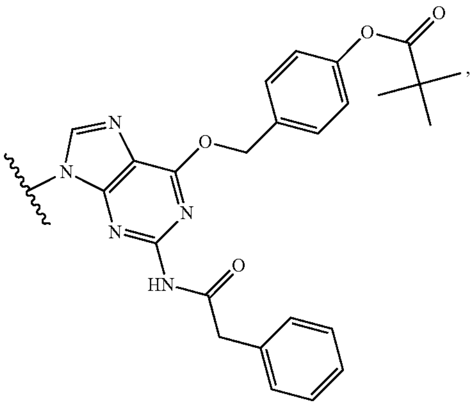

(T)

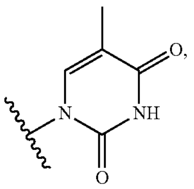

(PA)

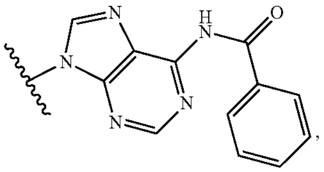

(P5mC)

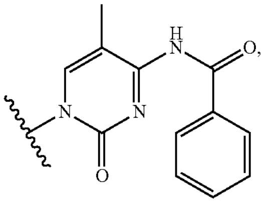

(U)

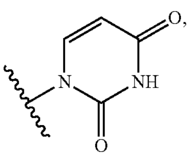

(I)

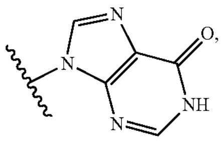

and

-continued (PG)

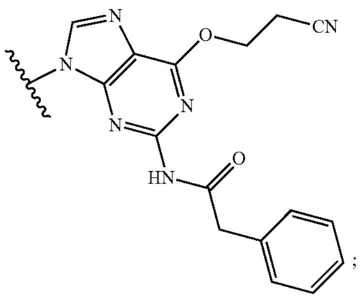

and (h) contacting the compound of Formula (A11) with a deprotecting agent to form the oligomeric compound of Formula (A).

In one embodiment, step (d) or step (e2) further comprises contacting the compound of Formula (IV) or the compound formed by the immediately prior step, respectively, with a capping agent.

In another embodiment, each step is performed in the presence of at least one solvent.

In yet another embodiment, the deblocking agent used in each step is a solution comprising a halogenated acid.

In still another embodiment, the deblocking agent used in each step is cyanoacetic acid.

In another embodiment, the halogenated acid is selected from the group consisting of chloroacetic acid, dichloroacetic acid, trichloroacetic acid, fluoroacetic acid, difluoroacetic acid, and trifluoroacetic acid.

In another embodiment, the halogenated acid is trifluoroacetic acid.

In yet another embodiment, at least one of steps (a), (c), (e), and (g1) further comprise the step of contacting the deblocked compound of each step with a neutralization agent.

In still another embodiment, each of steps (a), (c), (e), and (g1) further comprise the step of contacting the deblocked compound of each step with a neutralization agent.

In another embodiment, the neutralization agent is in a solution comprising dichloromethane and isopropyl alcohol.

In yet another embodiment, the neutralization agent is a monoalkyl, dialkyl, or trialkyl amine.

In still another embodiment, the neutralization agent is N,N-diisopropylethylamine.

In another embodiment, the deblocking agent used in each step is a solution comprising 4-cyanopyridine, dichloromethane, trifluoroacetic acid, trifluoroethanol, and water.

In yet another embodiment, the capping agent is in a solution comprising ethylmorpholine and methylpyrrolidinone.

In still another embodiment, the capping agent is an acid anhydride.

In another embodiment, the acid anhydride is benzoic anhydride.

In another embodiment, the compounds of Formula (A4) and Formula (A8) are each,
independently, in a solution comprising ethylmorpholine and dimethylimidazolidinone.

In another embodiment, the cleavage agent comprises dithiothreitol and 1,8-diazabicyclo[5.4.0]undec-7-ene.

In still another embodiment, the cleavage agent is in a solution comprising N-methyl-2-pyrrolidone.

In yet another embodiment, the deprotecting agent comprises $NH_3$.

In still another embodiment, the deprotecting agent is in an aqueous solution.

In yet another embodiment, the support-medium comprises polystyrene with 1% crosslinked divinylbenzene.

In another embodiment, the compound of Formula (A4) is of Formula (A4a):

(A4a)

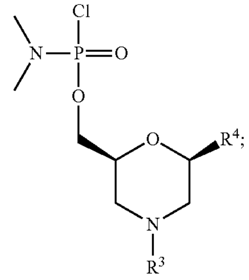

wherein:

$R^3$ is selected from the group consisting of trityl, monomethoxytrityl, dimethoxytrityl and trimethoxytrityl, and $R^4$ is selected from:

(PC)

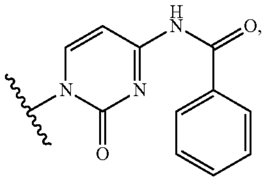

(DPG)

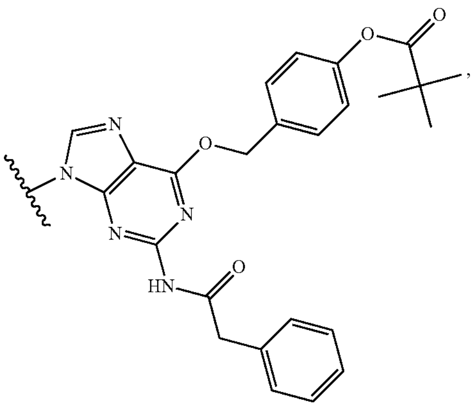

(T)

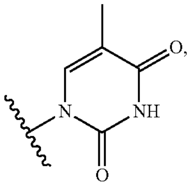

-continued (PA)

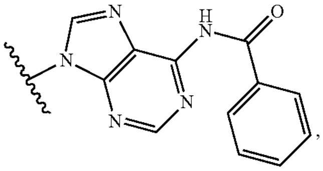

(P5mC)

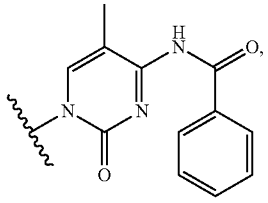

(U)

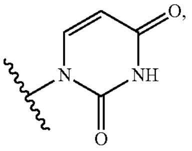

(I)

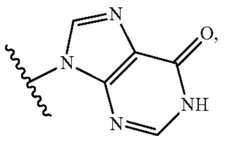

and (PG)

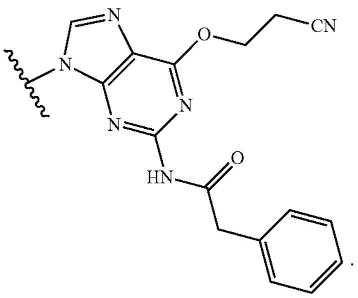

In another embodiment, the compound of Formula (A5) is of Formula (A5a):
(A5a)
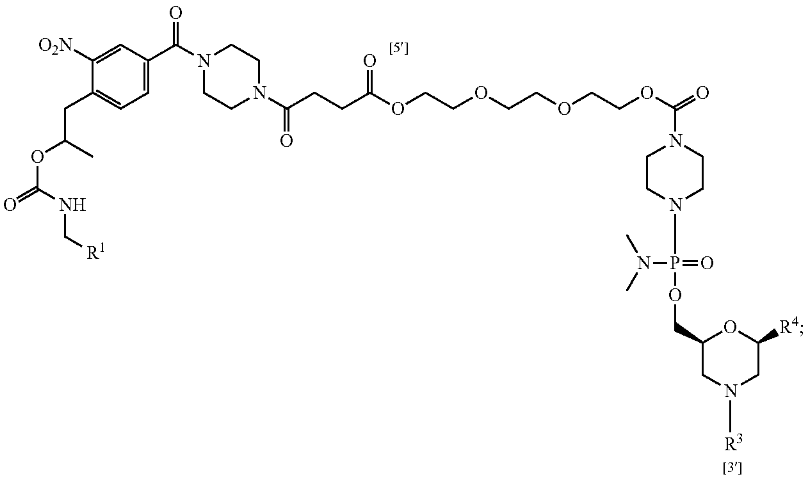
wherein:
$R^1$ is a support-medium
$R^3$ is selected from the group consisting of trityl, monomethoxytrityl, dimethoxytrityl and trimethoxytrityl, and
$R^4$ is selected from:
(PC)
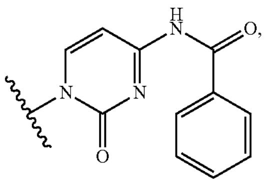
(DPG)
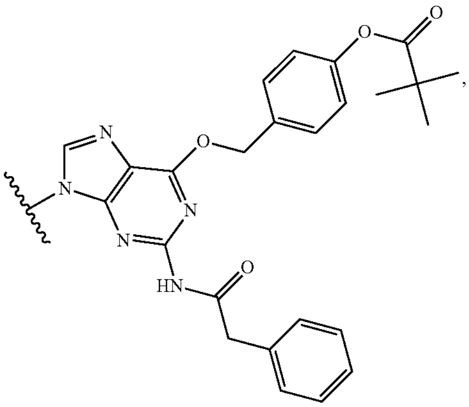
(T)
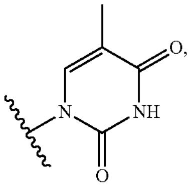
-continued
(PA)
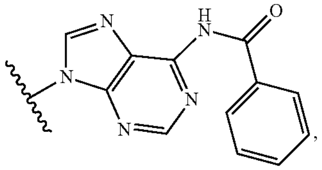
(P5mC)
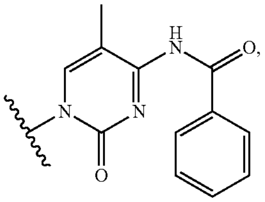
(U)
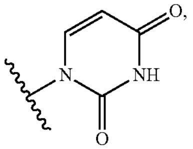
(I)
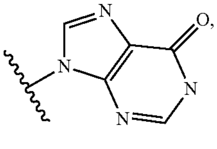
and
(PG)
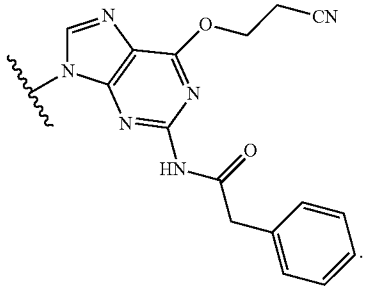

In yet another embodiment, the compound of Formula (A8) is of Formula (A8a):
(A8a)
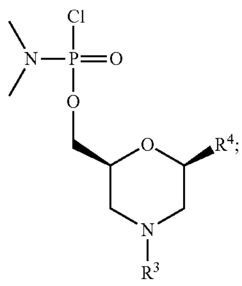
wherein:
$R^3$ is selected from the group consisting of trityl, monomethoxytrityl, dimethoxytrityl and trimethoxytrityl, and
$R^4$ is, independently at each occurrence of the compound of Formula (A8a), selected from the group consisting of:
(PC)
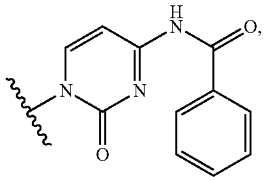
(DPG)
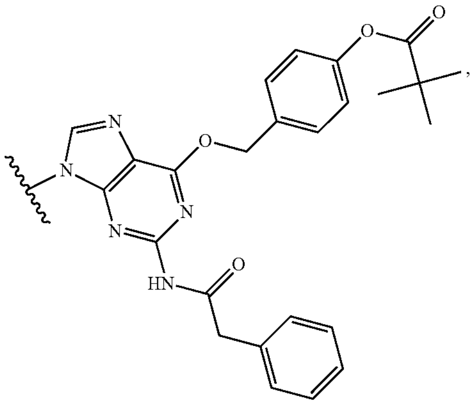
(T)
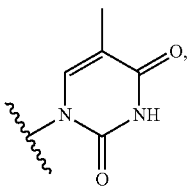
-continued
(PA)
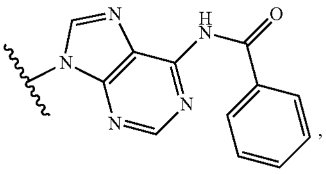
(P5mC)
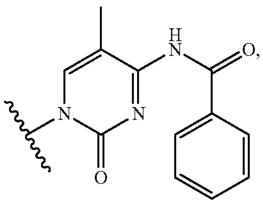
(U)
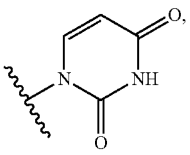
(I)
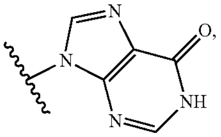
and
(PG)
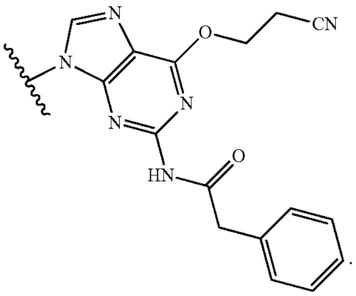

In still another embodiment, the compound of formula (A9) is of Formula (A9a):
(A9a)
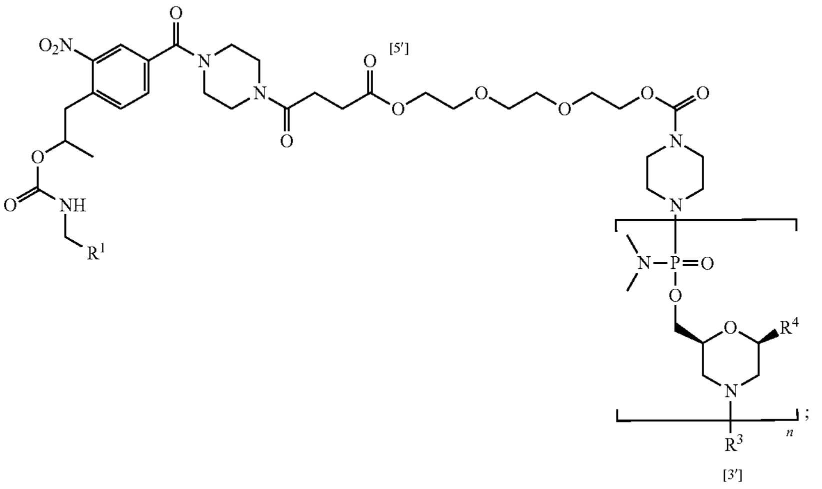
wherein:
n is an integer from 10 to 40,
$R^1$ is a support-medium,
$R^3$ is selected from the group consisting of trityl, monomethoxytrityl, dimethoxytrityl and trimethoxytrityl, and
$R^4$ is, independently for each occurrence, selected from the group consisting of:
(PC)
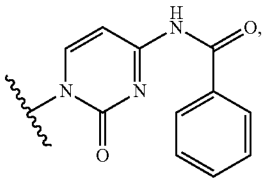
(DPG)
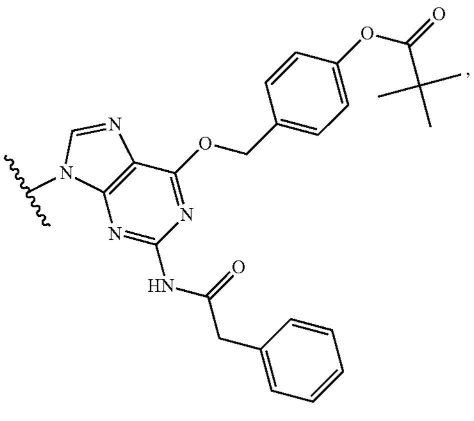
(T)
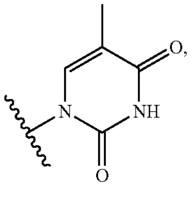
-continued
(PA)
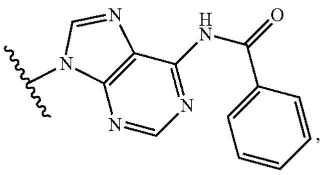
(P5mC)
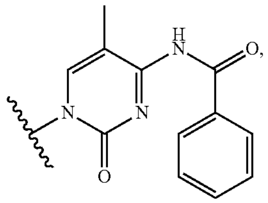
(U)
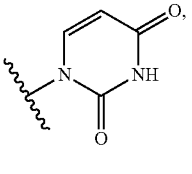
(I)
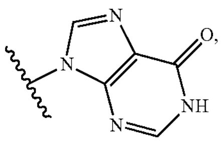
and -continued
(PG)
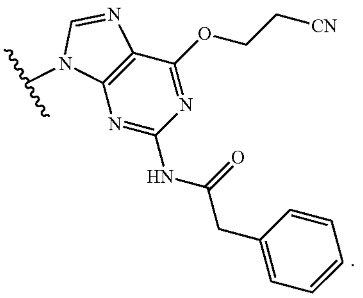
In another embodiment, the compound of Formula (A10) is of Formula (A10a):
(A10a)
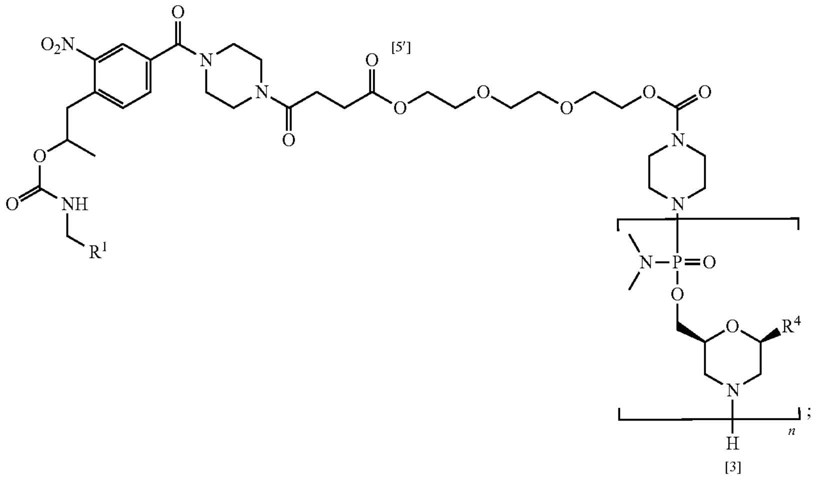
wherein:
n is an integer from 10 to 40,
$R^1$ is a support-medium, and
$R^4$ is, independently for each occurrence, selected from the group consisting of:
(PC)
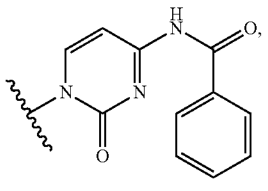
-continued
(DPG)
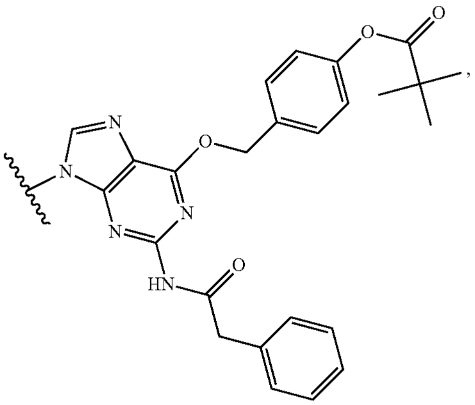
(T)
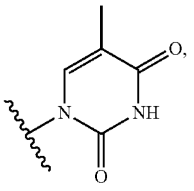

-continued
(PA)
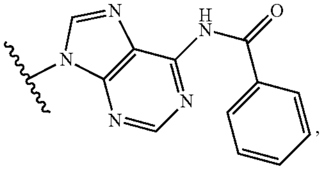
(P5mC)
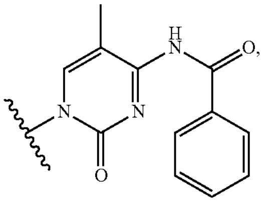
(U)
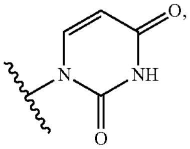
-continued
(I)
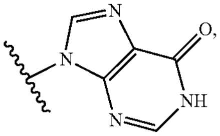
and
(PG)
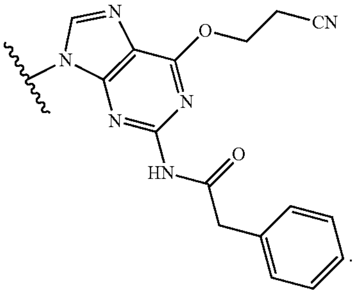
In another embodiment, the compound of Formula (A11) is of Formula (A11a):
(A11a)
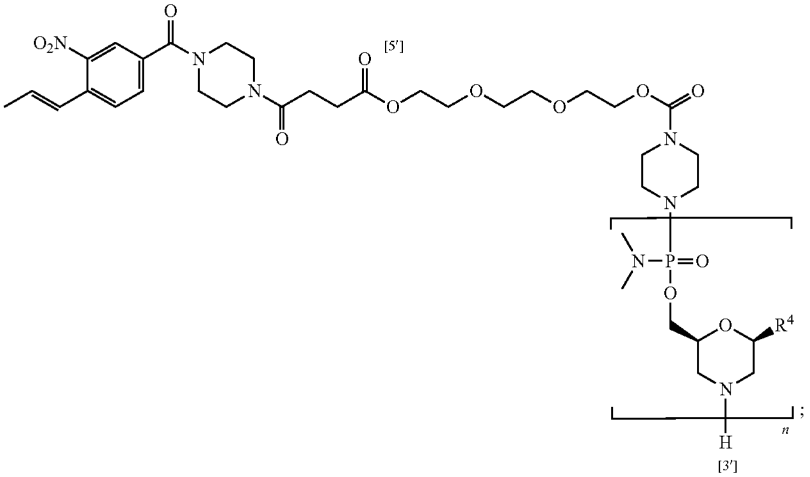

wherein:
n is an integer from 10 to 40, and
$R^4$ is, independently for each occurrence, selected from the group consisting of:
(PC)
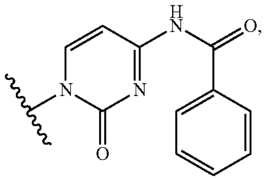
(DPG)
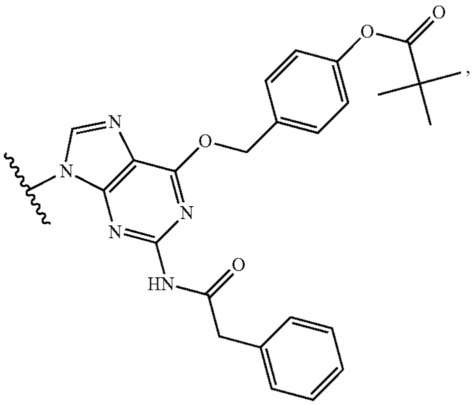
(T)
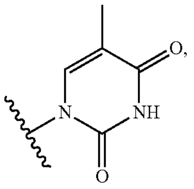
(PA)
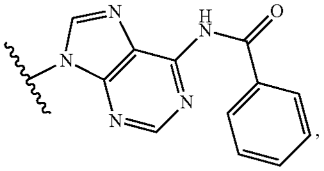
(P5mC)
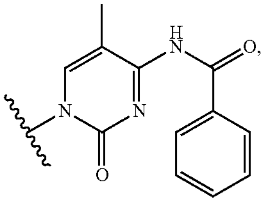
(U)
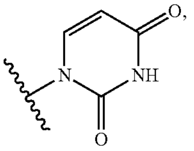
-continued
(I)
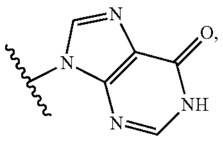
and
(PG)
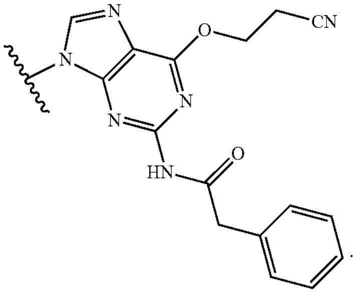
In an embodiment of the oligomeric compound of Formula (A), n is 30, and $R^2$ is at each position from 1 to 25 and 5' to 3':
| Position No. 5' to 3' | $R^2$ |
|---|---|
| 1 | G |
| 2 | T |
| 3 | T |
| 4 | G |
| 5 | C |
| 6 | C |
| 7 | T |
| 8 | C |
| 9 | C |
| 10 | G |
| 11 | G |
| 12 | T |
| 13 | T |
| 14 | C |
| 15 | T |
| 16 | G |
| 17 | A |
| 18 | A |
| 19 | G |
| 20 | G |
| 21 | T |
| 22 | G |
| 23 | T |
| 24 | T |
| 25 | C |

wherein the oligomeric compound of Formula (A) is a compound of Formula (G):
(G)
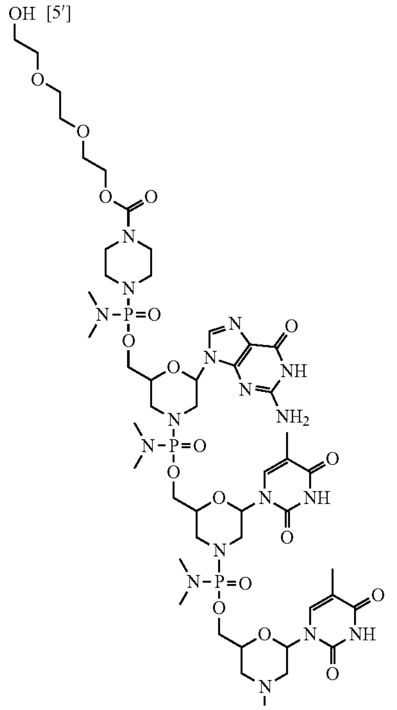
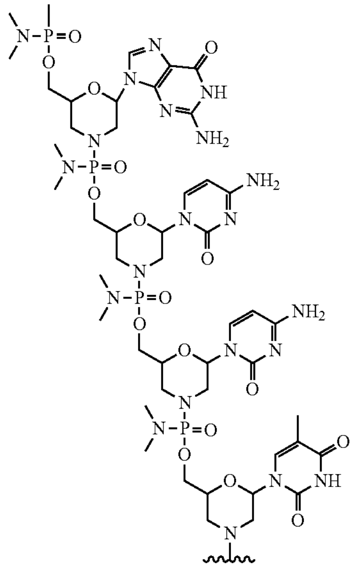
BREAK A
-continued
BREAK A
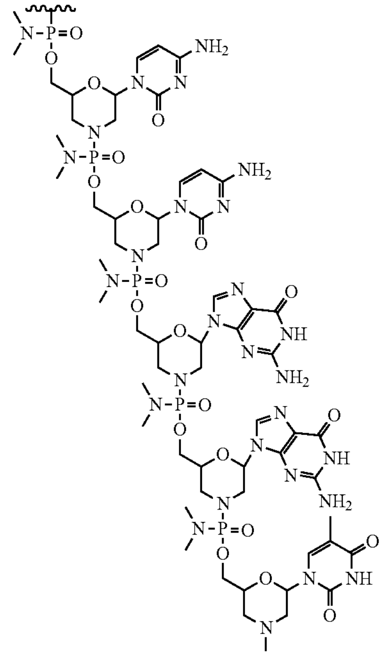
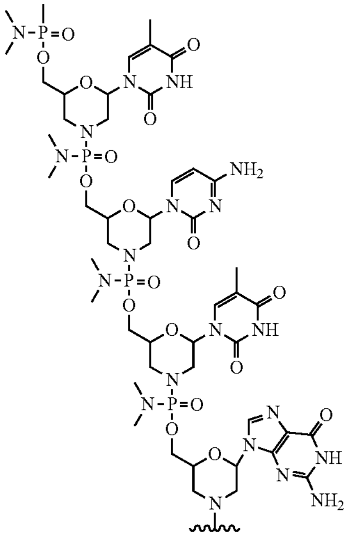
BREAK B -continued

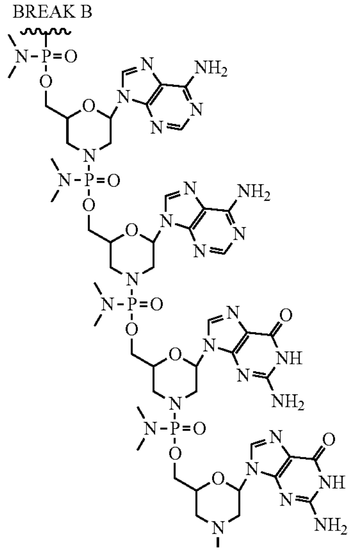

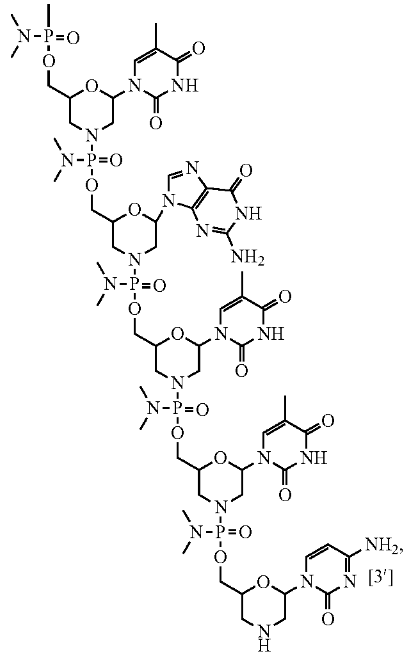

or a pharmaceutically acceptable salt thereof.

Golodirsen, formerly known by its code name "SPR-4053," is a PMO having the base sequence 5'-GTTGCCTCCGGTTCTGAAGGTGTTC-3'(SEQ ID NO:1). Golodirsen is registered under CAS Registry Number 1422959-91-8. Chemical names include:

all-P-ambo-[P,2',3'-trideoxy-P-(dimethylamino)-2',3'-imino-2',3'-seco](2'a→5')(G-T-T-G-C-C-T-C-C-G-G-T-T-C-T-G-A-A-G-G-T-G-T-T-C) 5'[4-({2-[2-(2-hydroxyethoxy)ethoxy]ethoxy}carbonyl)-N,N-dimethylpiperazine-1-phosphonamidate]

Golodirsen has the following structure:

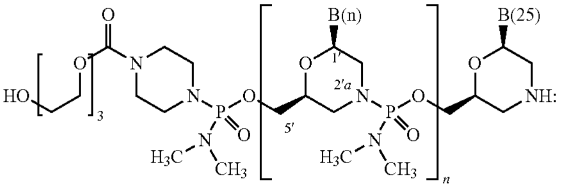

G-T-T-G-C-C-T-C-C-G-G-T-T-C-T-G-A-A-G-G-T-G-T-T-C n = 1 - 24 and also is represented by the following chemical structure:

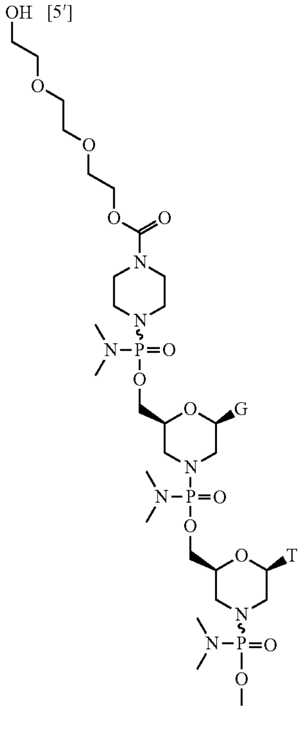

-continued
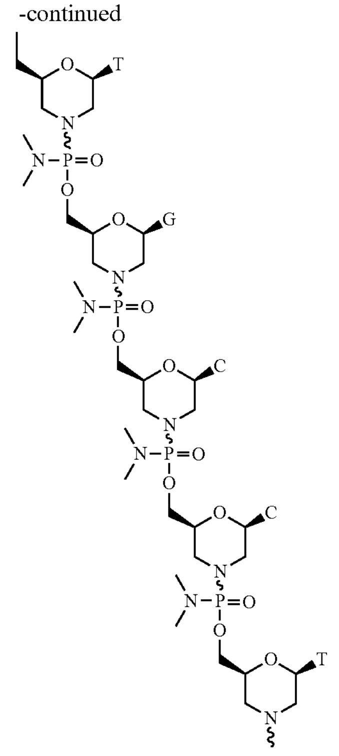
BREAK A
-continued
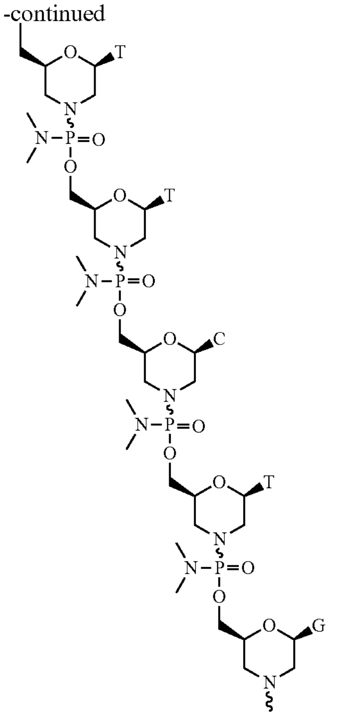
BREAK B
BREAK A
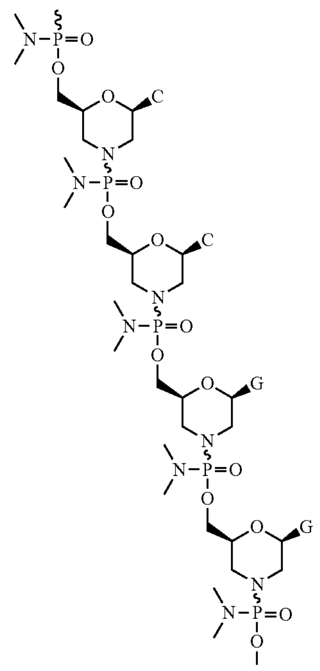
BREAK B
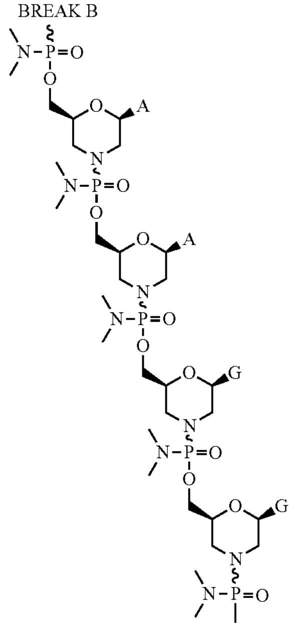

-continued
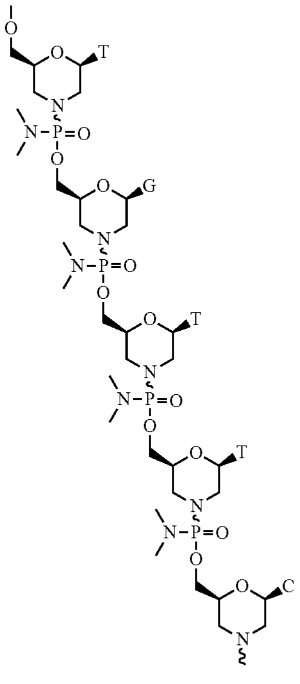
[3']
Bases:
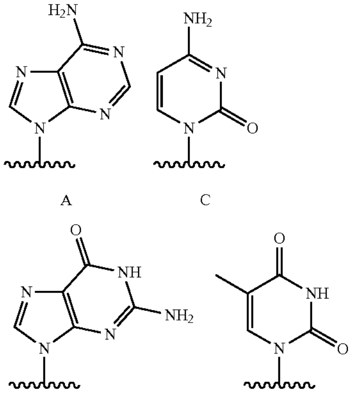
A C G T ($m^5U$)
The sequence of bases from the 5' end to the 3' end is: GTTGCCTCCGGTTCTGAAGGTGTTC
Golodirsen can also be depicted by the structure of Formula (XII):
(XII)
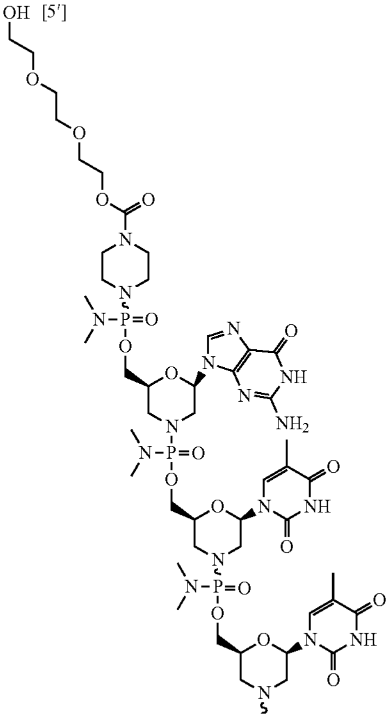
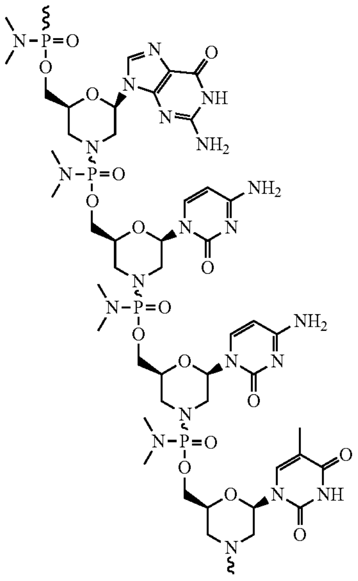
BREAK A -continued
BREAK A
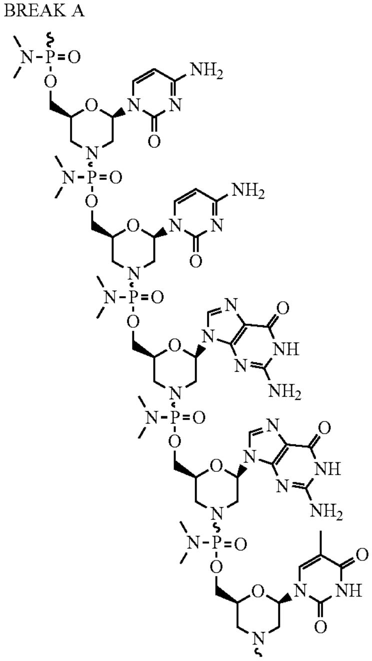
-continued
BREAK B
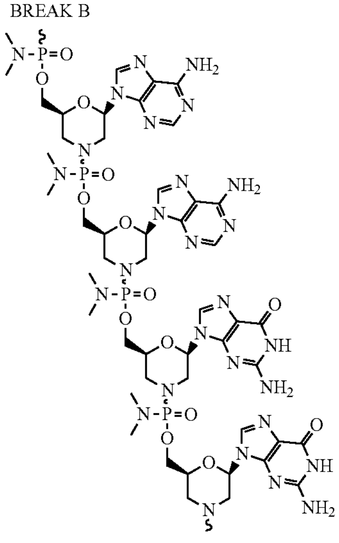
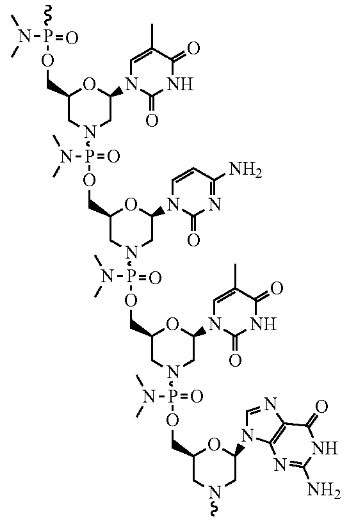
BREAK B
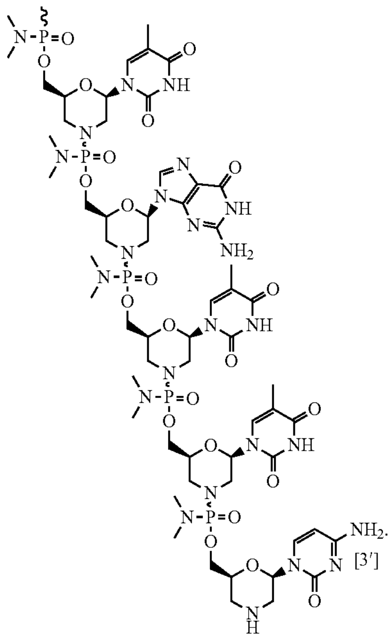
[3']

Thus, in one embodiment of the process described above, the oligomeric compound of Formula (A) is a compound of Formula (G):
(G)
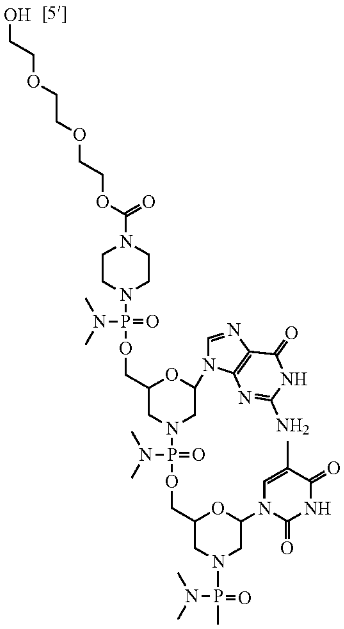
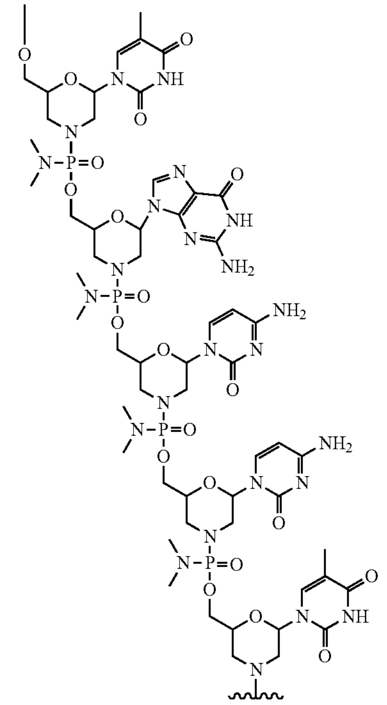
BREAK A
-continued
BREAK A
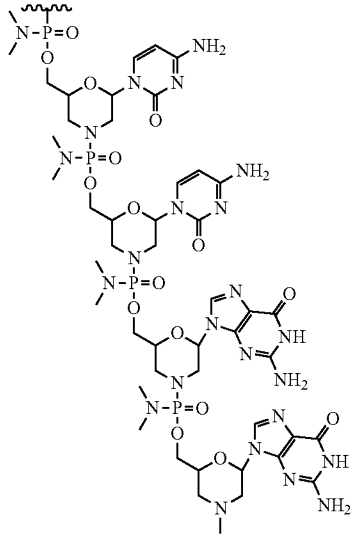
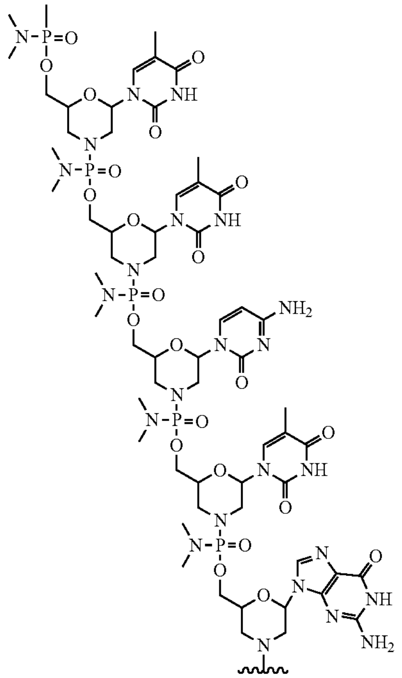
BREAK B -continued
BREAK B
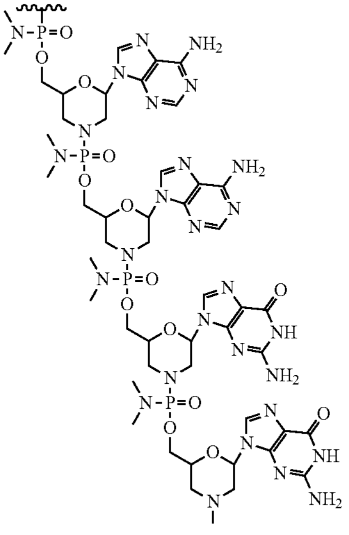
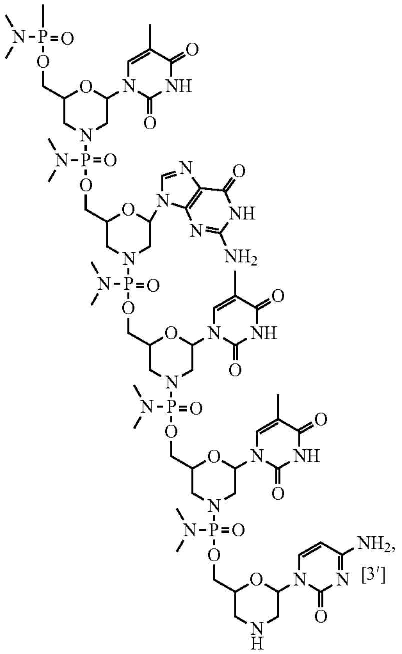
or a pharmaceutically acceptable salt thereof.
In yet another embodiment, the oligomeric compound of Formula (G) is an oligomeric compound of Formula (XII):
(XII)
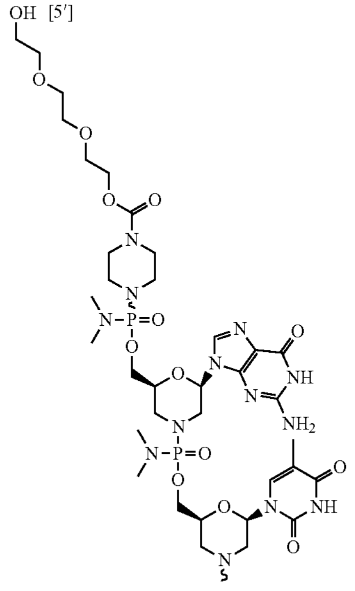
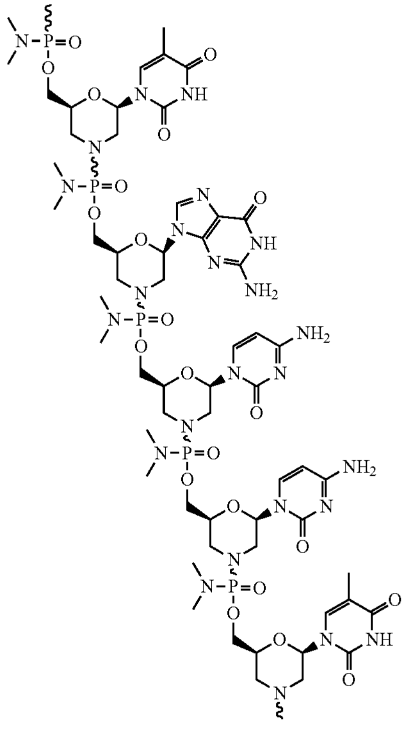
BREAK A -continued
BREAK A
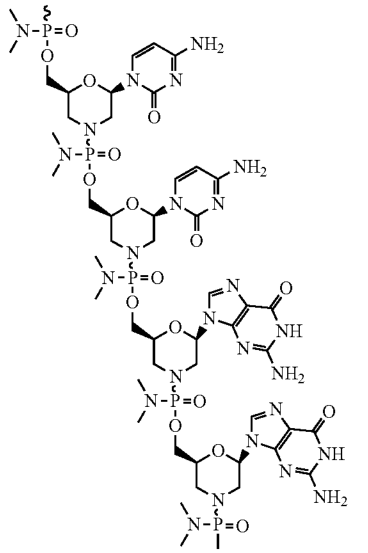
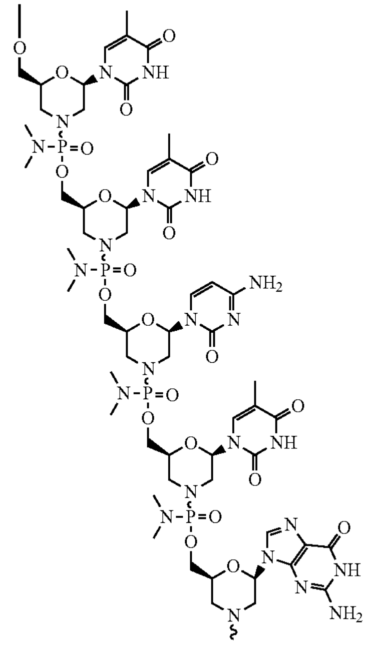
BREAK B
-continued
BREAK B
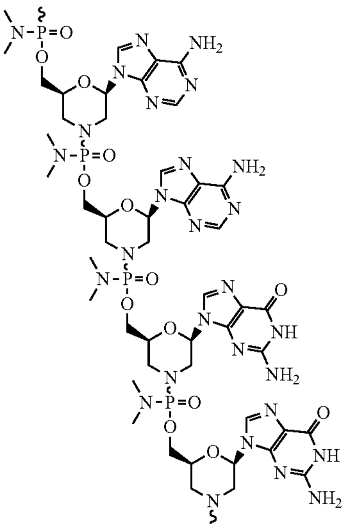
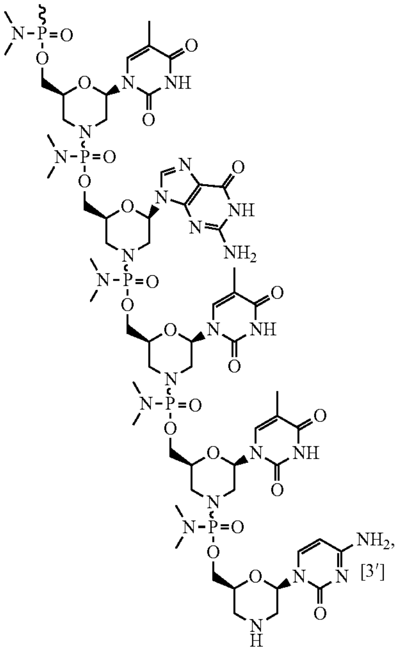
or a pharmaceutically acceptable salt thereof.
In still another embodiment, $R^3$ is, at each occurrence, trityl.

Processes for Preparing Golodirsen
Provided herein are processes for preparing Golodirsen.
In one aspect, provided herein is a process for preparing an oligomeric compound of Formula (G):
(G)
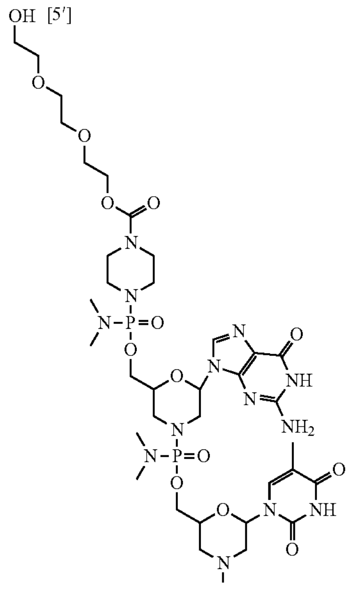
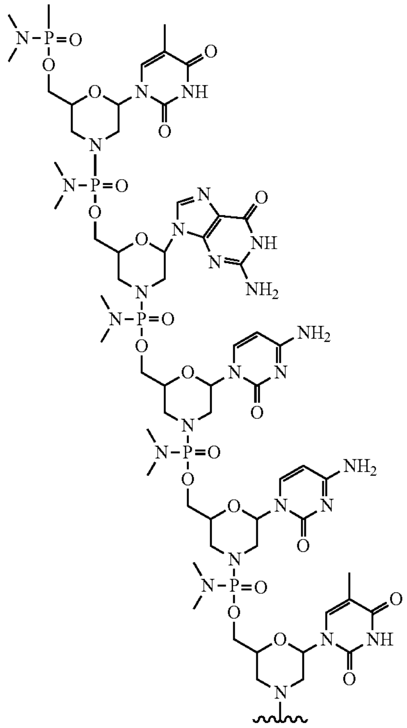
BREAK A
-continued
BREAK A
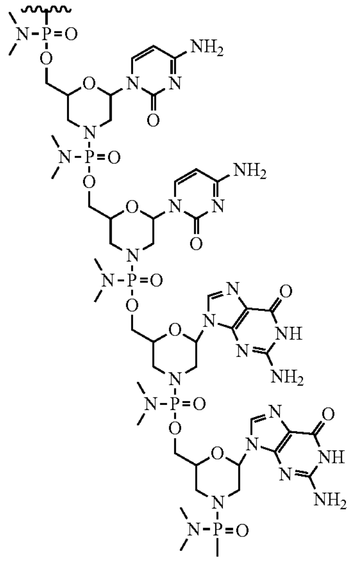
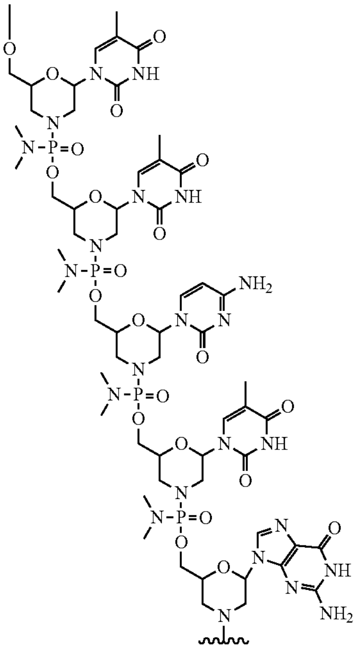
BREAK B -continued
BREAK B
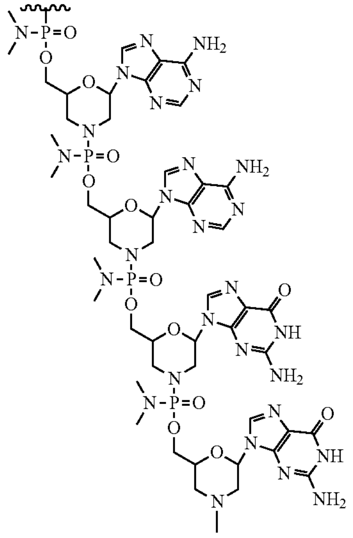
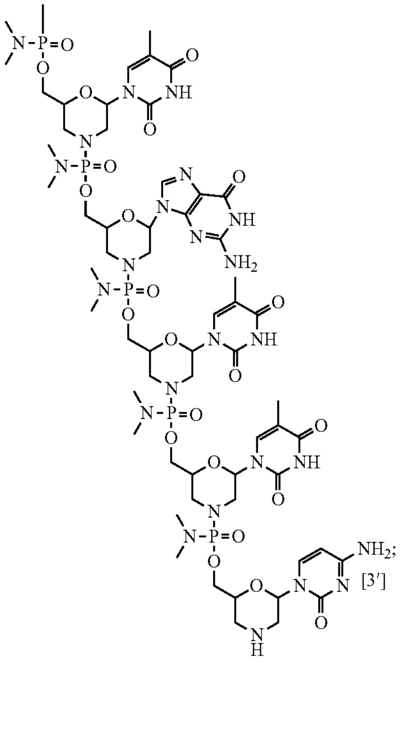
wherein the process comprises the sequential steps of:
(a) contacting a compound of Formula (I):
(I)
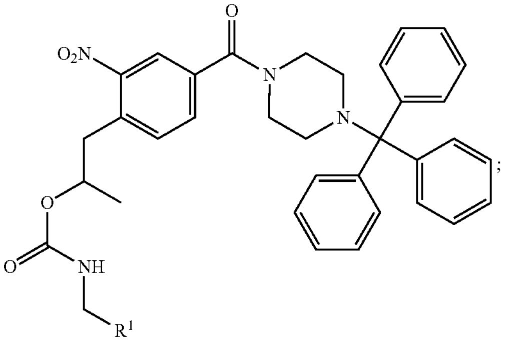
wherein $R^1$ is a support-medium,
with a deblocking agent to form the compound of Formula (II):
(II)
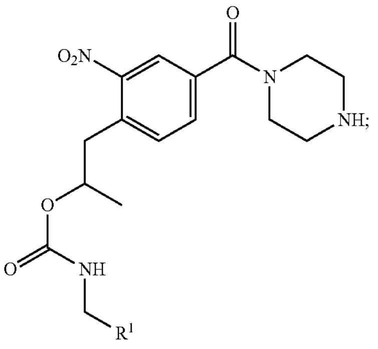

wherein $R^1$ is a support-medium;
(b) contacting the compound of Formula (II) with compound (B):
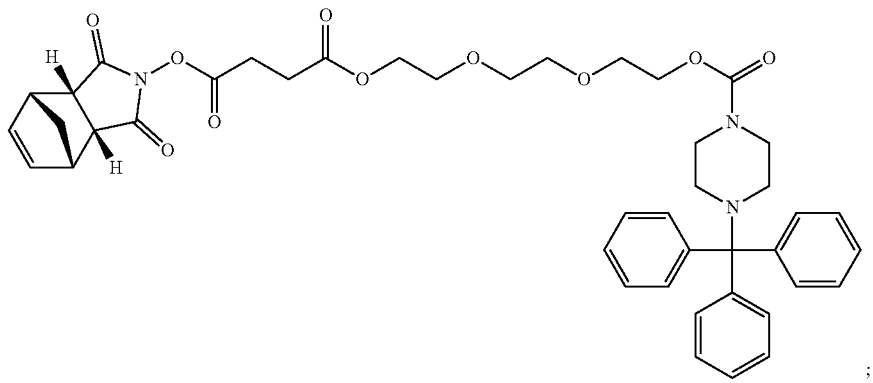
(B)
;
to form a compound of Formula (III):
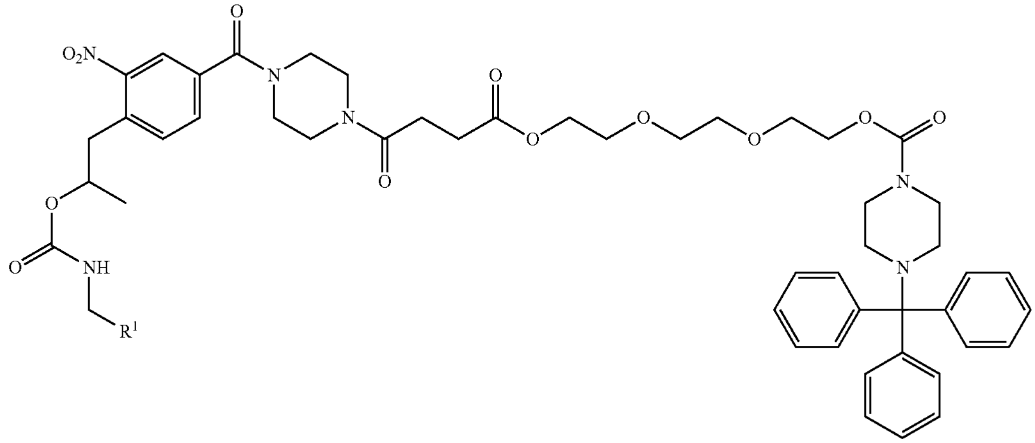
(III)
;
wherein R' is a support-medium;
(c) contacting the compound of Formula (III) with a deblocking agent to form a compound of Formula (IV):
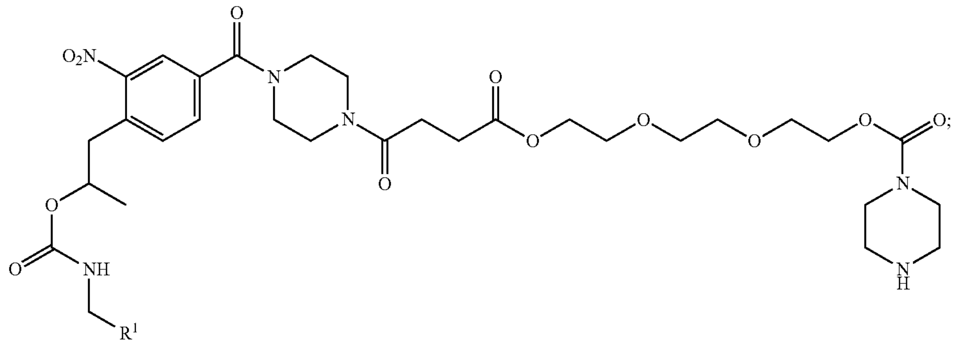
(IV)
;

wherein R' is a support-medium;
(d) contacting the compound of Formula (IV) with a compound of Formula (DPG):
(DPG)
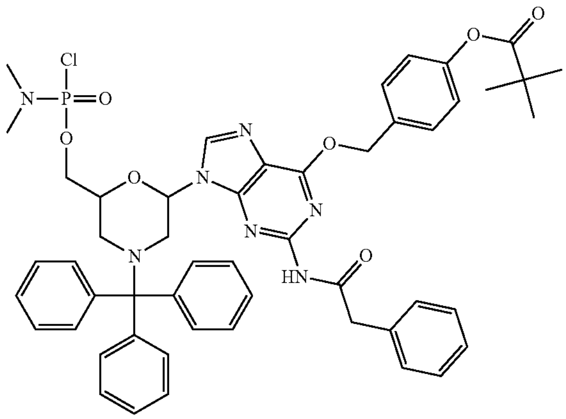
;
to form a compound of Formula (V):
(V)
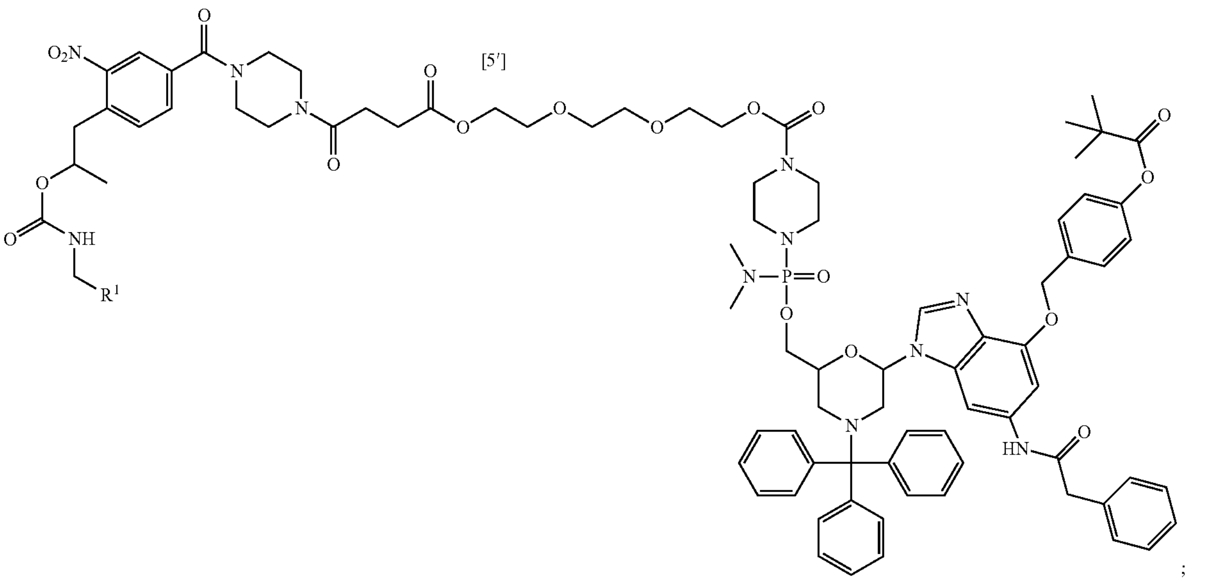
;
[3']

wherein $R^1$ is a support-medium;
(e) contacting the compound of Formula (V) with a deblocking agent to form a compound of Formula (VI):
(VI)
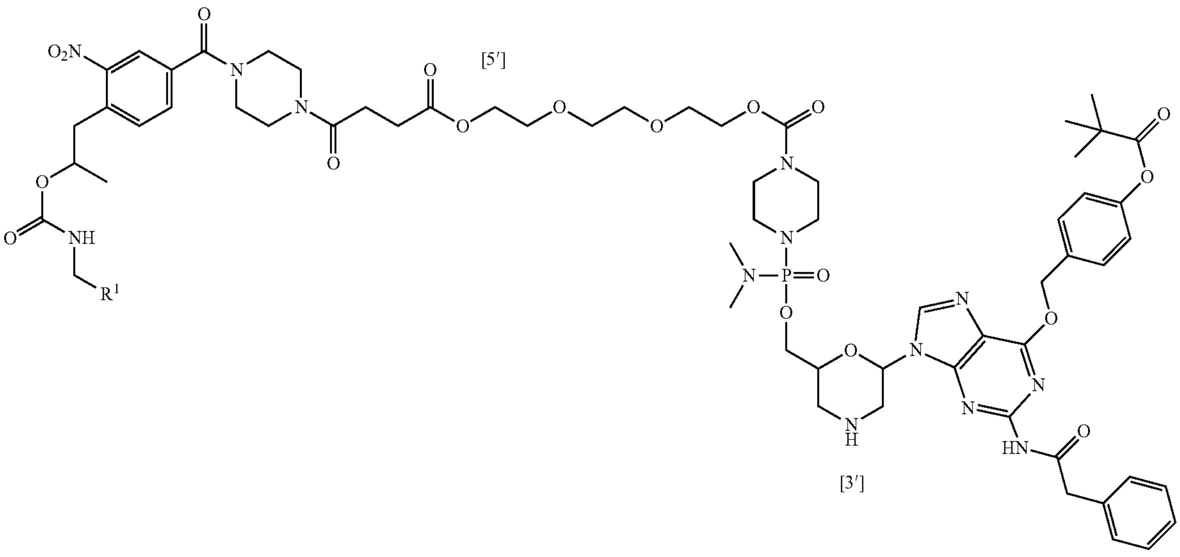
;

wherein $R^1$ is a support-medium;
(f) contacting the compound of Formula (VI) with a compound of Formula (T):
(T)
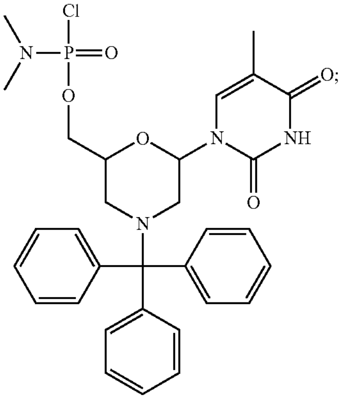
to form a compound of Formula (VII):
(VII)
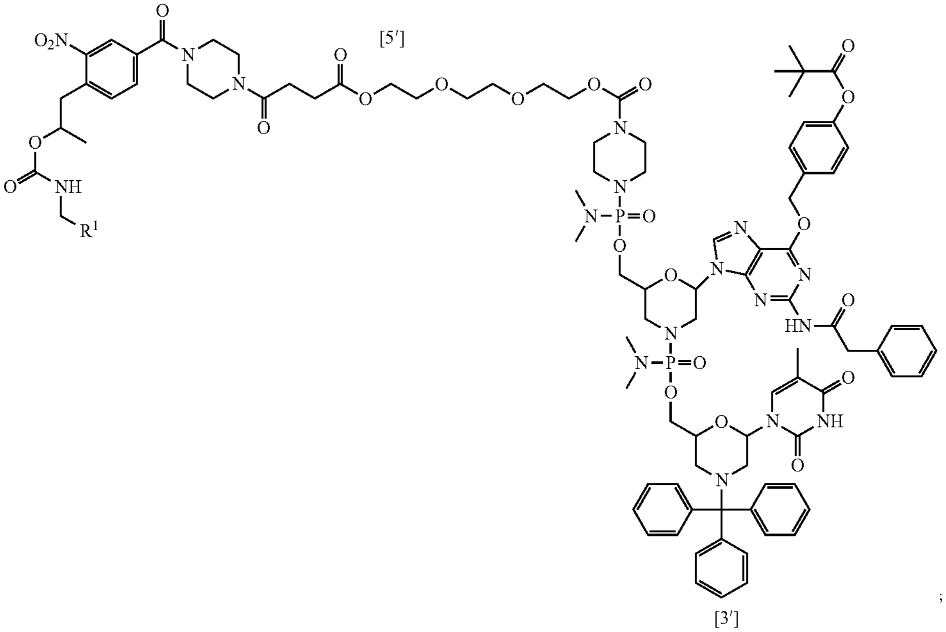
;

wherein $R^1$ is a support-medium;

(g) performing 23 iterations of the sequential steps of:

(g1) contacting the product formed by the immediately prior step with a deblocking agent; and (g2) contacting the compound formed by the immediately prior step with a compound of Formula (VIII):

(VIII)

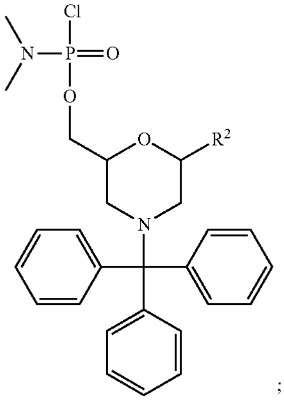

;

wherein $R^1$ is, independently for each compound of Formula (VIII), selected from the group consisting of:

(PC)

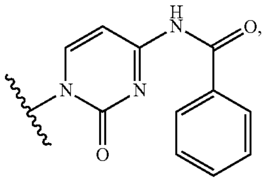

(DPG)

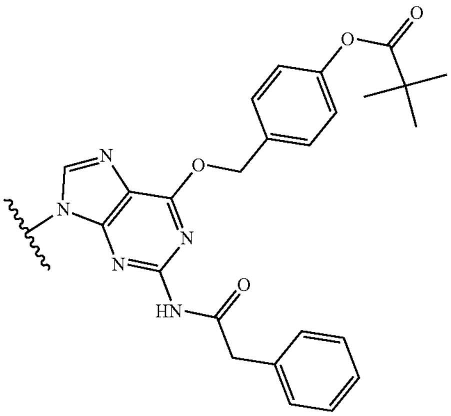

,

-continued (T)

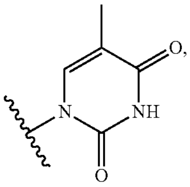

and (PA)

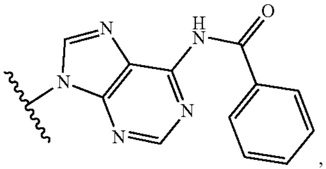

, wherein, for each iteration from 1 to 23, le is:

| Iteration No. | $R^2$ |
|---|---|
| 1 | T |
| 2 | DPG |
| 3 | PC |
| 4 | PC |
| 5 | T |
| 6 | PC |
| 7 | PC |
| 8 | DPG |
| 9 | DPG |
| 10 | T |
| 11 | T |
| 12 | PC |
| 13 | T |
| 14 | DPG |
| 15 | PA |
| 16 | PA |
| 17 | DPG |
| 18 | DPG |
| 19 | T |
| 20 | DPG |
| 21 | T |
| 22 | T |
| 23 | PC |

to form a compound of Formula (IX):
(IX)
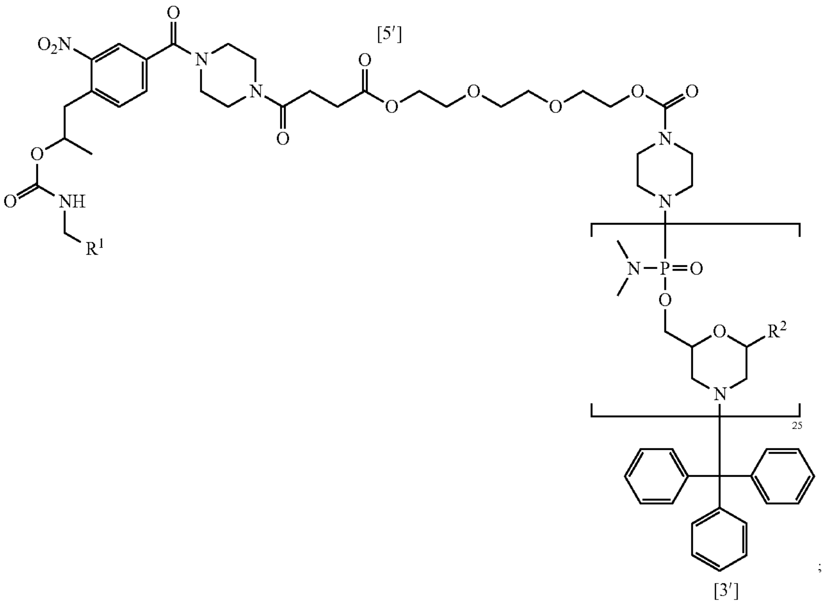
;
wherein $R^1$ is a support-medium,
wherein $R^2$ is, independently for each occurrence, selected from the group consisting of:
(PC)
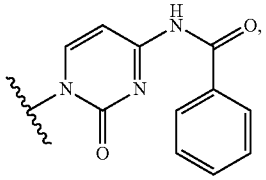
(DPG)
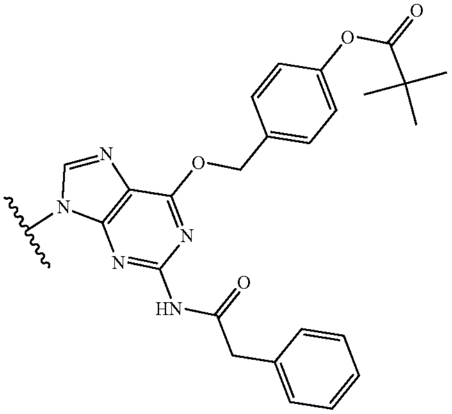
,
(T)
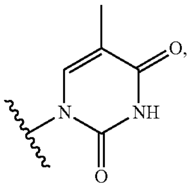
and
-continued
(PA)
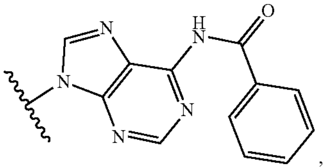
,
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

(h) contacting the compound of Formula (IX) with a deblocking agent to form a compound of Formula (X):
(X)
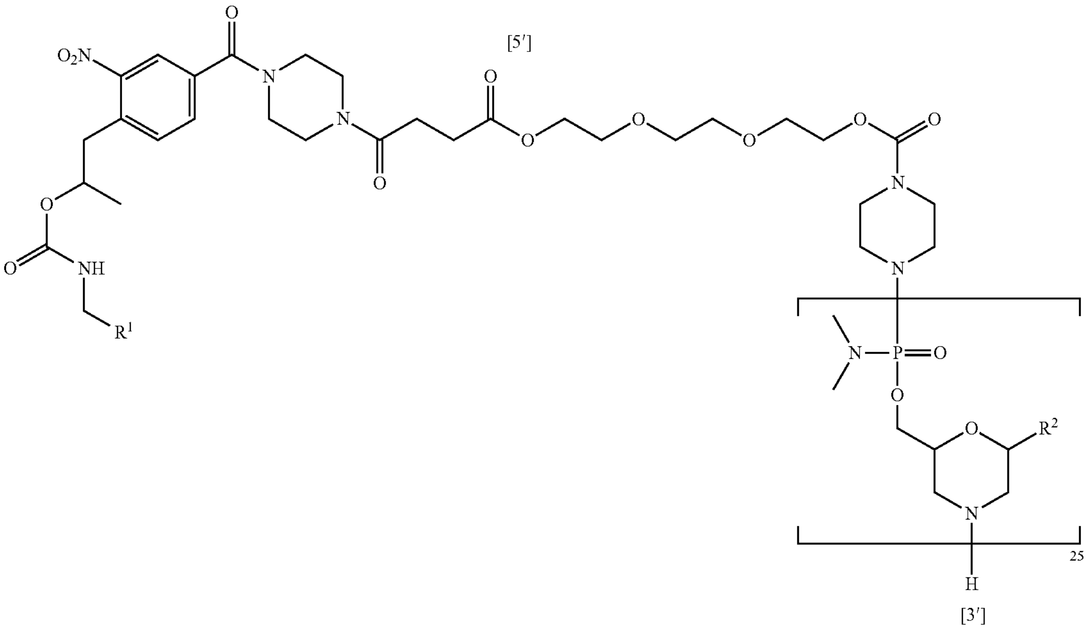
;
wherein $R^1$ is a support-medium,
wherein $R^1$ is, independently for each occurrence, selected from the group consisting of:
(PC)
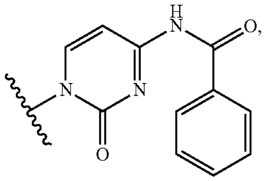
(DPG)
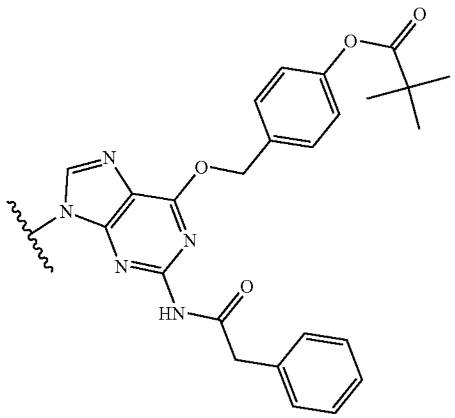
,
-continued
(T)
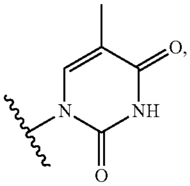
and
(PA)
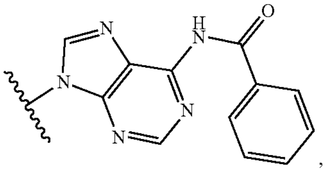
,
and
wherein $R^1$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |

-continued
| Position No. 5' to 3' | $R^2$ |
|---|---|
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |
(i) contacting the compound of Formula (X) with a cleaving agent to form a compound of Formula (XI):
(XI)
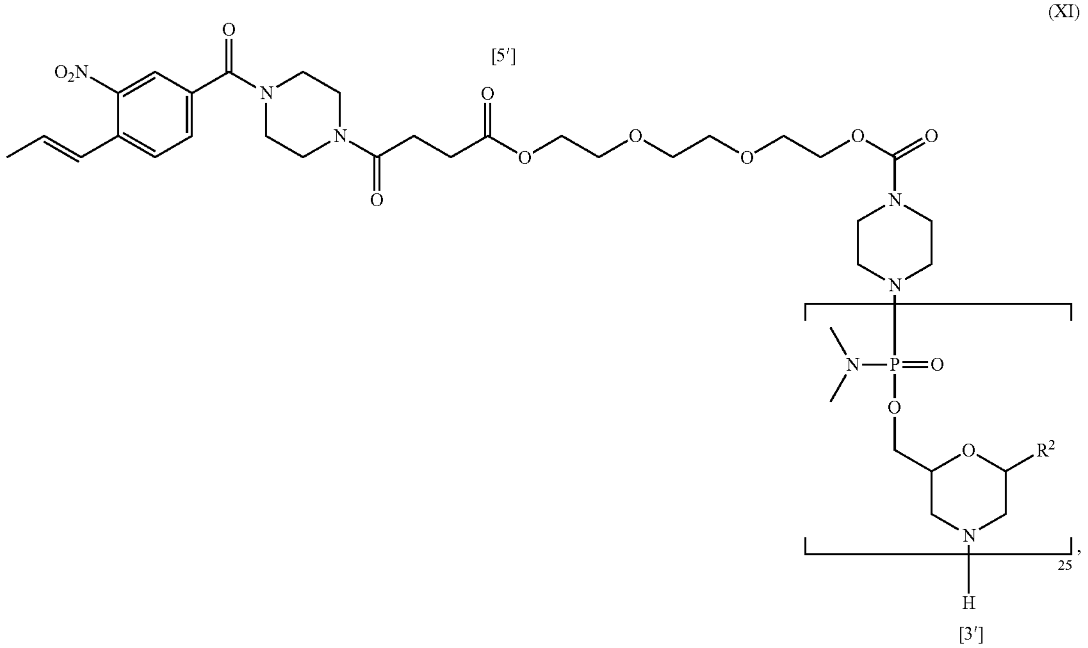

wherein $R^2$ is, independently for each occurrence, selected from the group consisting of:

(PC)

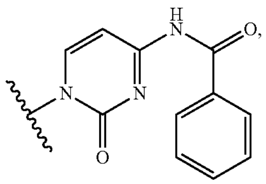

(DPG)

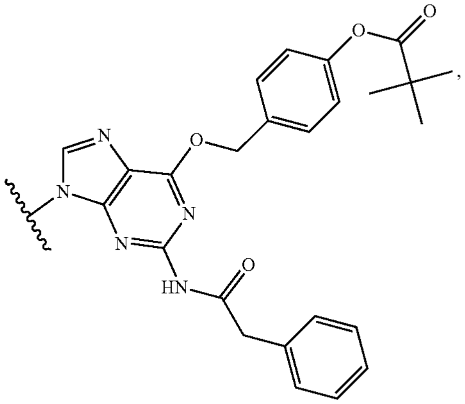

(T)

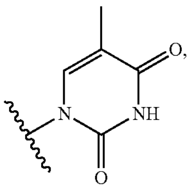

and (PA)

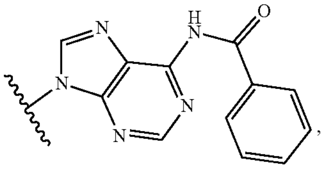

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |

-continued

| Position No. 5' to 3' | $R^2$ |
|---|---|
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

and (j) contacting the compound of Formula (XI) with a deprotecting agent to form the oligomeric compound of Formula (G).

In an embodiment, step (d), step (f), step (g2), or combinations thereof further comprises contacting the compound of Formula (IV), Formula (VI), or the compound formed by the immediately prior step, respectively, with a capping agent.

In certain embodiments, each of step (d), step (f) and step (g2) further comprises contacting the compound of Formula (IV), Formula (VI), or the compound formed by the immediately prior step, respectively, with a capping agent.

In another embodiment, each step is performed in the presence of at least one solvent.

In yet another embodiment, the deblocking agent used in each step is a solution comprising a halogenated acid.

In still another embodiment, the deblocking agent used in each step is cyanoacetic acid.

In another embodiment, the halogenated acid is selected from the group consisting of chloroacetic acid, dichloroacetic acid, trichloroacetic acid, fluoroacetic acid, difluoroacetic acid, and trifluoroacetic acid.

In yet another embodiment, the halogenated acid is trifluoroacetic acid.

In still another embodiment, at least one of steps (c), (e), and (g1) further comprise the step of contacting the deblocked compound of each step with a neutralization agent.

In another embodiment, each of steps (c), (e), and (g1) further comprise the step of contacting the deblocked compound of each step with a neutralization agent.

In yet another embodiment, the neutralization agent is in a solution comprising dichloromethane and isopropyl alcohol.

In still another embodiment, the neutralization agent is a monoalkyl, dialkyl, or trialkyl amine.

In another embodiment, the neutralization agent is N,N-diisopropylethylamine.

In yet another embodiment, the deblocking agent used in each step is a solution comprising 4-cyanopyridine, dichloromethane, trifluoroacetic acid, trifluoroethanol, and water.

In still another embodiment, the capping agent is in a solution comprising ethylmorpholine and methylpyrrolidinone.

In another embodiment, the capping agent is an acid anhydride.

In yet another embodiment, the acid anhydride is benzoic anhydride.

In still another embodiment, the compound of Formula (VIII), compound of Formula (DPG), and compound (F) are each, independently, in a solution comprising ethylmorpholine and dimethylimidazolidinone.

In another embodiment, the cleavage agent comprises dithiothreitol and 1,8-diazabicyclo[5.4.0]undec-7-ene.

In yet another embodiment, the cleavage agent is in a solution comprising N-methyl-2-pyrrolidone.

In still another embodiment, the deprotecting agent comprises $NH_3$.

In another embodiment, the deprotecting agent is in an aqueous solution.

In yet another embodiment, the support-medium comprises polystyrene with 1% crosslinked divinylbenzene.

In another embodiment, the compound of Formula (DPG) is of Formula (DPG1):

(DPG1)

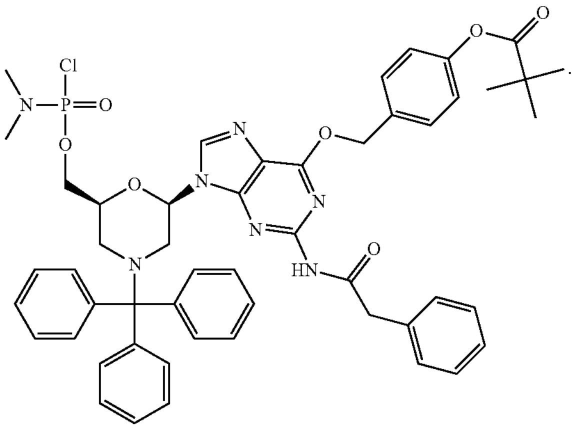

In another embodiment, the compound of Formula (V) is of Formula (Va):

(Va)

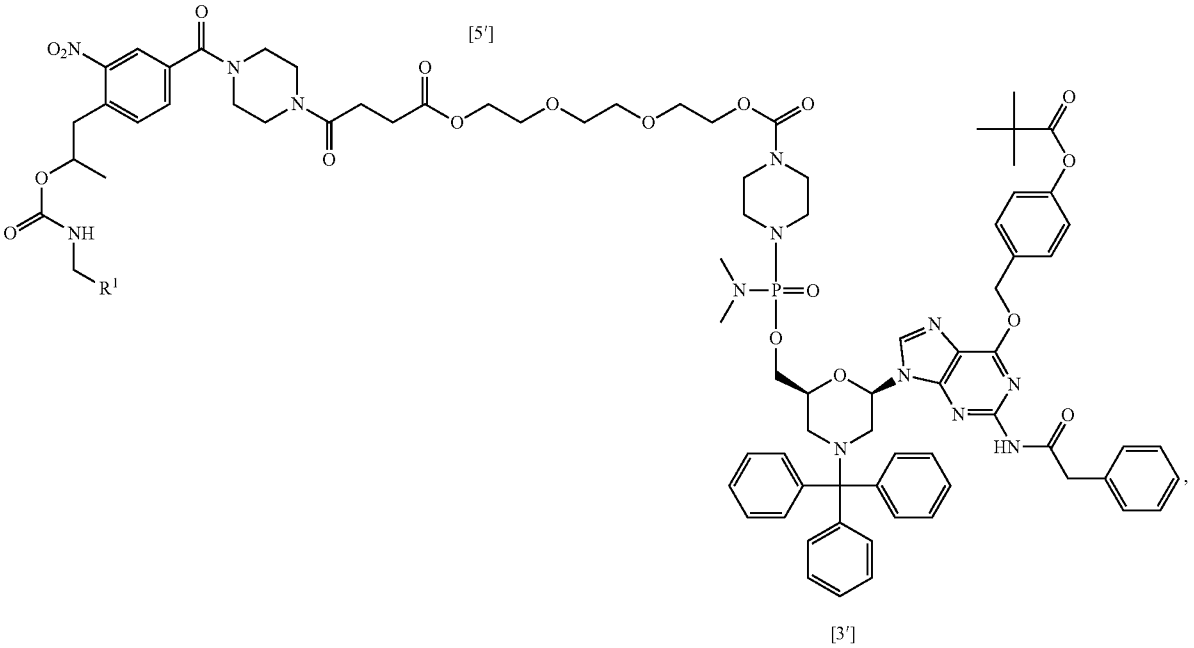

wherein $R^1$ is a support-medium.

In another embodiment, the compound of Formula (T) is of Formula (T1):
(T1)
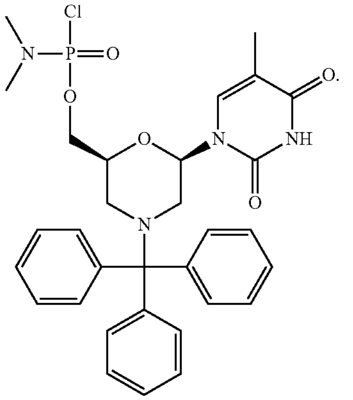
In another embodiment, the compound of Formula (VII) is of Formula (VIIa):
(VIIa)
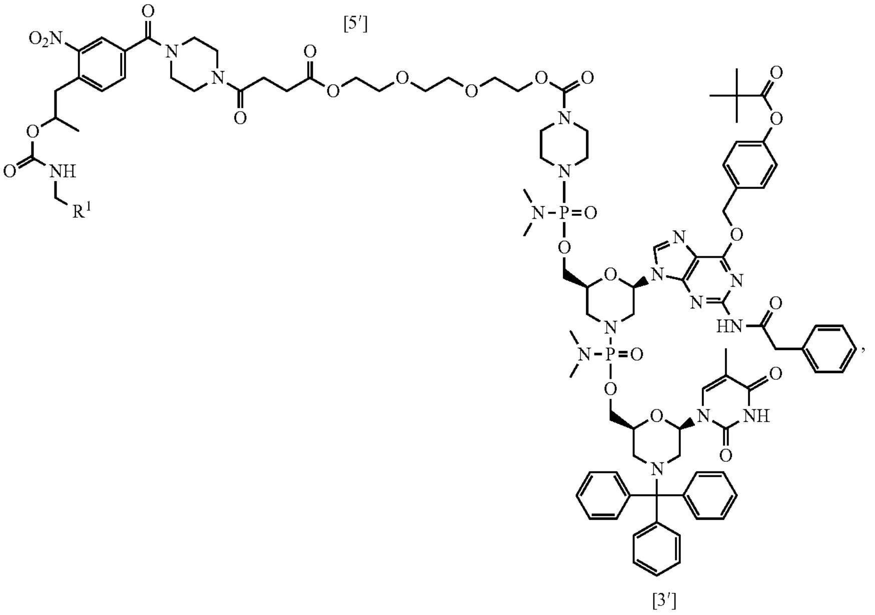
wherein $R^1$ is a support-medium.

In another embodiment, the compound of Formula (VIII) is of Formula (VIIIa):
(VIIIa)
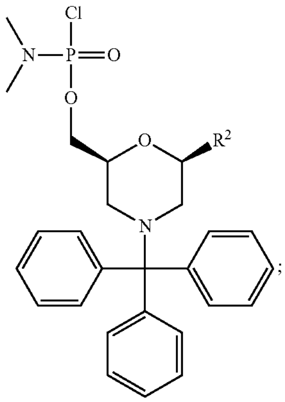
;
wherein $R^2$ is, independently for each compound of Formula (VIIIa), selected from the group consisting of:
(PC)
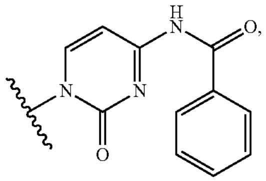
,
-continued
(DPG)
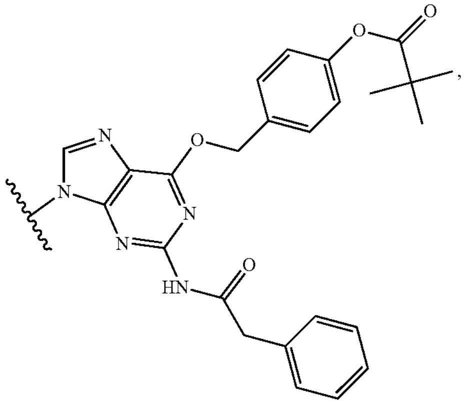
,
(T)
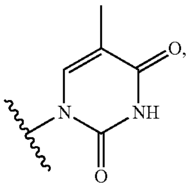
, and
(PA)
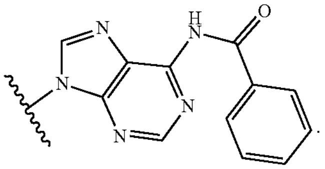
.
In another embodiment, the compound of Formula (IX) is of Formula (IXa):
(IXa)
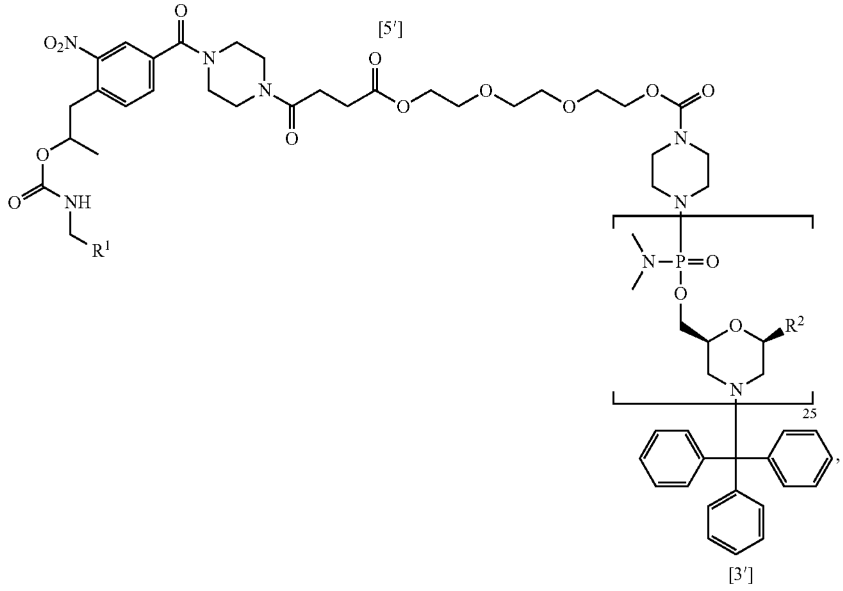
, or a pharmaceutically acceptable salt thereof, wherein $R^1$ is a support-medium, and $R^2$ is, independently at each occurrence, selected from the group consisting of:

(PC)

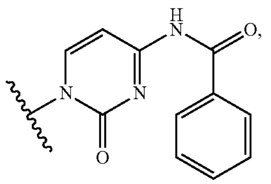

(DPG)

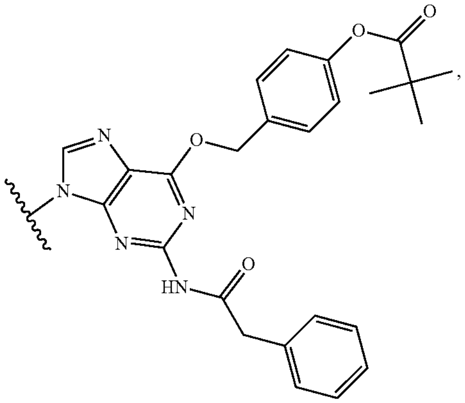

(T)

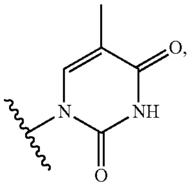

and

-continued (PA)

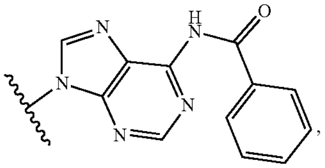

wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In another embodiment, the compound of Formula (X) is of Formula (Xa):

(Xa)

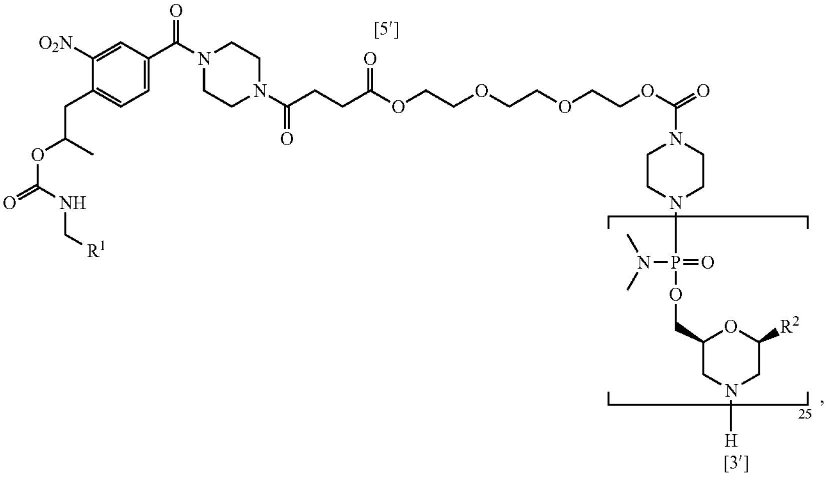

or a pharmaceutically acceptable salt thereof, wherein $R^1$ is a support-medium, and $R^2$ is, independently at each occurrence, selected from the group consisting of:

(PC)

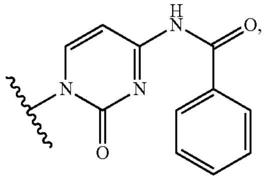

(DPG)

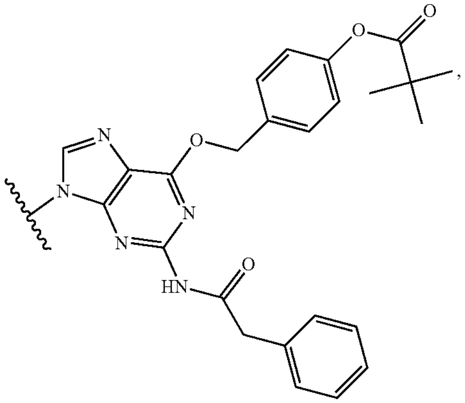

(T)

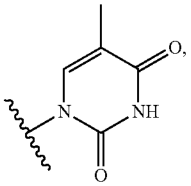

and

-continued (PA)

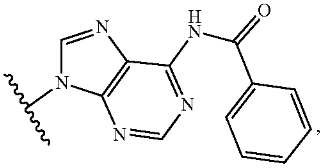

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In another embodiment, the compound of Formula (XI) is of Formula (XIa):

(XIa)

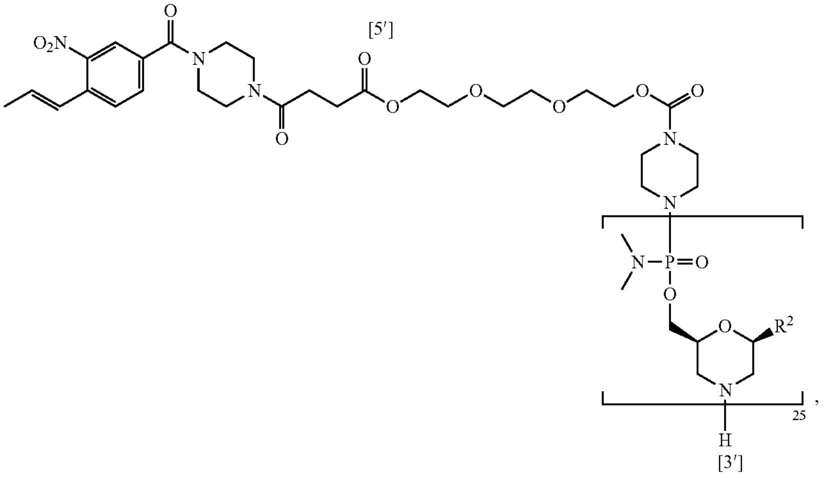

or a pharmaceutically acceptable salt thereof, wherein:

$R^2$ is, independently at each occurrence, selected from the group consisting of:

(PC)

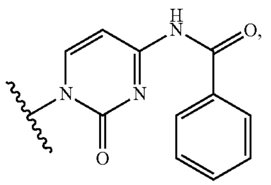

(DPG)

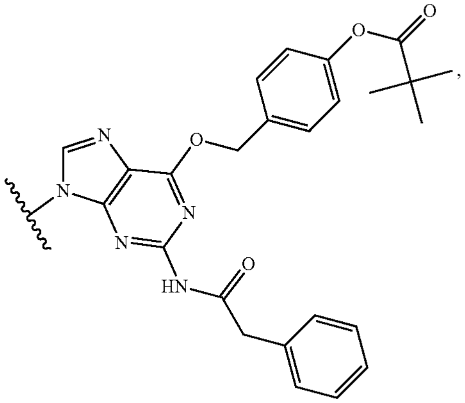

(T)

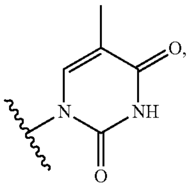

and (PA)

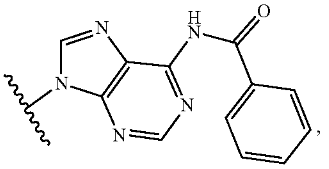

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In another embodiment, the compound of Formula (VI) is of Formula (VIa):

(VIa)

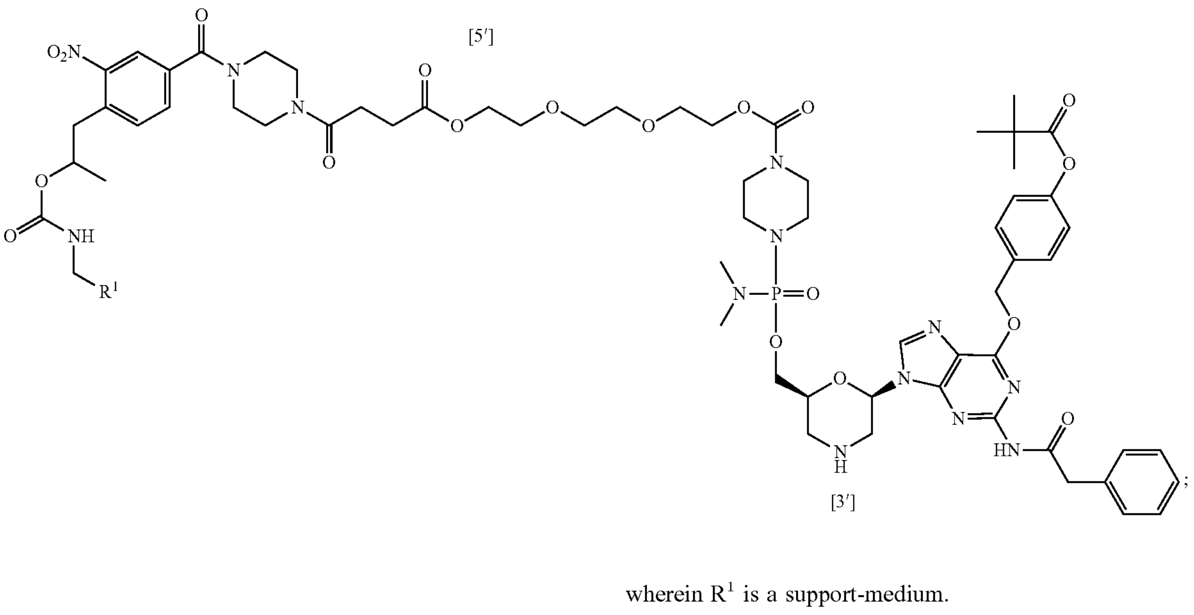

wherein $R^1$ is a support-medium.

In still another embodiment, the oligomeric compound of Formula (G) is an oligomeric compound of Formula (XII):
(XII)
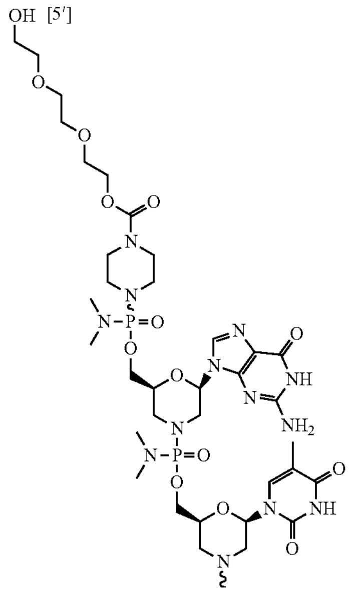
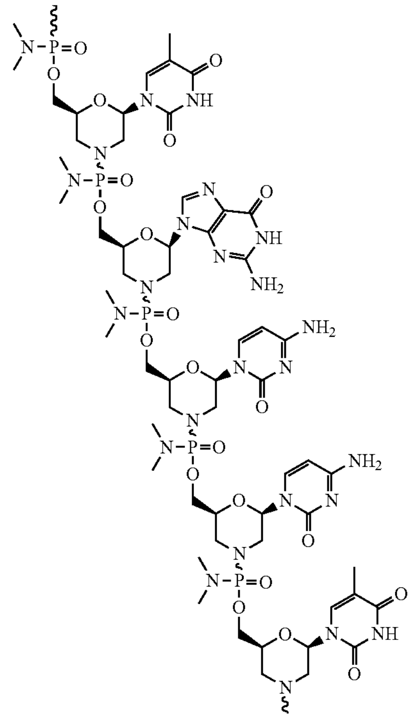
BREAK A
-continued
BREAK A
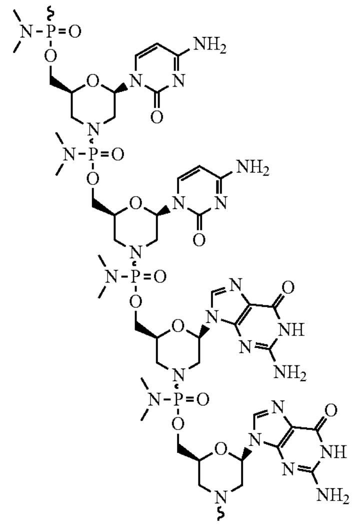
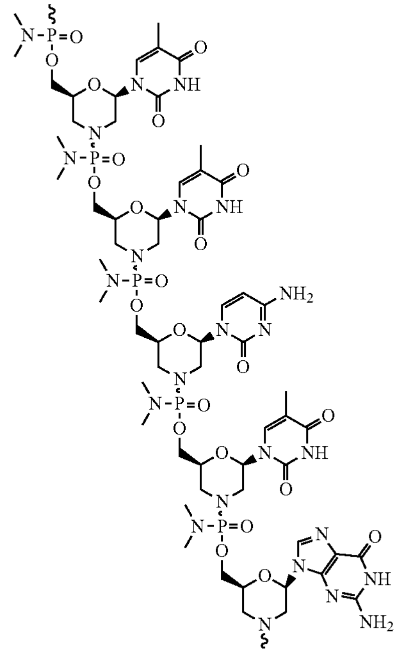
BREAK B -continued
BREAK B
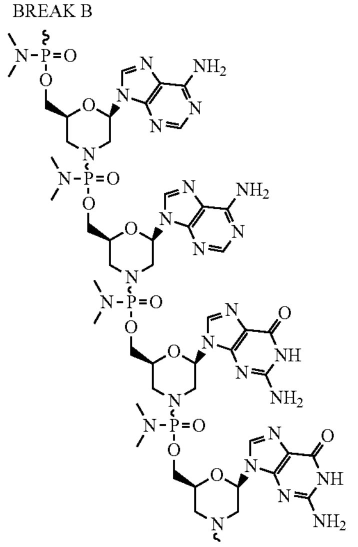
-continued
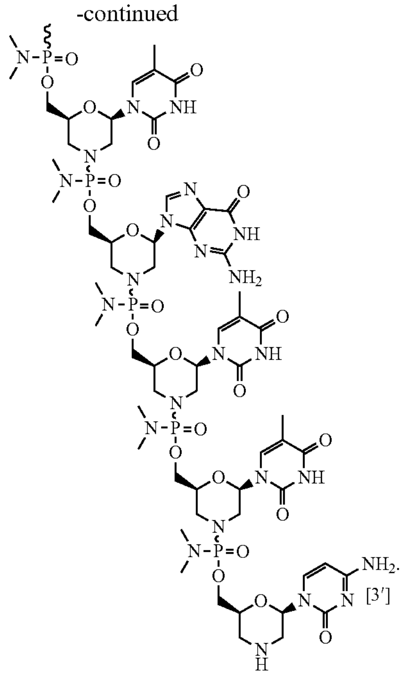
In another aspect, provided herein is a compound of Formula (A5):
(A5)
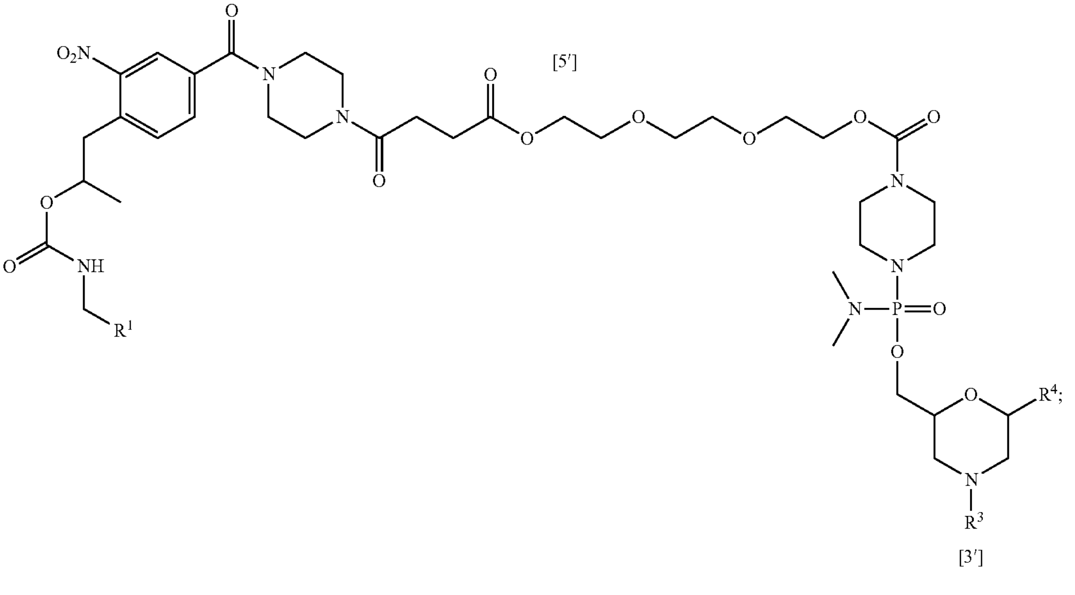

or a pharmaceutically acceptable salt thereof, wherein $R^1$ is a support-medium, $R^3$ is selected from the group consisting of trityl, monomethoxytrityl, dimethoxytrityl and trimethoxytrityl, and $R^4$ is selected from the group consisting of:
(PC)
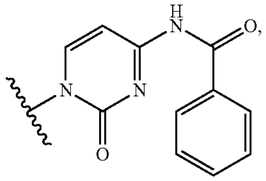
(DPG)
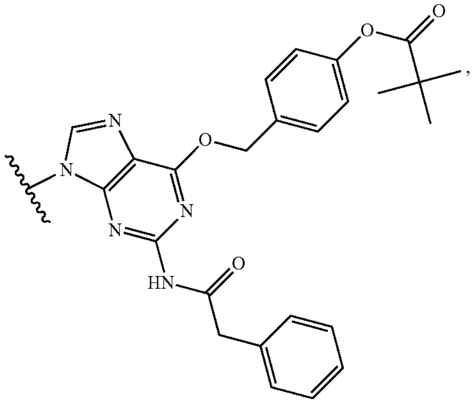
(T)
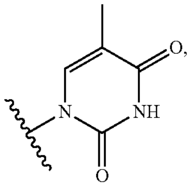
(PA)
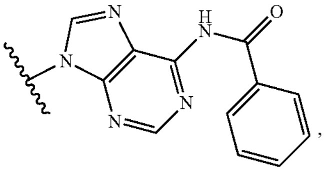
-continued
(P5mC)
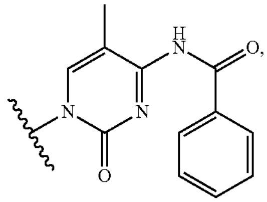
(U)
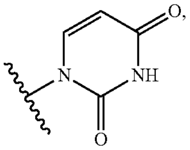
(I)
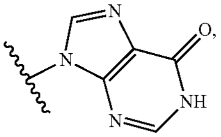
and
(PG)
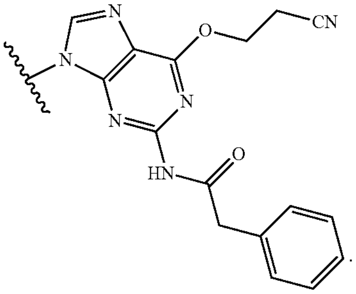
In some embodiments, the compound of Formula (A5) is of Formula (A5a):
(A5a)
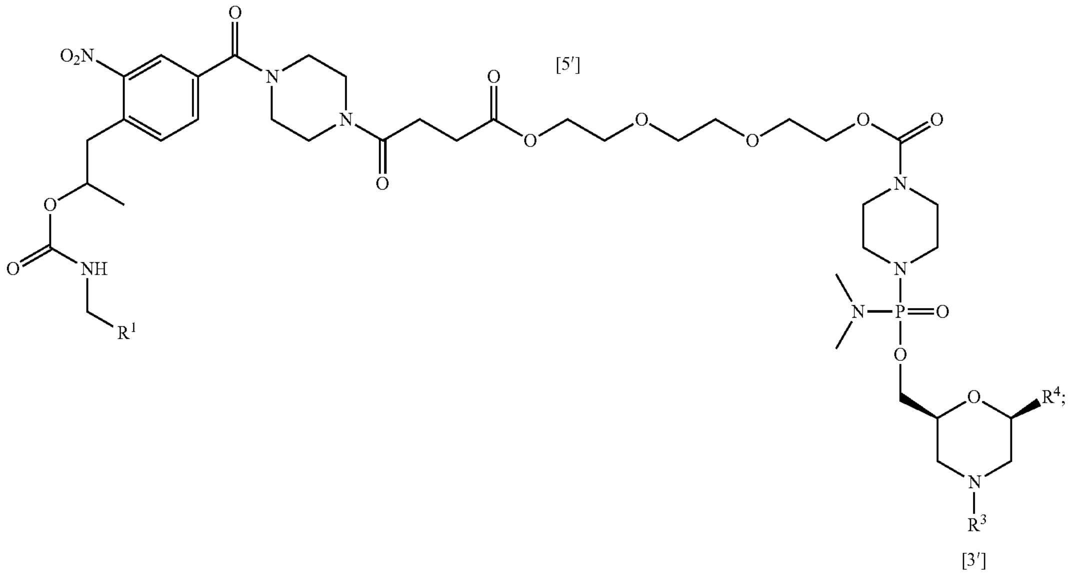

or a pharmaceutically acceptable salt thereof, wherein $R^1$ is a support-medium, $R^3$ is selected from the group consisting of trityl, monomethoxytrityl, dimethoxytrityl and trimethoxytrityl, and $R^4$ is selected from the group consisting of:
(PC)
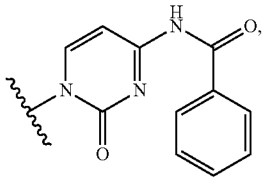
(DPG)
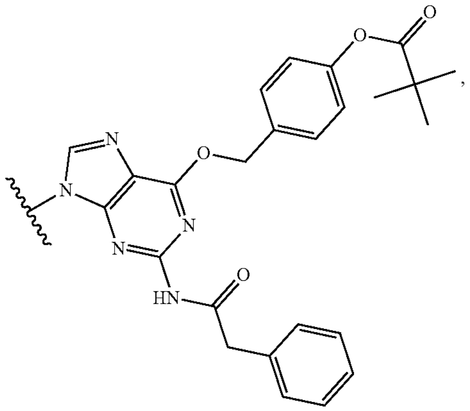
(T)
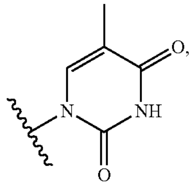
(PA)
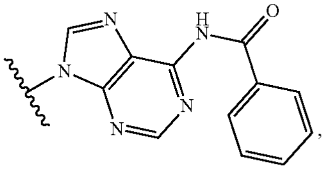
-continued
(P5mC)
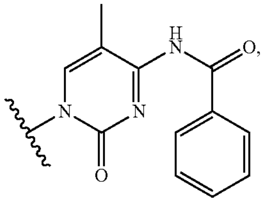
(U)
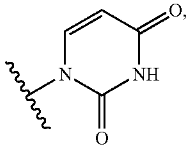
(I)
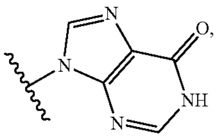
and
(PG)
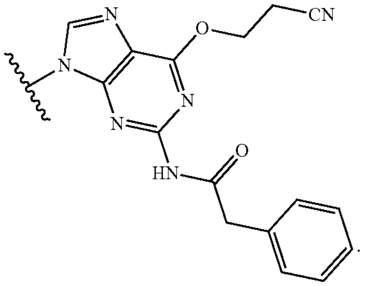

In another aspect, provided herein is a compound of Formula (V):
(V)
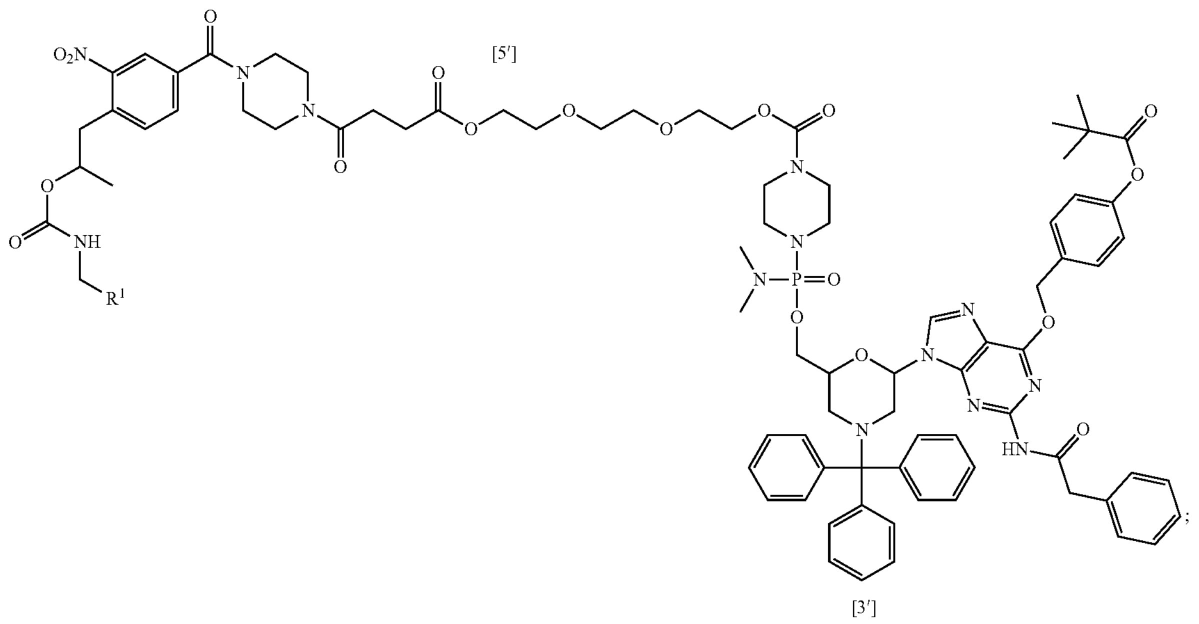
or a pharmaceutically acceptable salt thereof, wherein $R^1$ is a support-medium.
In some embodiments, the compound of Formula (V) is of Formula (Va):
(Va)
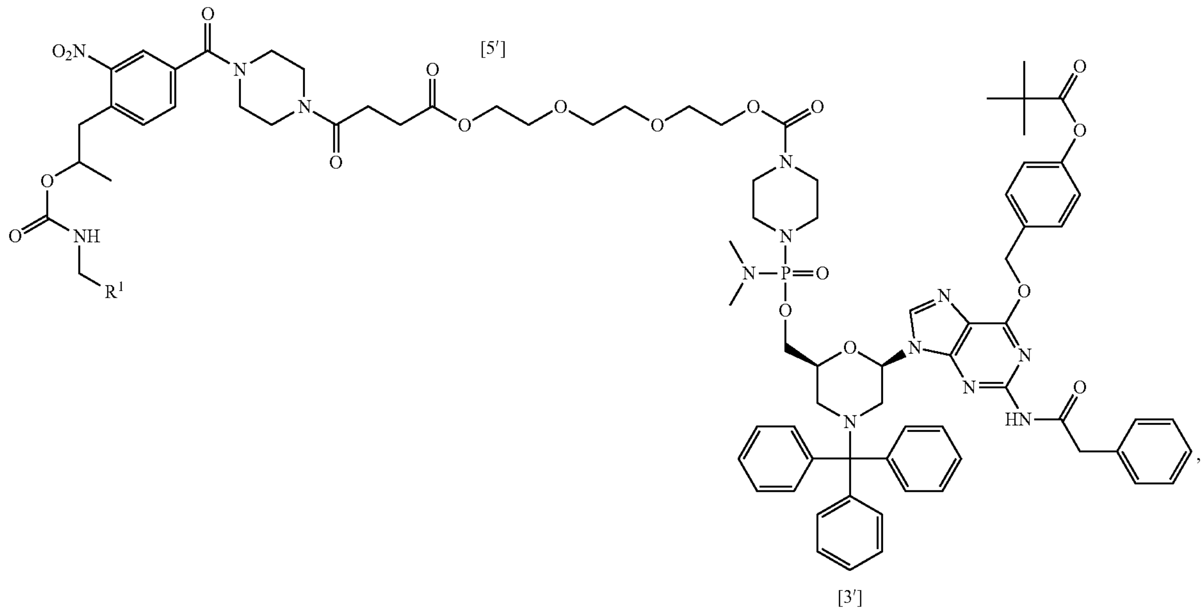
or a pharmaceutically acceptable salt thereof, wherein $R^1$ is a support-medium.

In another aspect, provided herein is a compound of Formula (VI):
(VI)
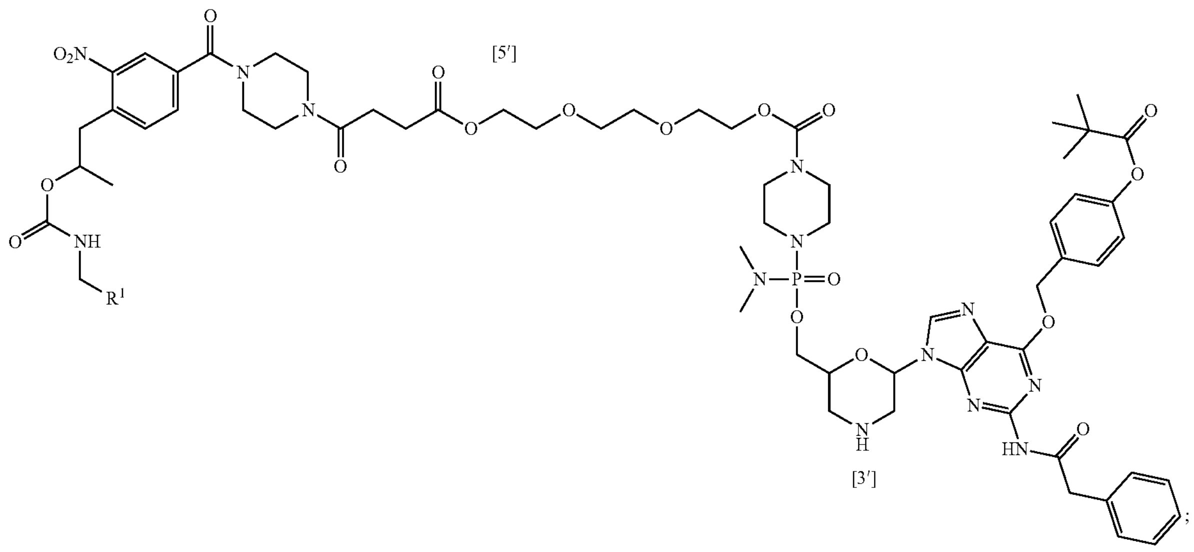
or a pharmaceutically acceptable salt thereof, wherein $R^1$ is a support-medium.
In some embodiments, the compound of Formula (VI) is of Formula (VIa):
(VIa)
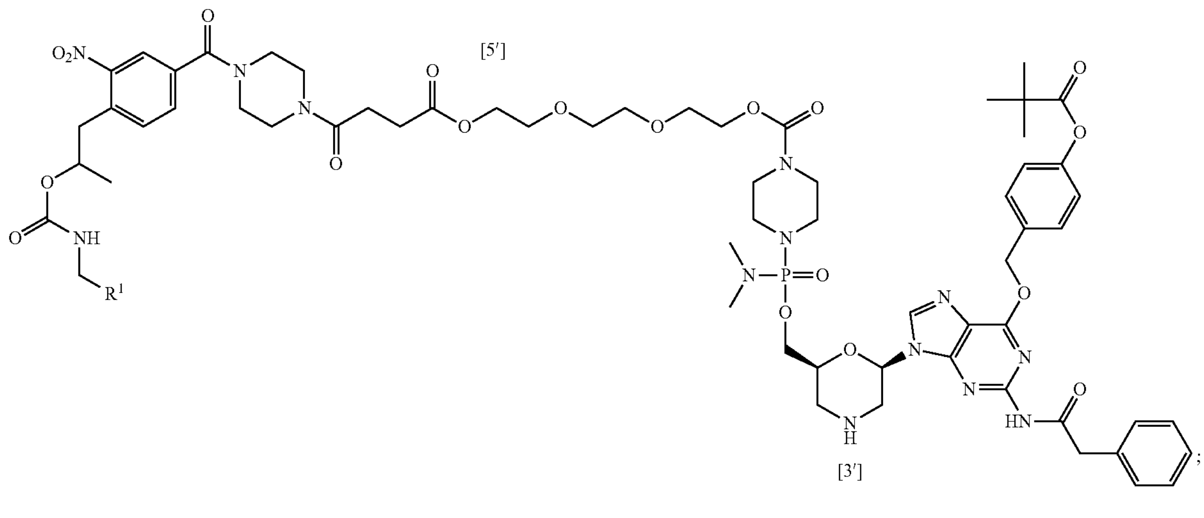
or a pharmaceutically acceptable salt thereof, wherein $R^1$ is a support-medium.

In another aspect, provided herein is a compound of Formula (VII):
(VII)
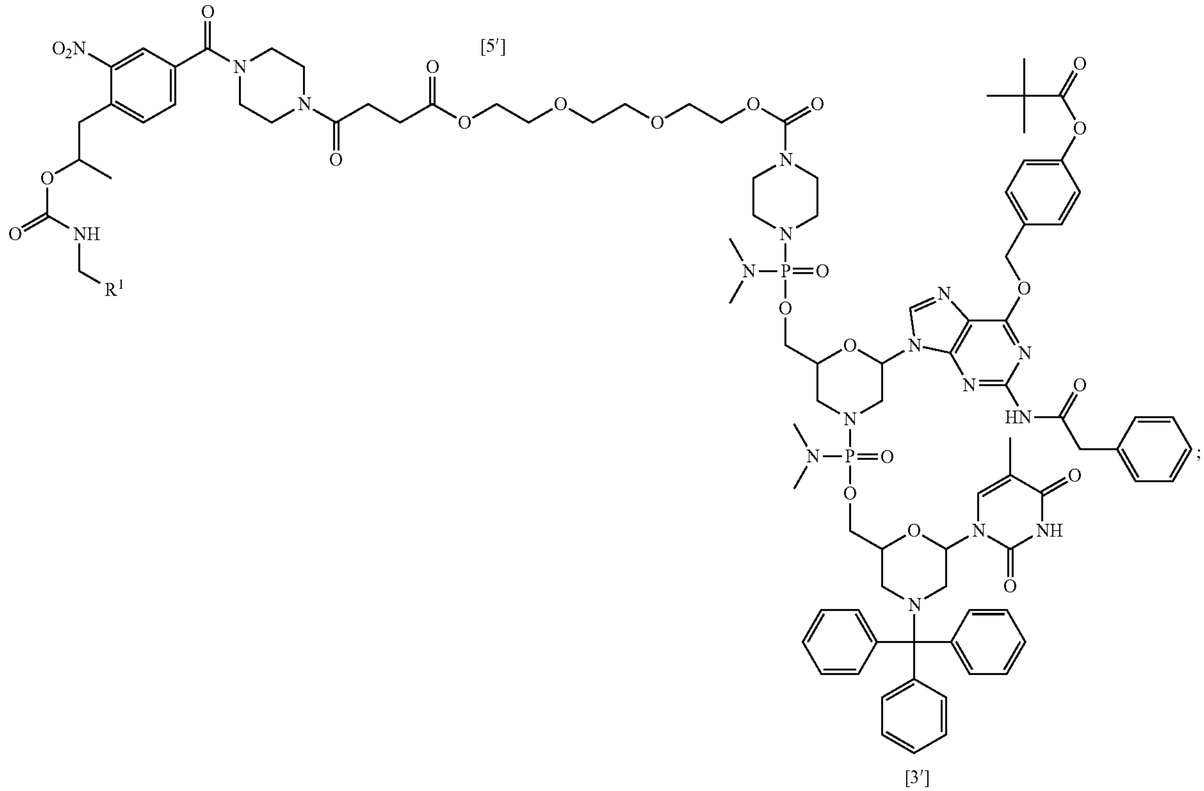
or a pharmaceutically acceptable salt thereof, wherein $R^1$ is a support-medium.

In some embodiments, the compound of Formula (VII) is of Formula (VIIa):
(VIIa)
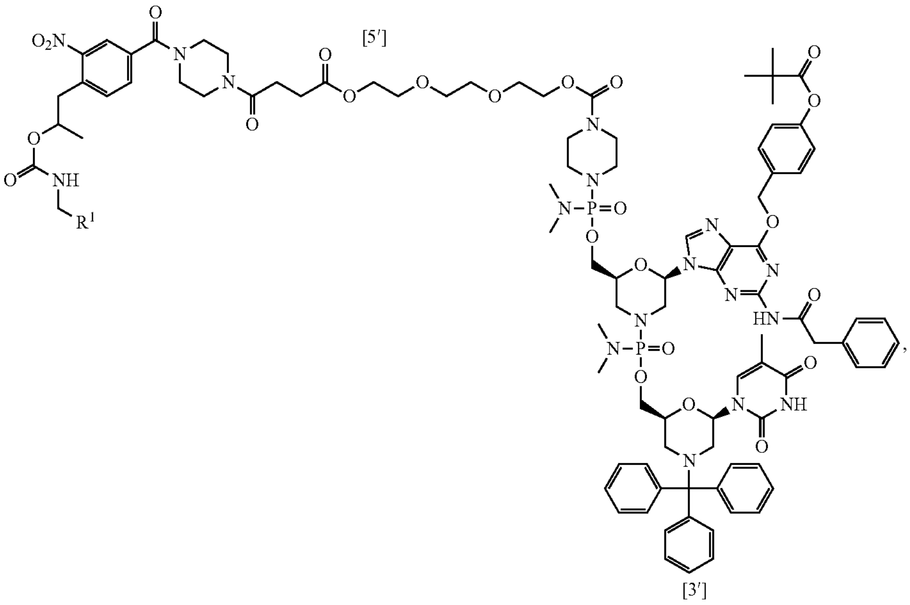
or a pharmaceutically acceptable salt thereof, wherein $R^1$ is a support-medium.
In another aspect, provided herein is a compound of Formula (IX):
(IX)
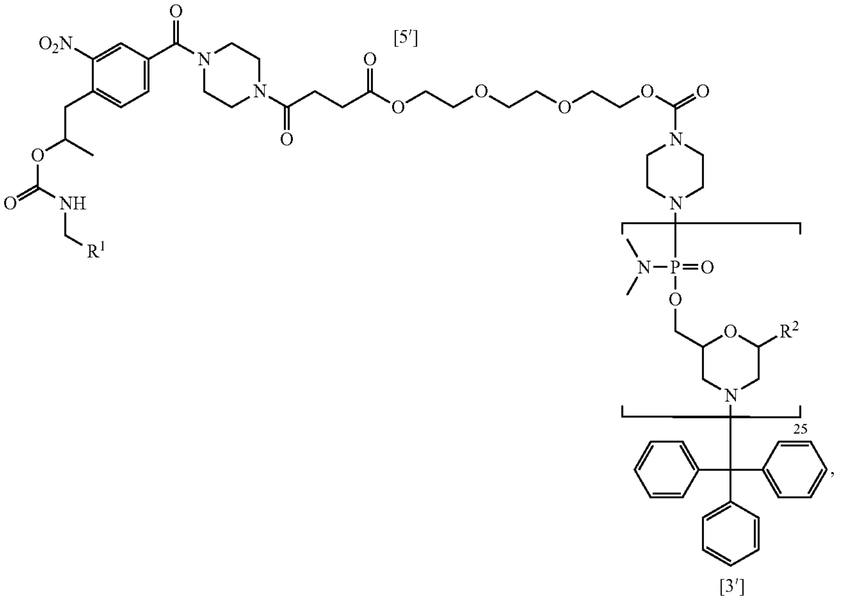

or a pharmaceutically acceptable salt thereof, wherein:

$R^1$ is a support-medium, and $R^2$ is, independently at each occurrence, selected from the group consisting of:

(PC)

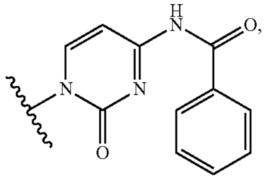

(DPG)

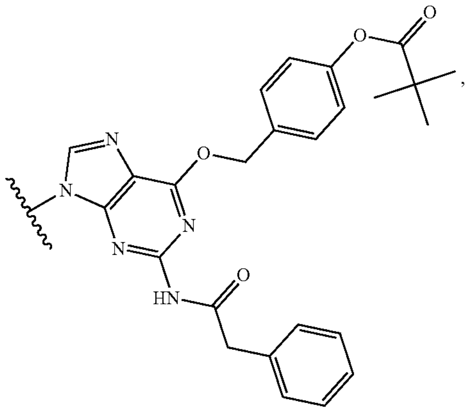

(T)

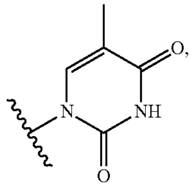

and

-continued (PA)

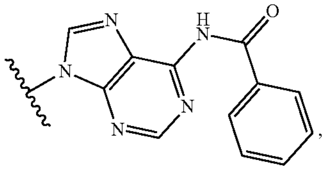

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In one embodiment, the compound of Formula (IX) is of Formula (IXa):

(IXa)

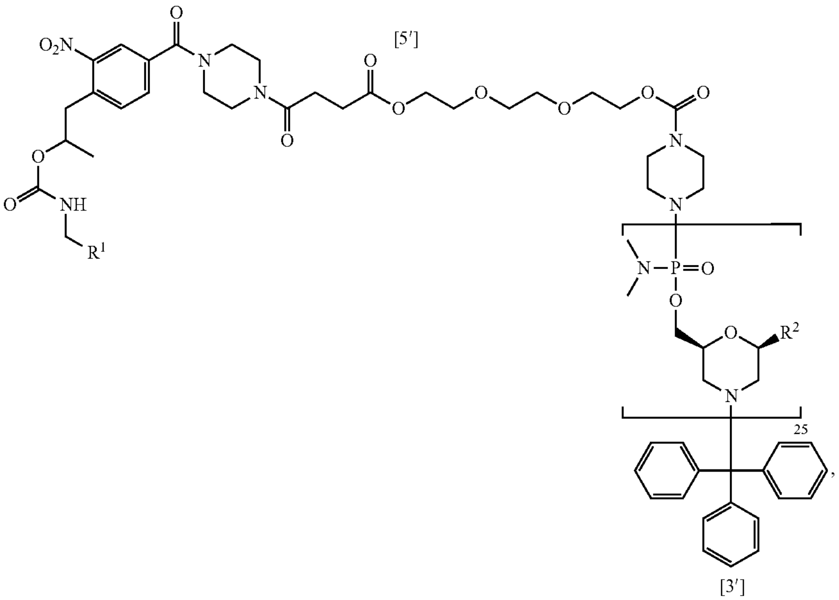

or a pharmaceutically acceptable salt thereof, wherein $R^1$ is a support-medium, and $R^2$ is, independently at each occurrence, selected from the group consisting of:

(PC)

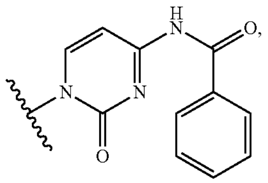

(DPG)

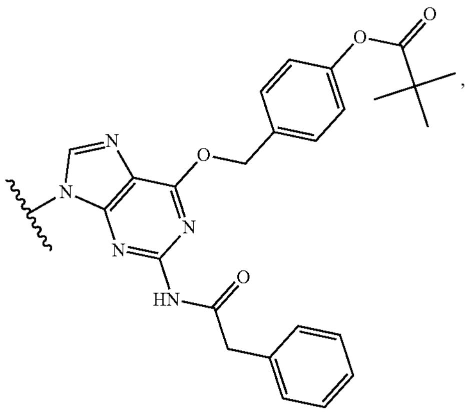

(T)

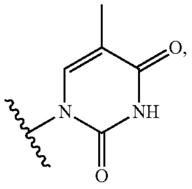

and

-continued (PA)

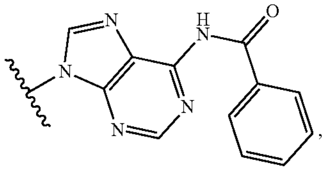

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In another aspect, provided herein is a compound of Formula (A9):

(A9)

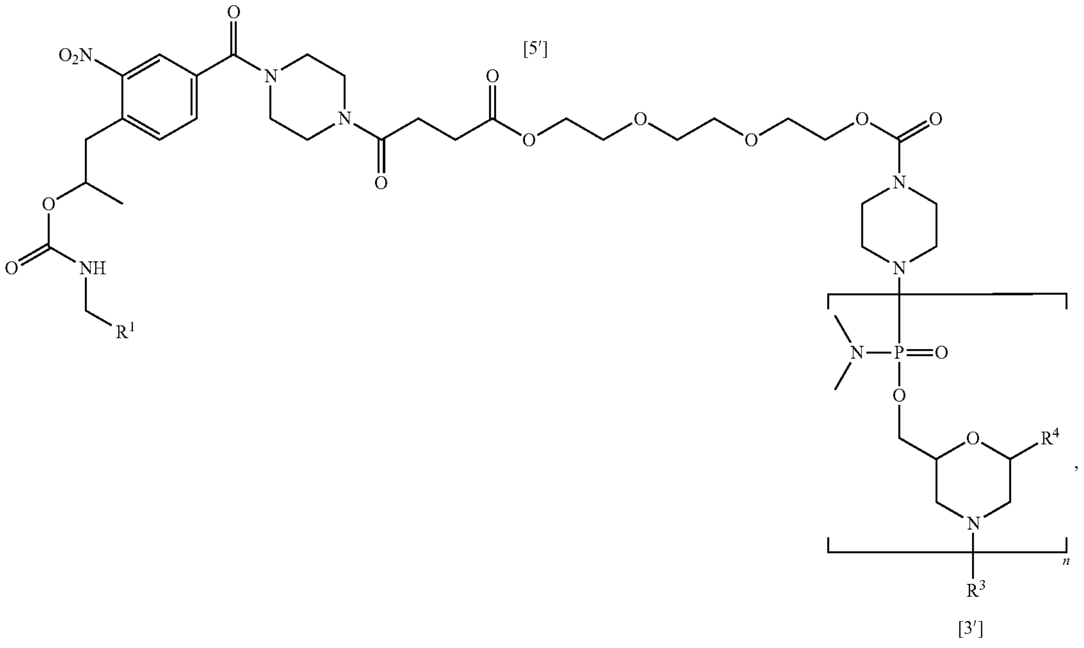

or a pharmaceutically acceptable salt thereof, wherein:
n is an integer from 10 to 40;
$R^1$ is a support-medium;
$R^3$ is selected from the group consisting of trityl, monomethoxytrityl, dimethoxytrityl and trimethoxytrityl; and
$R^4$ is, independently at each occurrence, selected from the group consisting of:
(PC)
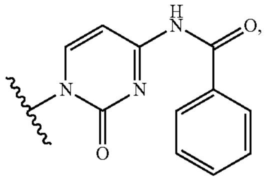
(DPG)
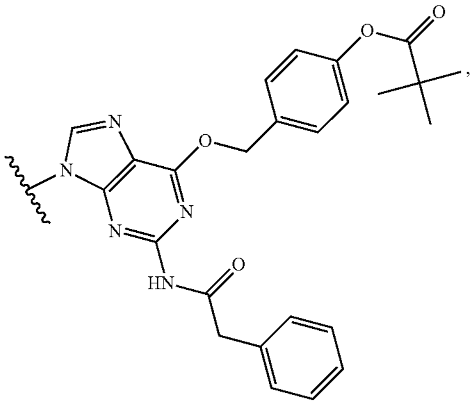
(T)
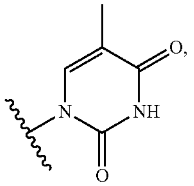
(PA)
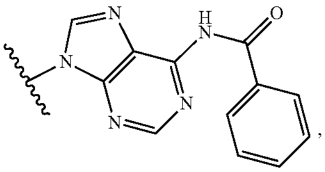
-continued
(P5mC)
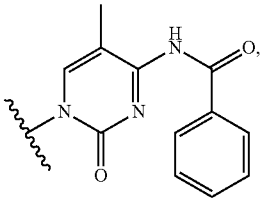
(U)
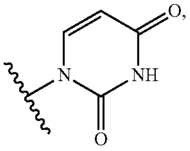
(I)
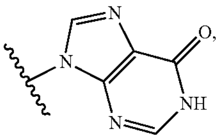
and
(PG)
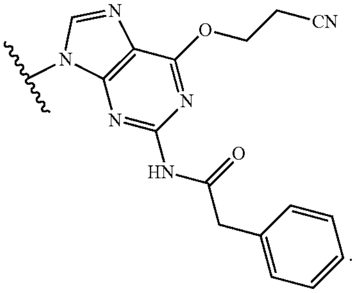

In one embodiment, the compound of Formula (A9) is of Formula (A9a):

(A9a)

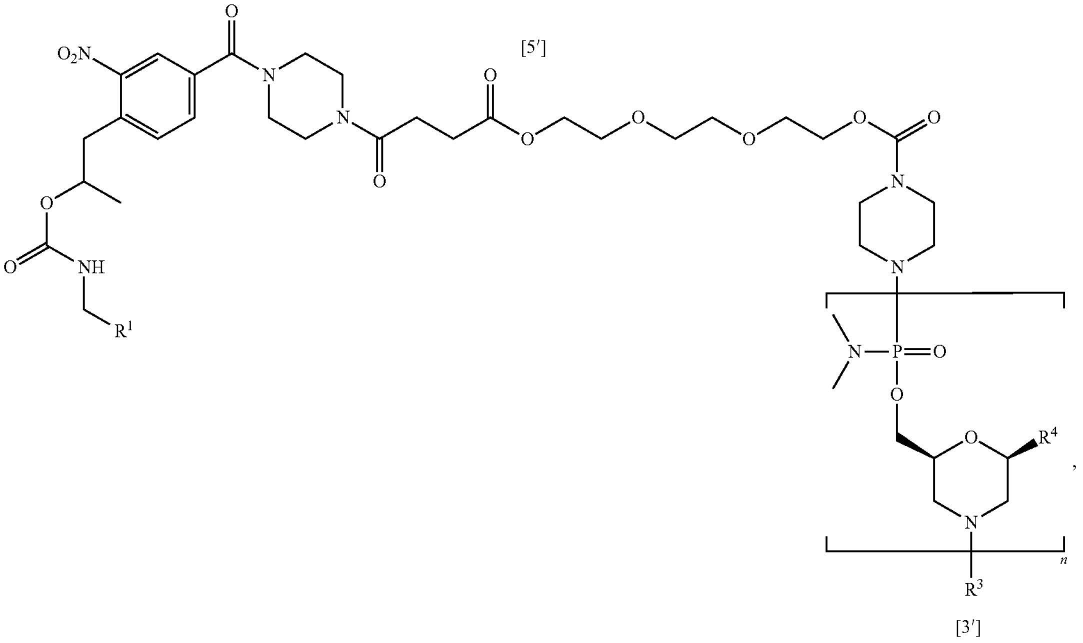

or a pharmaceutically acceptable salt thereof, wherein:

n is an integer from 10 to 40;

$R^1$ is a support-medium;

$R^3$ is selected from the group consisting of trityl, monomethoxytrityl, dimethoxytrityl and trimethoxytrityl; and $R^4$ is, independently at each occurrence, selected from the group consisting of:

(PC)

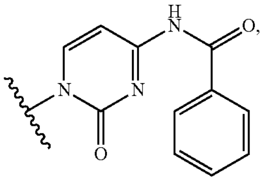

(DPG)

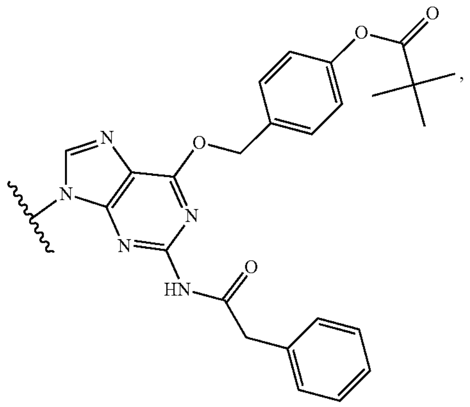

-continued (T)

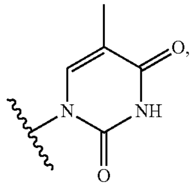

(PA)

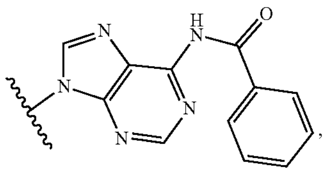

(P5mC)

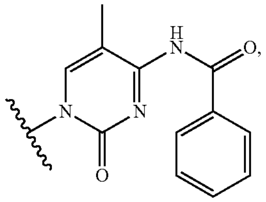

(U)

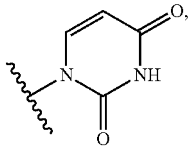

-continued
(I)
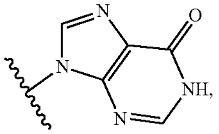
and
(PG)
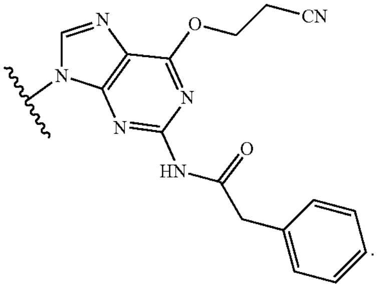
In another aspect, provided herein is a compound of Formula (X):
(X)
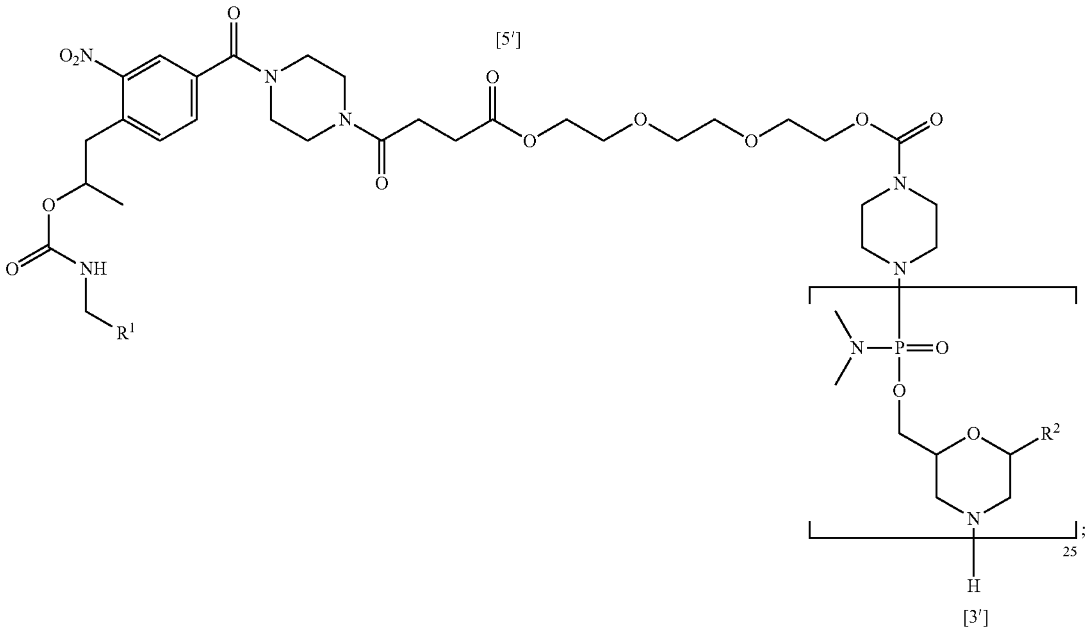
or a pharmaceutically acceptable salt thereof, wherein
$R^1$ is a support-medium, and
$R^2$ is, independently at each occurrence, selected from the group consisting of:
(PC)
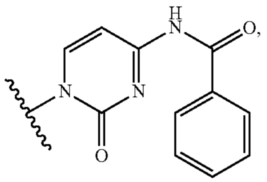
-continued
(DPG)
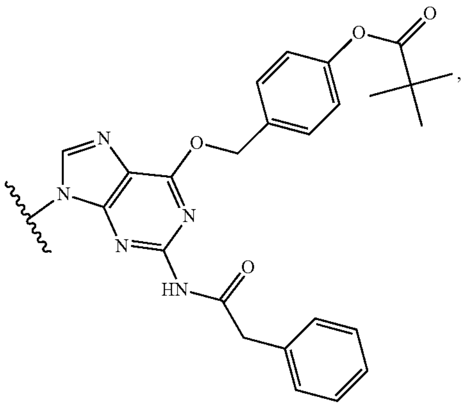

-continued
(T)
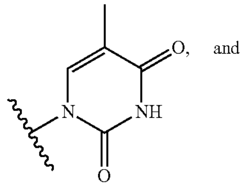
(PA)
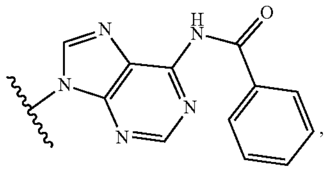
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |
In one embodiment, the compound of Formula (X) is of Formula (Xa):
(Xa)
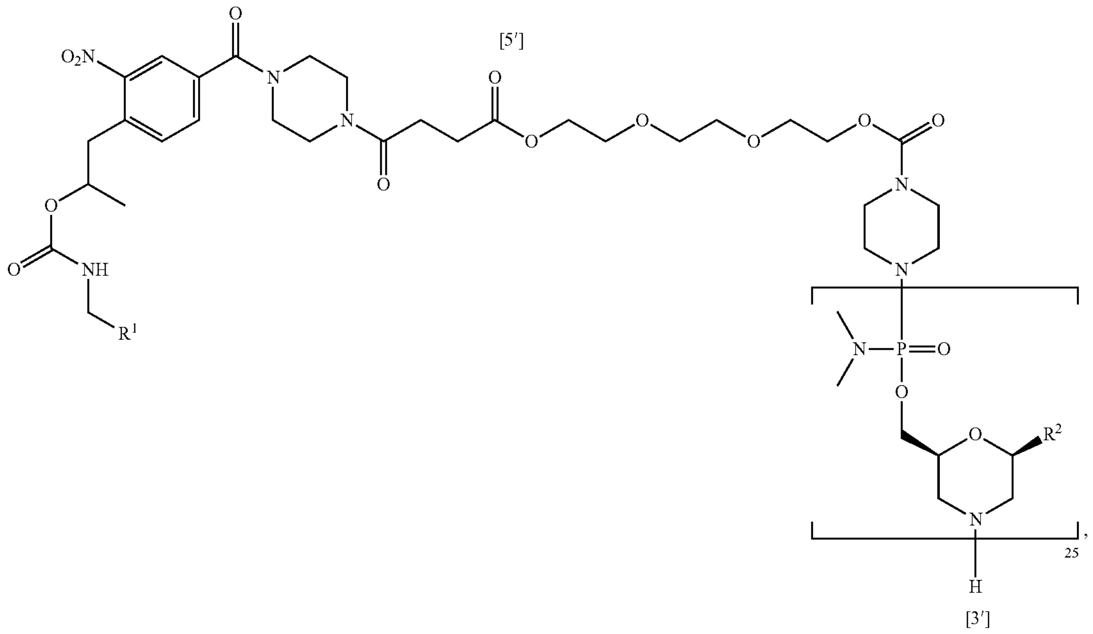

or a pharmaceutically acceptable salt thereof, wherein $R^1$ is a support-medium, and $R^2$ is, independently at each occurrence, selected from the group consisting of:

(PC)

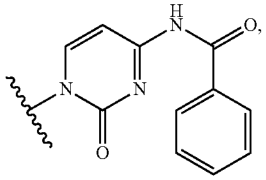

(DPG)

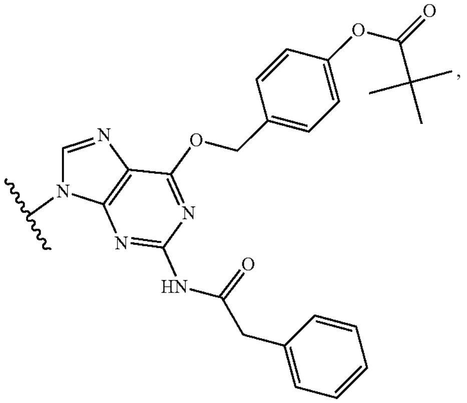

(T)

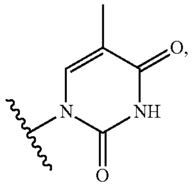

and

-continued (PA)

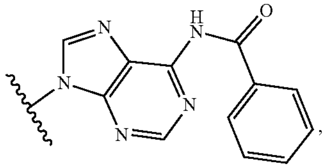

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In another aspect, provided herein is a compound of Formula (A10):

(A10)

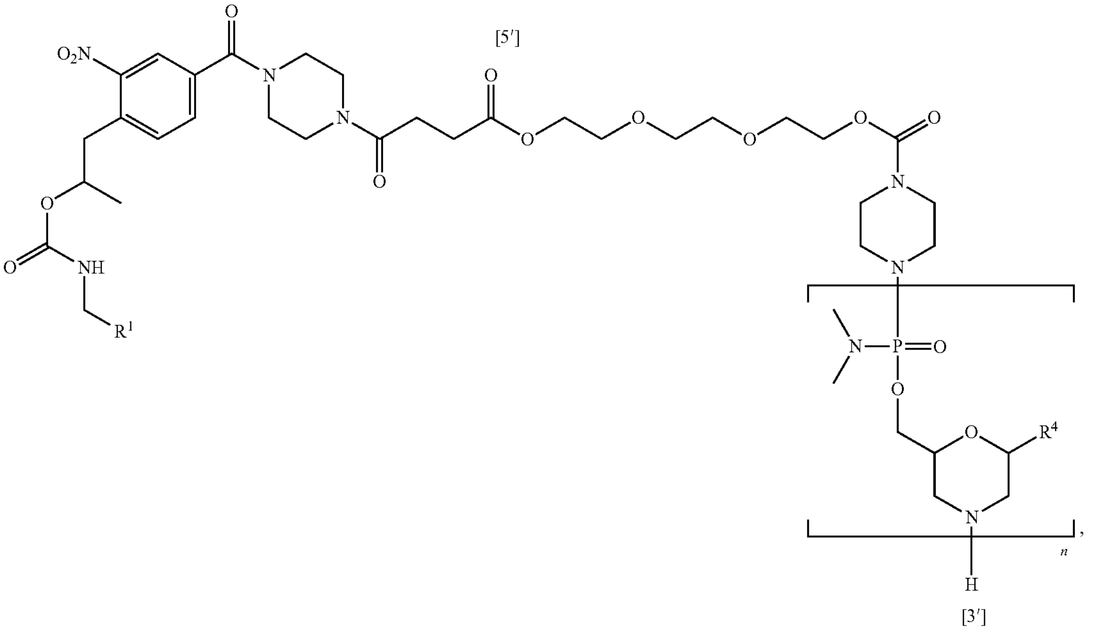

or a pharmaceutically acceptable salt thereof, wherein:
n is an integer from 10 to 40;
$R^1$ is a support-medium; and
$R^4$ is, independently at each occurrence, selected from the group consisting of:
(PC)
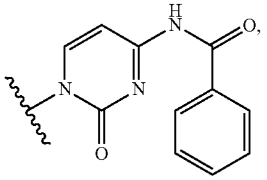
(DPG)
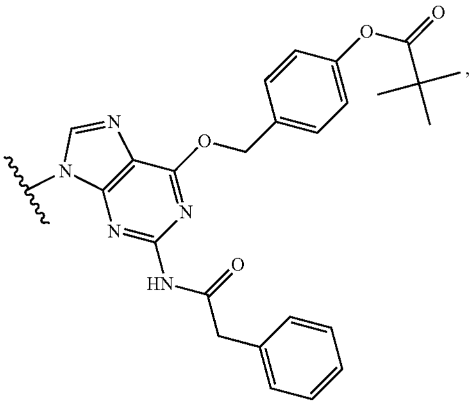
(T)
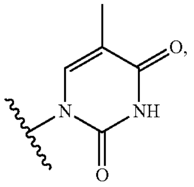
(PA)
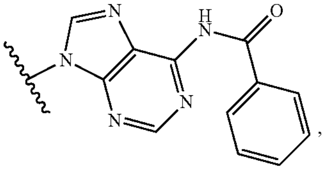
-continued
(P5mC)
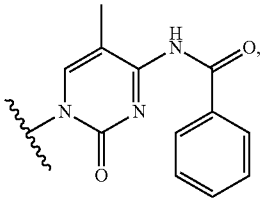
(U)
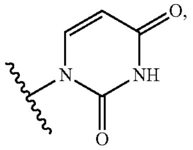
(I)
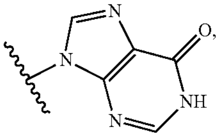
and
(PG)
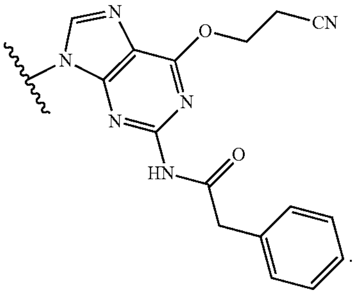

In one embodiment, the compound of Formula (A10) is of Formula (A10a):
(A10a)
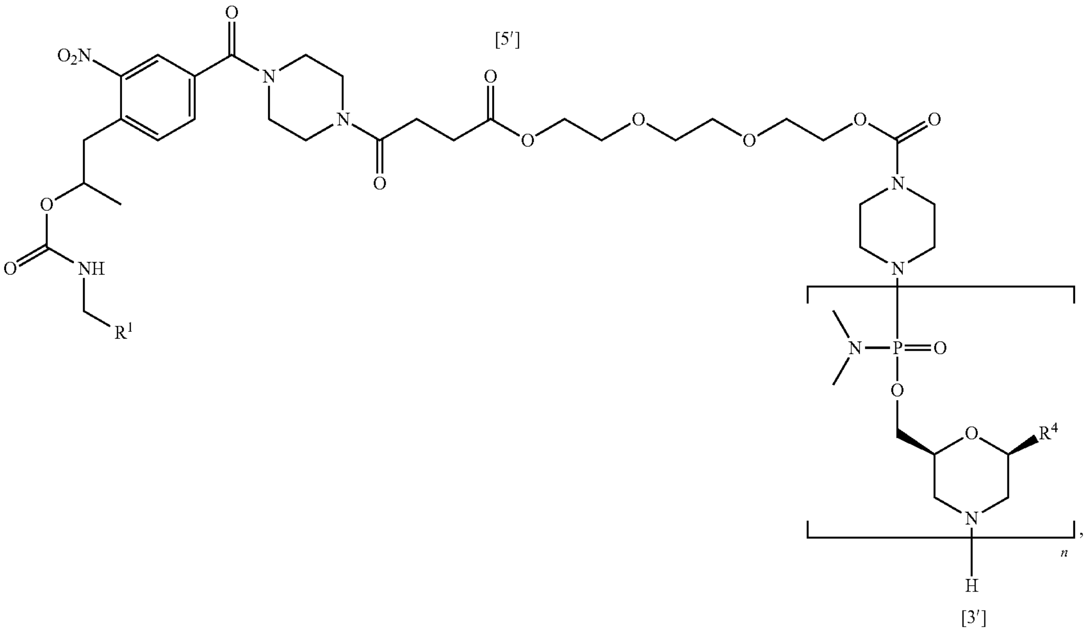
or a pharmaceutically acceptable salt thereof, wherein:
n is an integer from 10 to 40;
$R^1$ is a support-medium; and
$R^4$ is, independently at each occurrence, selected from the group consisting of:
(PC)
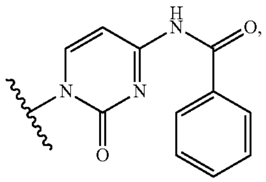
(DPG)
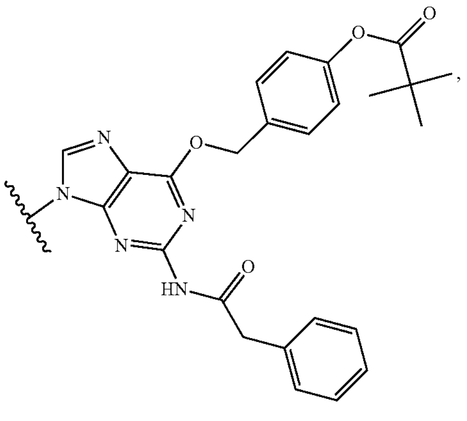
-continued
(T)
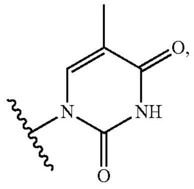
(PA)
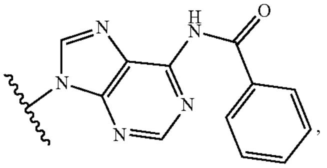
(P5mC)
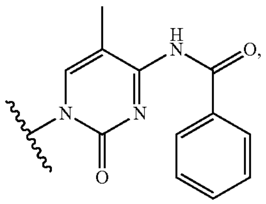
(U)
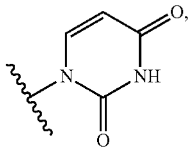

-continued
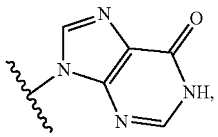
(I)
and
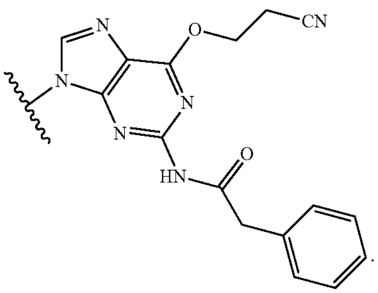
(PG)
In another embodiment of these compounds, the support-medium comprises polystyrene with 1% crosslinked divinylbenzene.
In another aspect, provided herein is a compound of Formula (XI):
(XI)
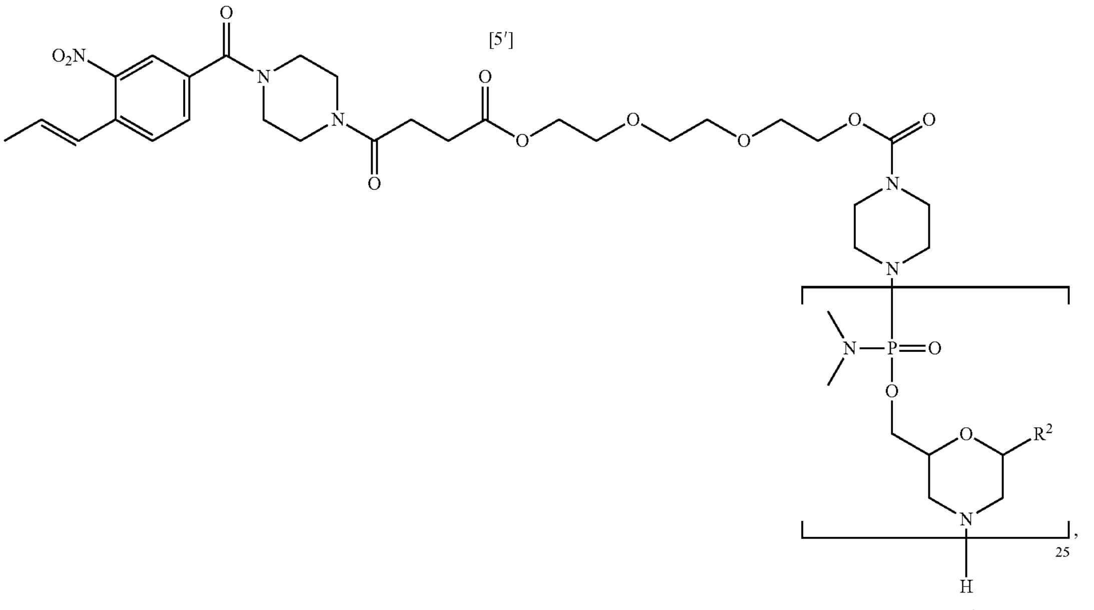
[5′] [3′]

or a pharmaceutically acceptable salt thereof, wherein:
$R^2$ is, independently at each occurrence, selected from the group consisting of:
(PC)
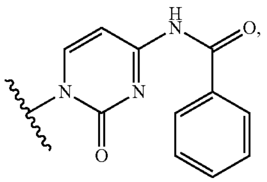
(DPG)
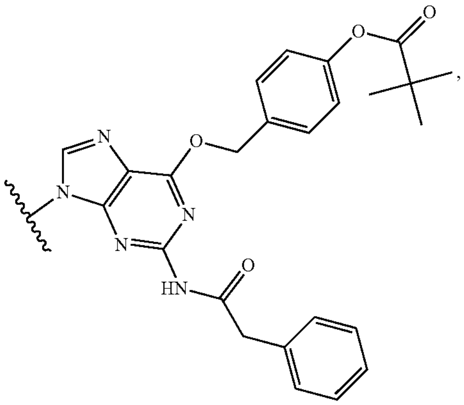
-continued
(T)
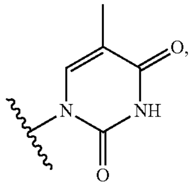
and
(PA)
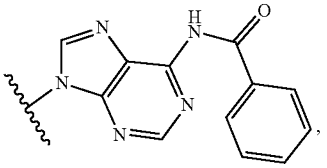
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

In one embodiment, the compound of Formula (XI) is of Formula (XIa):
(XIa)
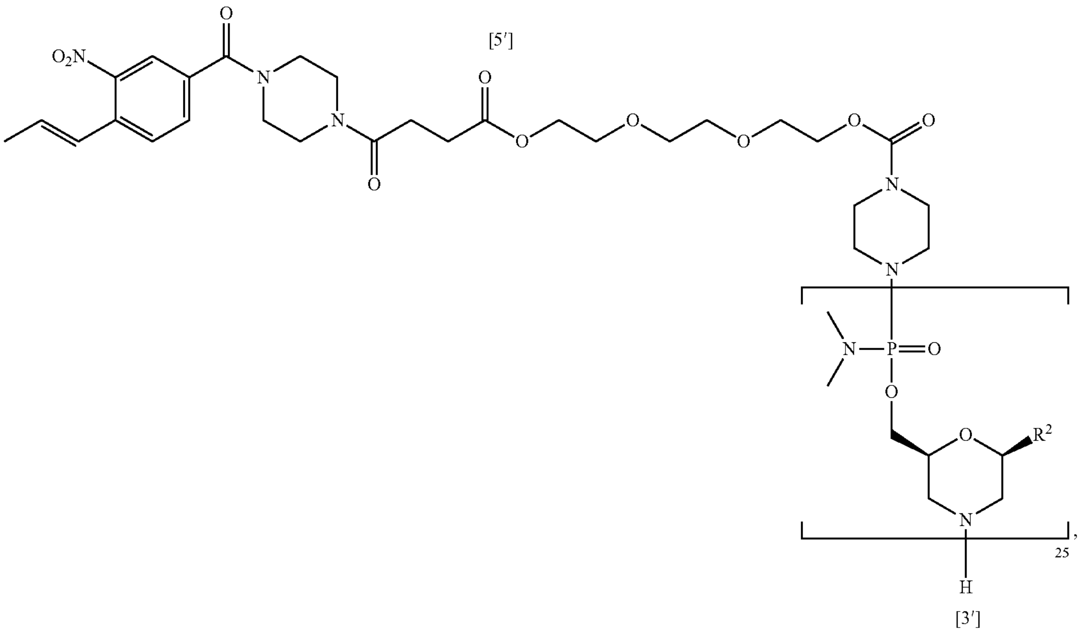
or a pharmaceutically acceptable salt thereof, wherein
$R^2$ is, independently at each occurrence, selected from the group consisting of:
(PC)
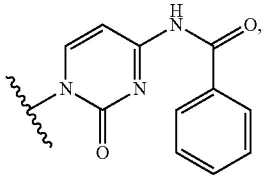
(DPG)
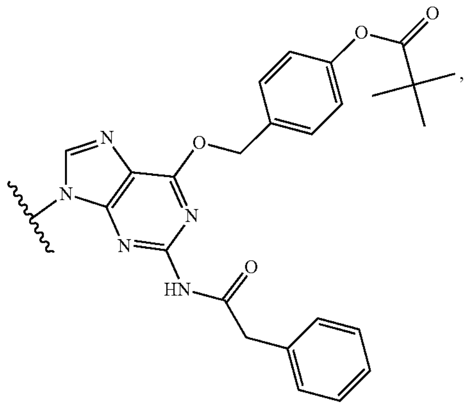
-continued
(T)
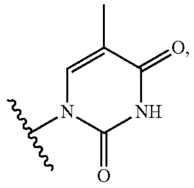
and
(PA)
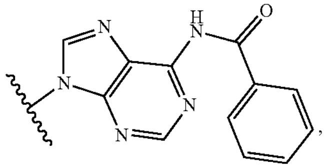
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |

-continued
| Position No. 5' to 3' | $R^2$ |
|---|---|
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |
In another aspect, provided herein is a compound of Formula (A11):
(A11)
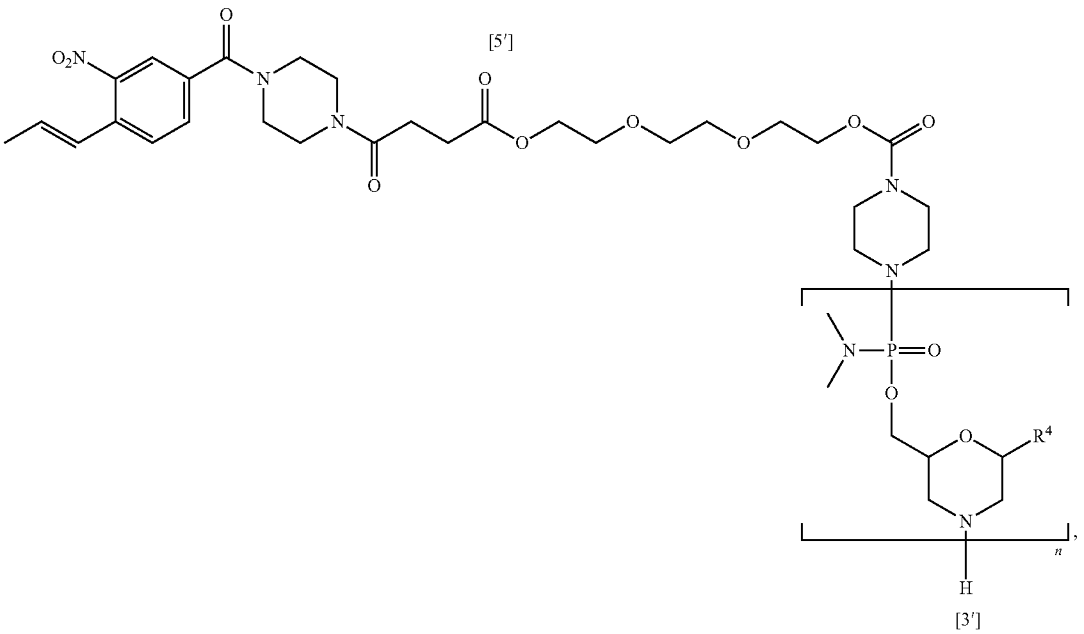
or a pharmaceutically acceptable salt thereof, wherein:
n is an integer from 10 to 40; and
$R^4$ is, independently at each occurrence, selected from the group consisting of:
(PC)
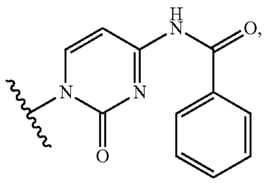
-continued
(DPG)
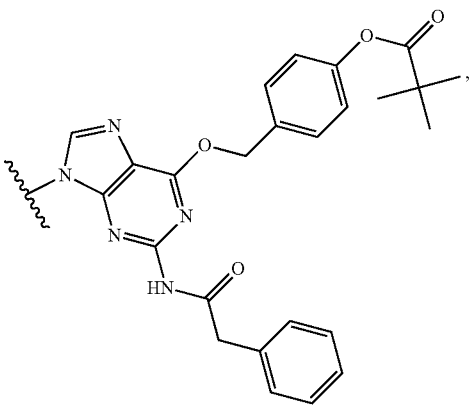

-continued
(T)
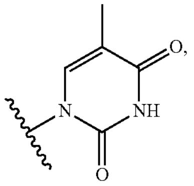
(PA)
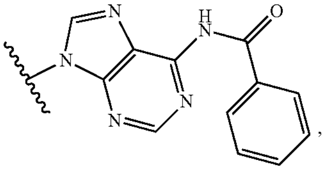
(P5mC)
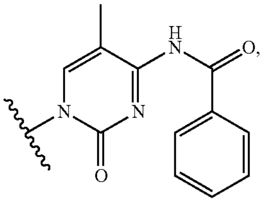
-continued
(U)
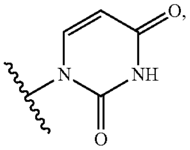
(I)
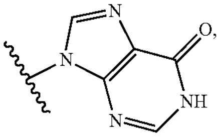
and
(PG)
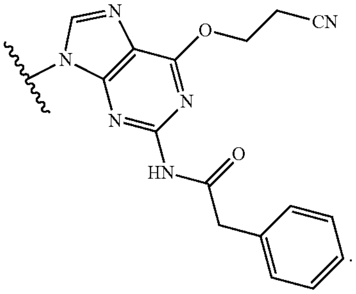
In one embodiment, the compound of Formula (A11) is of formula (A11a):
(A11a)
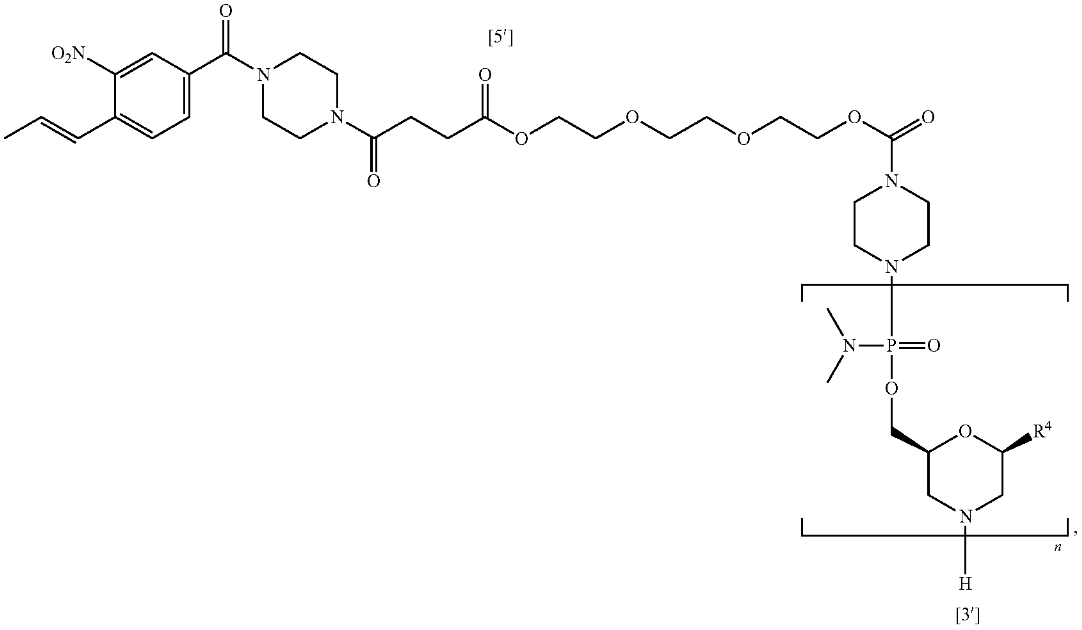

or a pharmaceutically acceptable salt thereof, wherein:

n is an integer from 10 to 40; and $R^4$ is, independently at each occurrence, selected from the group consisting of:

(PC)

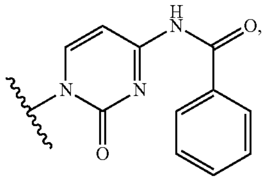

(DPG)

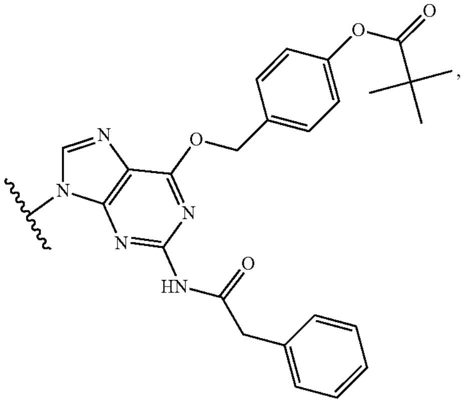

(T)

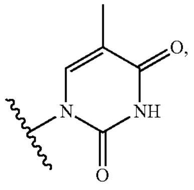

(PA)

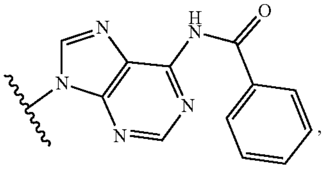

(P5mC)

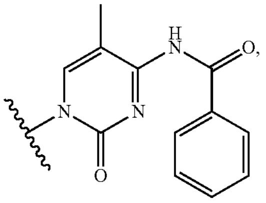

(U)

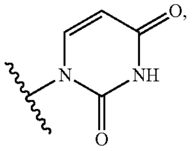

(I)

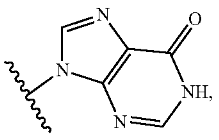

and

-continued (PG)

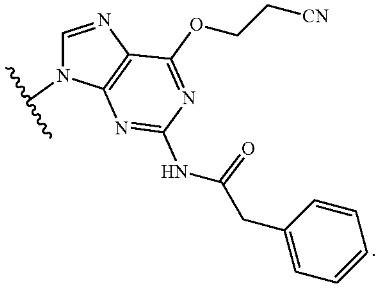

Oligomers

Important properties of morpholino-based subunits include: 1) the ability to be linked in an oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA; 3) the ability of the oligomer to be actively or passively transported into mammalian cells; and 4) the ability of the oligomer and oligomer:RNA heteroduplex to resist RNAse and RNase H degradation, respectively.

In some embodiments, the antisense oligomers contain base modifications or substitutions. For example, certain nucleo-bases may be selected to increase the binding affinity of the antisense oligomers described herein. 5-methylcytosine substitutions have been shown to increase nucleic acid duplex stability by 0.6-1.2° C., and may be incorporated into the antisense oligomers described herein. In one embodiment, at least one pyrimidine base of the oligomer comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligomer comprises hypoxanthine.

Morpholino-based oligomers (including antisense oligomers) are detailed, for example, in U.S. Pat. Nos. 5,698,685, 5,217,866, 5,142,047, 5,034,506, 5,166,315, 5,185,444, 5,521,063, 5,506,337, 8,299,206, and 8,076,476, International Patent Application Publication Nos. WO/2009/064471 and WO/2012/043730, and Summerton et al. (1997, *Antisense and Nucleic Acid Drug Development,* 7, 187-195), each of which are hereby incorporated by reference in their entirety.

Oligomeric compounds of the disclosure may have asymmetric centers, chiral axes, and chiral planes (as described, for example, in: E. L. Eliel and S. H. Wilen, *Stereochemistry of Carbon Compounds*, John Wiley & Sons, New York, 1994, pages 1119-1190, and March, *J. Advanced Organic Chemistry,* 3d. Ed., Chap. 4, John Wiley & Sons, New York (1985)), and may occur as racemates, racemic mixtures, and as individual diastereomers, with all possible isomers and mixtures thereof, including optical isomers. Oligomeric compounds of the disclosure herein specifically mentioned, without any indication of its stereo-chemistry, are intended to represent all possible isomers and mixtures thereof.

Specifically, without wishing to be bound by any particular theory, oligomeric compounds of the disclosure are prepared, as discussed herein, from activated morpholino subunits including such non-limiting examples such as a compound of Formula (VIII):

(VIII)

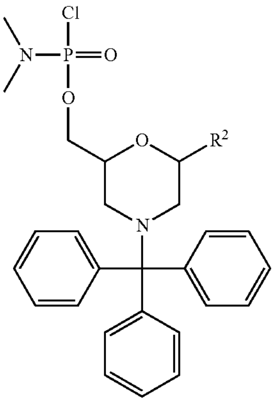

;

wherein $R^2$ is, independently for each compound of Formula (VIII), selected from the group consisting of:

(PC)

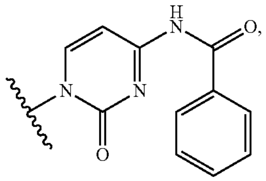

(DPG)

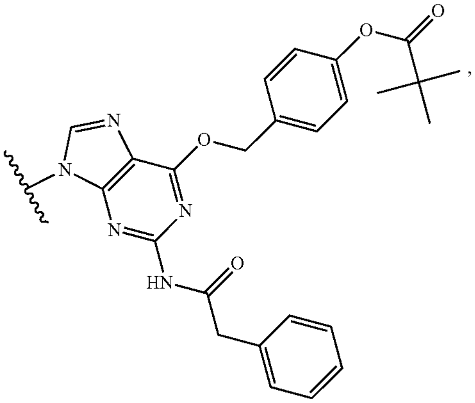

(T)

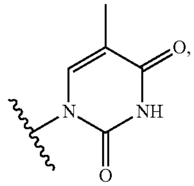

and (PA)

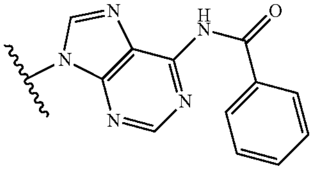

.

Each of the above-mentioned compounds of Formula (VIII), may be prepared, for example, from the corresponding beta-D-ribofuranosyl as depicted below:

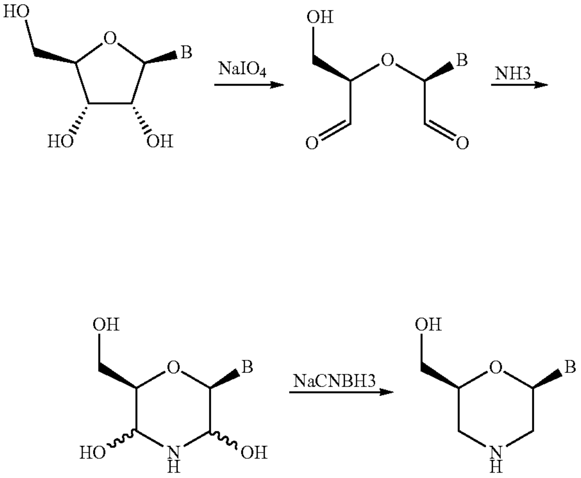

See Summerton et al., *Antisense & Nucleic Acid Drug Dev.* 7:187-195 (1997). Without being bound by any particular theory, the stereo chemistry of the two chiral carbons is retained under the synthetic conditions such that a number of possible stereo isomers of each morpholino subunit may be produced based on selection of, for example, an alpha-L-ribofuranosyl, alpha-D-ribofuranosyl, beta-L-ribofuranosyl, or beta-D-ribofuranosyl starting material.

For example, in some embodiments, a compound of Formula (VIII) of the disclosure may be of Formula (VIIIa):

(VIIIa)

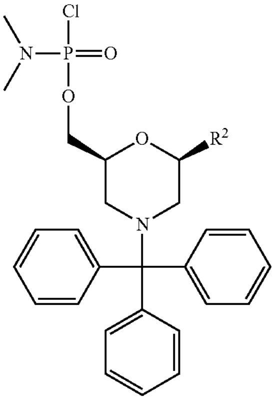

;

wherein $R^1$ is, independently for each compound of Formula (VIIIa), selected from the group consisting of:

(PC)

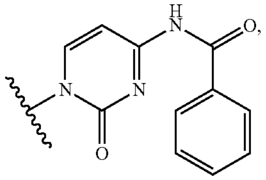

-continued (DPG)

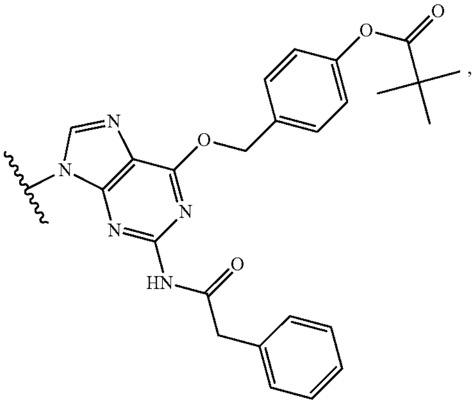

(T)

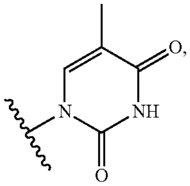

and (PA)

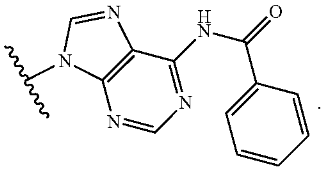

Without wishing to be bound by any particular theory, incorporation of 10 to 40 compounds of Formula (VIII), for example, into an oligomeric compound of the disclosure may result in numerous possible stereo isomers.

Without wishing to be bound by any particular theory, oligomeric compounds of the disclosure comprise one or more phosphorous-containing intersubunits, which create a chiral center at each phosphorus, each of which is designated as either an "Sp" or "Rp" configuration as understood in the art. Without wishing to be bound by any particular theory, this chirality creates stereoisomers, which have identical chemical composition but different three-dimensional arrangement of their atoms.

Without wishing to be bound by any particular theory, the configuration of each phosphorous intersubunit linkage occurs randomly during synthesis of, for example, oligomeric compounds of the disclosure. Without wishing to be bound by any particular theory, the synthesis process generates an exponentially large number of stereoisomers of an oligomeric compound of the disclosure because oligomeric compounds of the disclosure are comprised of numerous phosphorous intersubunit linkages—with each phosphorous intersubunit linkage having a random chiral configuration. Specifically, without wishing to be bound by any particular theory, each intersubunit linkage of an additional morpholino subunit doubles the number of stereoisomers of the product, so that a conventional preparation of an oligomeric compound of the disclosure is in fact a highly heterogeneous mixtures of $2^N$ stereoisomers, where N represents the number of phosphorous intersubunit linkages.

Thus, unless otherwise indicated, all such isomers, including diastereomeric and enantiomeric mixtures, and pure enantiomers and diastereomers are included such as, for example, when one or more bonds from one or more stereo center is indicated by "-" or "~~" or an equivalent as would be understood in the art.

Table 1 depicts various embodiments of morpholino subunits provided in the processes described herein.

TABLE 1

| Various embodiments of morpholino subunits. | |
|---|---|
| A = | 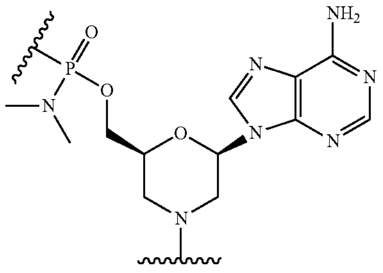 |
| G = | 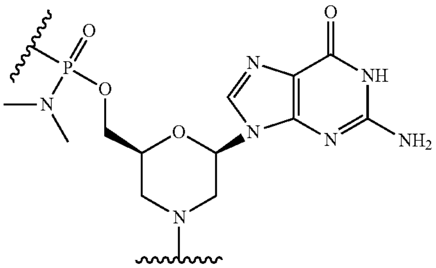 |
| C = | 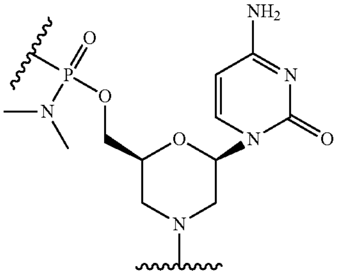 |
| T = | 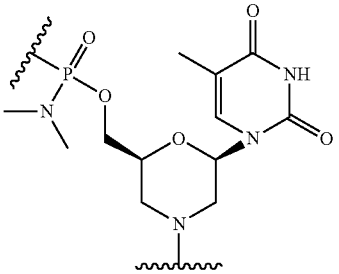 |
| 5-Me—C = | 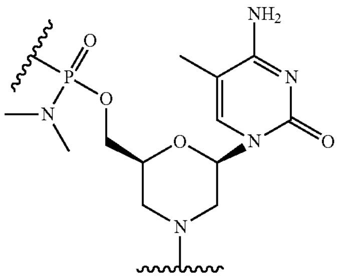 |

TABLE 1-continued

| Various embodiments of morpholino subunits. | |
|---|---|
| I = | 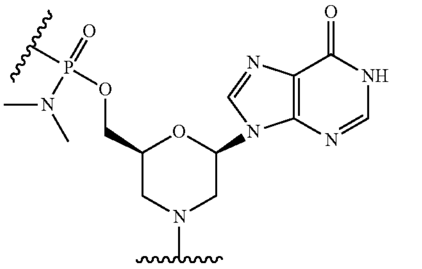 |
| U = | 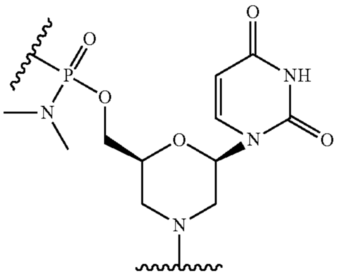 |

EXAMPLES

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Example 1: NCP2 Anchor Synthesis

1. Preparation of Methyl 4-Fluoro-3-Nitrobenzoate (1)

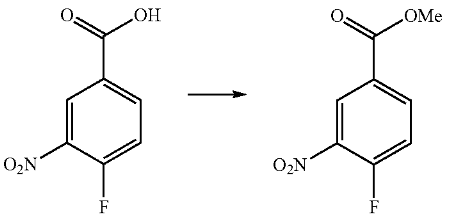

1

To a 100 L flask was charged 12.7 kg of 4-fluoro-3-nitrobenzoic acid was added 40 kg of methanol and 2.82 kg concentrated sulfuric acid. The mixture was stirred at reflux (65° C.) for 36 hours. The reaction mixture was cooled to 0° C. Crystals formed at 38° C. The mixture was held at 0° C.

for 4 hrs then filtered under nitrogen. The 100 L flask was washed and filter cake was washed with 10 kg of methanol that had been cooled to 0° C. The solid filter cake was dried on the funnel for 1 hour, transferred to trays, and dried in a vacuum oven at room temperature to a constant weight of 13.695 kg methyl 4-fluoro-3-nitrobenzoate (100% yield; HPLC 99%).

2. Preparation of 3-Nitro-4-(2-oxopropyl)benzoic Acid

A. (Z)-Methyl 4-(3-Hydroxy-1-Methoxy-1-Oxobut-2-en-2-yl)-3-Nitrobenzoate (2)

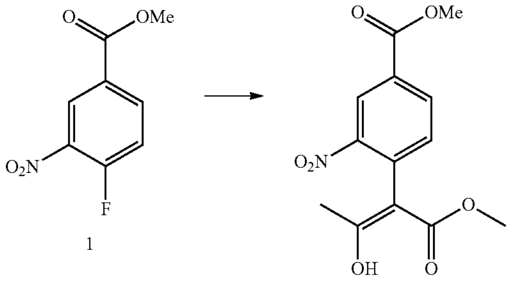

1 2

To a 100 L flask was charged 3.98 kg of methyl 4-fluoro-3-nitrobenzoate (1) from the previous step 9.8 kg DMF, 2.81 kg methyl acetoacetate. The mixture was stirred and cooled to 0° C. To this was added 3.66 kg DBU over about 4 hours while the temperature was maintained at or below 5° C. The mixture was stirred an additional 1 hour. To the reaction flask was added a solution of 8.15 kg of citric acid in 37.5 kg of purified water while the reaction temperature was maintained at or below 15° C. After the addition, the reaction mixture was stirred an addition 30 minutes then filtered under nitrogen. The wet filter cake was returned to the 100 L flask along with 14.8 kg of purified water. The slurry was stirred for 10 minutes then filtered. The wet cake was again returned to the 100 L flask, slurried with 14.8 kg of purified water for 10 minutes, and filtered to crude (Z)-methyl 4-(3-hydroxy-1-methoxy-1-oxobut-2-en-2-yl)-3-nitrobenzoate.

B. 3-Nitro-4-(2-oxopropyl)benzoic Acid

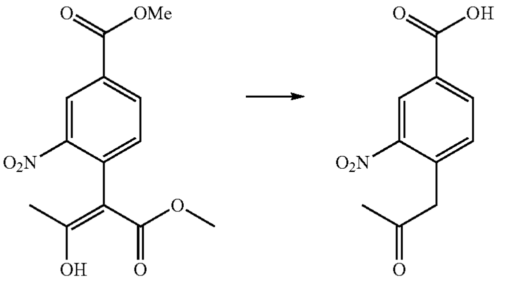

2 3

The crude (Z)-methyl 4-(3-hydroxy-1-methoxy-1-oxobut-2-en-2-yl)-3-nitrobenzoate was charged to a 100 L reaction flask under nitrogen. To this was added 14.2 kg 1,4-dioxane and the stirred. To the mixture was added a solution of 16.655 kg concentrated HCl and 13.33 kg purified water (6M HCl) over 2 hours while the temperature of the reaction mixture was maintained below 15° C. When the addition was complete, the reaction mixture was heated at reflux (80° C.) for 24 hours, cooled to room temperature, and filtered under nitrogen. The solid filter cake was triturated with 14.8 kg of purified water, filtered, triturated again with 14.8 kg of purified water, and filtered. The solid was returned to the 100 L flask with 39.9 kg of DCM and refluxed with stirring for 1 hour. 1.5 kg of purified water was added to dissolve the remaining solids. The bottom organic layer was split to a pre-warmed 72 L flask, then returned to a clean dry 100 L flask. The solution was cooled to 0° C., held for 1 hour, then filtered. The solid filter cake was washed twice each with a solution of 9.8 kg DCM and 5 kg heptane, then dried on the funnel. The solid was transferred to trays and dried to a constant weight of 1.855 kg 3-Nitro-4-(2-oxopropyl)benzoic Acid. Overall yield 42% from compound 1. HPLC 99.45%.

3. Preparation of N-Tritylpiperazine Succinate (NTP)

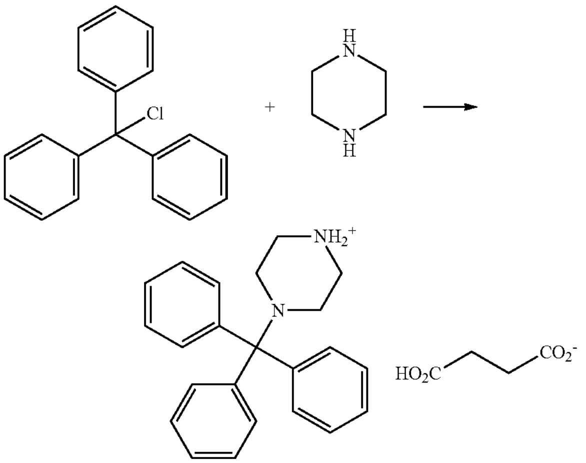

To a 72 L jacketed flask was charged under nitrogen 1.805 kg triphenylmethyl chloride and 8.3 kg of toluene (TPC solution). The mixture was stirred until the solids dissolved. To a 100 L jacketed reaction flask was added under nitrogen 5.61 kg piperazine, 19.9 kg toluene, and 3.72 kg methanol. The mixture was stirred and cooled to 0° C. To this was slowly added in portions the TPC solution over 4 hours while the reaction temperature was maintained at or below 10° C. The mixture was stirred for 1.5 hours at 10° C., then allowed to warm to 14° C. 32.6 kg of purified water was charged to the 72 L flask, then transferred to the 100 L flask while the internal batch temperature was maintained at 20+/−5° C. The layers were allowed to split and the bottom aqueous layer was separated and stored. The organic layer was extracted three times with 32 kg of purified water each, and the aqueous layers were separated and combined with the stored aqueous solution.

The remaining organic layer was cooled to 18° C. and a solution of 847 g of succinic acid in 10.87 kg of purified water was added slowly in portions to the organic layer. The mixture was stirred for 1.75 hours at 20+/−5° C. The mixture was filtered, and the solids were washed with 2 kg TBME and 2 kg of acetone then dried on the funnel. The filter cake was triturated twice with 5.7 kg each of acetone and filtered and washed with 1 kg of acetone between triturations. The solid was dried on the funnel, then transferred to trays and dried in a vacuum oven at room temperature to a constant weight of 2.32 kg of NTP. Yield 80%.

4. Preparation of (4-(2-Hydroxypropyl)-3-Nitrophenyl)(4-Tritylpiperazin-1-yl)Methanone

A. Preparation of 1-(2-Nitro-4(4-Tritylpiperazine-1-Carbonyl)Phenyl)Propan-2-one

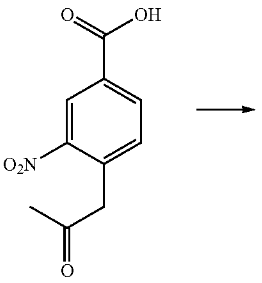

3

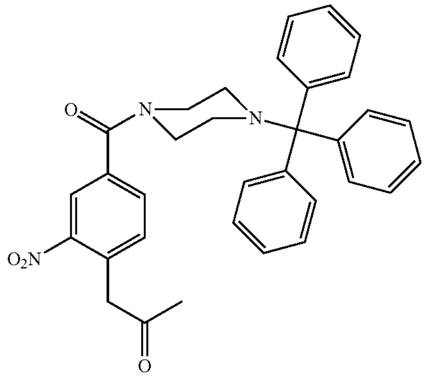

4

To a 100 L jacketed flask was charged under nitrogen 2 kg of 3-Nitro-4-(2-oxopropyl)benzoic Acid (3), 18.3 kg DCM, 1.845 kg N-(3-dimethylaminopropyl)-N'-ethylcarbodiimide hydrochloride (EDC.HCl). The solution was stirred until a homogenous mixture was formed. 3.048 kg of NTP was added over 30 minutes at room temperature and stirred for 8 hours. 5.44 kg of purified water was added to the reaction mixture and stirred for 30 minutes. The layers were allowed to separate and the bottom organic layer containing the product was drained and stored. The aqueous layer was extracted twice with 5.65 kg of DCM. The combined organic layers were washed with a solution of 1.08 kg sodium chloride in 4.08 kg purified water. The organic layers were dried over 1.068 kg of sodium sulfate and filtered. The sodium sulfate was washed with 1.3 kg of DCM. The combined organic layers were slurried with 252 g of silica gel and filtered through a filter funnel containing a bed of 252 g of silica gel. The silica gel bed was washed with 2 kg of DCM. The combined organic layers were evaporated on a rotovap. 4.8 kg of THF was added to the residue and then evaporated on the rotovap until 2.5 volumes of the crude 1-(2-nitro-4(4-tritylpiperazine-1-carbonyl)phenyl)propan-2-one in THF was reached.

B. Preparation of (4-(2-Hydroxypropyl)-3-Nitrophenyl)(4-Tritylpiperazin-1-yl)Methanone (5)

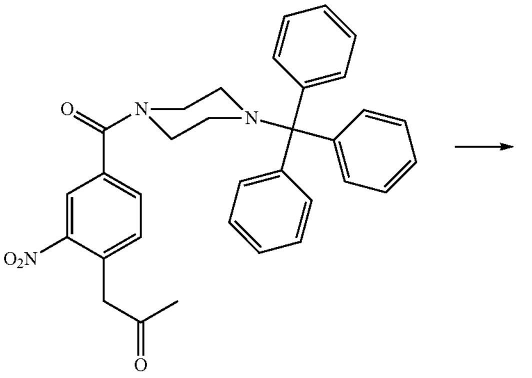

4

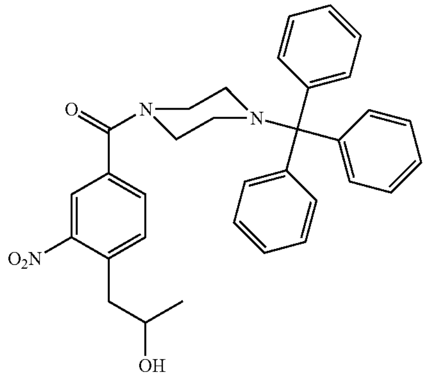

5

To a 100 L jacketed flask was charged under nitrogen 3600 g of 4 from the previous step and 9800 g THF. The stirred solution was cooled to ≤5° C. The solution was diluted with 11525 g ethanol and 194 g of sodium borohydride was added over about 2 hours at ≤5° C. The reaction mixture was stirred an additional 2 hours at ≤5° C. The reaction was quenched with a solution of about 1.1 kg ammonium chloride in about 3 kg of water by slow addition to maintain the temperature at ≤10° C. The reaction mixture was stirred an additional 30 minutes, filtered to remove inorganics, and recharged to a 100 L jacketed flask and extracted with 23 kg of DCM. The organic layer was separated and the aqueous was twice more extracted with 4.7 kg of DCM each. The combined organic layers were washed with a solution of about 800 g of sodium chloride in about 3 kg of water, then dried over 2.7 kg of sodium sulfate. The suspension was filtered and the filter cake was washed with 2 kg of DCM. The combined filtrates were concentrated to 2.0 volumes, diluted with about 360 g of ethyl acetate, and evaporated. The crude product was loaded onto a silica gel column of 4 kg of silica packed with DCM under nitrogen and eluted with 2.3 kg ethyl acetate in 7.2 kg of DCM. The combined fractions were evaporated and the residue was taken up in 11.7 kg of toluene. The toluene solution was filtered and the filter cake was washed twice with 2 kg of toluene each. The filter cake was dried to a constant weight of 2.275 kg of compound 5 (46% yield from compound 3) HPLC 96.99%.

5. Preparation of 2,5-Dioxopyrrolidin-1-yl(1-(2-Nitro-4-(4-triphenylmethylpiperazine-1 Carbonyl) Phenyl)Propan-2-yl) Carbonate (NCP2 Anchor)

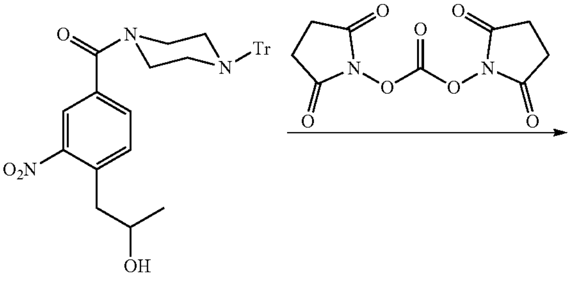

5

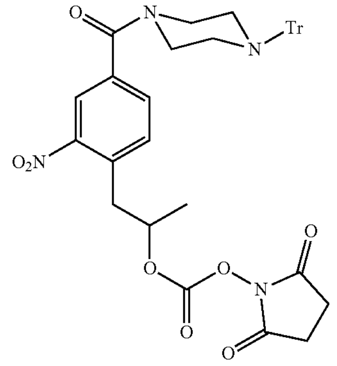

NCP2 Anchor

To a 100 L jacketed flask was charged under nitrogen 4.3 kg of compound 5 (weight adjusted based on residual toluene by $^{1}H$ NMR; all reagents here after were scaled accordingly) and 12.7 kg pyridine. To this was charged 3.160 kg of DSC (78.91 weight % by $^{1}H$ NMR) while the internal temperature was maintained at ≤35° C. The reaction mixture was aged for about 22 hours at ambience then filtered. The filter cake was washed with 200 g of pyridine. In two batches each comprising ½ the filtrate volume, filtrate wash charged slowly to a 100 L jacketed flask containing a solution of about 11 kg of citric acid in about 50 kg of water and stirred for 30 minutes to allow for solid precipitation. The solid was collected with a filter funnel, washed twice with 4.3 kg of water per wash, and dried on the filter funnel under vacuum.

The combined solids were charged to a 100 L jacketed flask and dissolved in 28 kg of DCM and washed with a solution of 900 g of potassium carbonate in 4.3 kg of water. After 1 hour, the layers were allowed to separate and the aqueous layer was removed. The organic layer was washed with 10 kg of water, separated, and dried over 3.5 kg of sodium sulfate. The DCM was filtered, evaporated, and dried under vacuum to 6.16 kg of NCP2 Anchor (114% yield).

Example 2: Anchor Loaded Resin Synthesis

To a 75 L solid phase synthesis reactor was charged about 52 L of NMP and 2600 g of aminomethyl polystyrene resin.

The resin was stirred in the NMP to swell for about 2 hours then drained. The resin was washed twice with about 39 L DCM per wash, then twice with 39 L Neutralization Solution per wash, then twice with 39 L of DCM per wash. The NCP2 Anchor Solution was slowly added to the stirring resin solution, stirred for 24 hours at room temperature, and drained. The resin was washed four times with 39 L of NMP per wash, and six times with 39 L of DCM per wash. The resin was treated and stirred with ½ the DEDC Capping Solution for 30 minutes, drained, and was treated and stirred with the $2^{nd}$ ½ of the DEDC Capping Solution for 30 minutes and drained. The resin was washed six times with 39 L of DCM per wash then dried in an oven to constant weight of 3573.71 g of Anchor Loaded Resin.

Example 3: Preparation of Activated EG3 Tail

1. Preparation of Trityl Piperazine Phenyl Carbamate 35

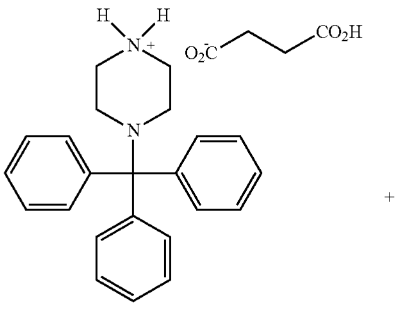

NTP

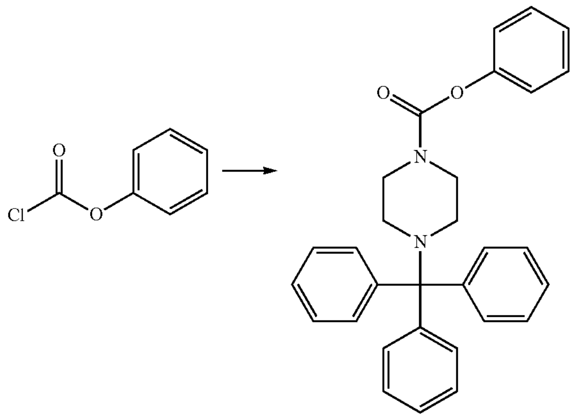

35

To a cooled suspension of NTP in dichloromethane (6 mL/g NTP) was added a solution of potassium carbonate (3.2 eq) in water (4 mL/g potassium carbonate). To this two-phase mixture was slowly added a solution of phenyl chloroformate (1.03 eq) in dichloromethane (2 g/g phenyl chloroformate). The reaction mixture was warmed to 20° C. Upon reaction completion (1-2 hr), the layers were separated. The organic layer was washed with water, and dried over anhydrous potassium carbonate. The product 35 was isolated by crystallization from acetonitrile. Yield=80%

2. Preparation of Carbamate Alcohol (36)

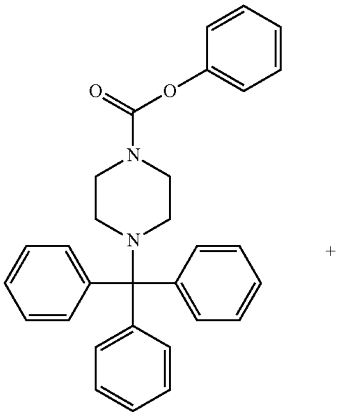

35

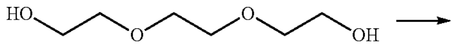

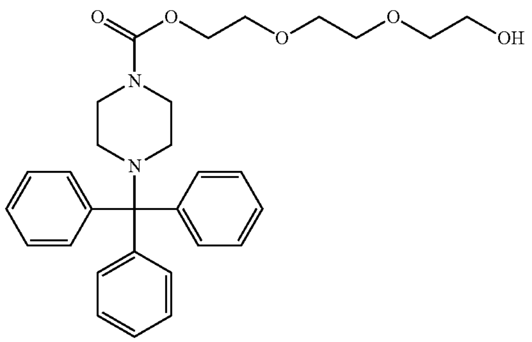

36

Sodium hydride (1.2 eq) was suspended in 1-methyl-2-pyrrolidinone (32 mL/g sodium hydride). To this suspension were added triethylene glycol (10.0 eq) and compound 35 (1.0 eq). The resulting slurry was heated to 95° C. Upon reaction completion (1-2 hr), the mixture was cooled to 20° C. To this mixture was added 30% dichloromethane/methyl tert-butyl ether (v:v) and water. The product-containing organic layer was washed successively with aqueous NaOH, aqueous succinic acid, and saturated aqueous sodium chloride. The product 36 was isolated by crystallization from dichloromethane/methyl tert-butyl ether/heptane. Yield=90%.

3. Preparation of EG3 Tail Acid (37)

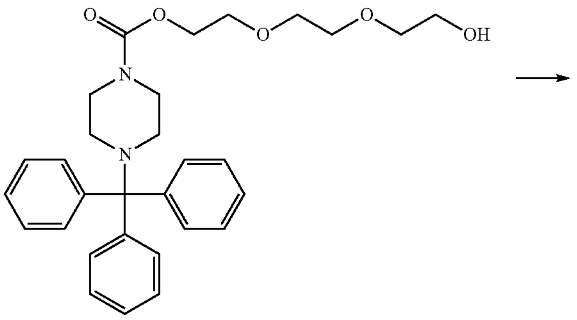

36

-continued

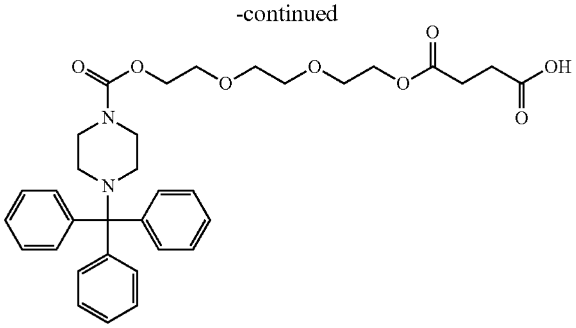

37

To a solution of compound 36 in tetrahydrofuran (7 mL/g 36) was added succinic anhydride (2.0 eq) and DMAP (0.5 eq). The mixture was heated to 50° C. Upon reaction completion (5 hr), the mixture was cooled to 20° C. and adjusted to pH 8.5 with aqueous $NaHCO_3$. Methyl tert-butyl ether was added, and the product was extracted into the aqueous layer. Dichloromethane was added, and the mixture was adjusted to pH 3 with aqueous citric acid. The product-containing organic layer was washed with a mixture of pH=3 citrate buffer and saturated aqueous sodium chloride. This dichloromethane solution of 37 was used without isolation in the preparation of compound 38.

4. Preparation of Activated EG3 Tail (38)

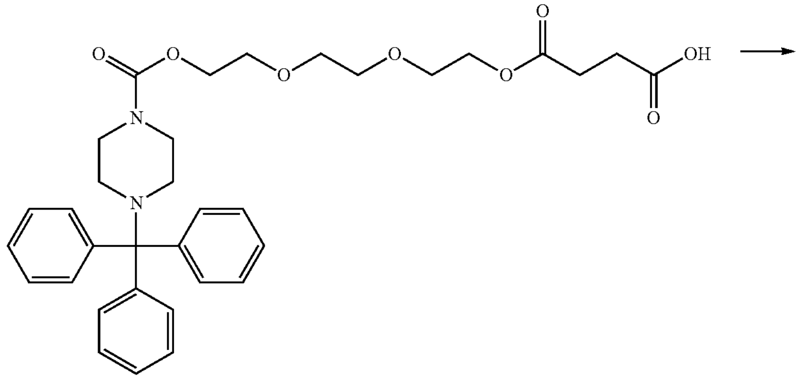

37

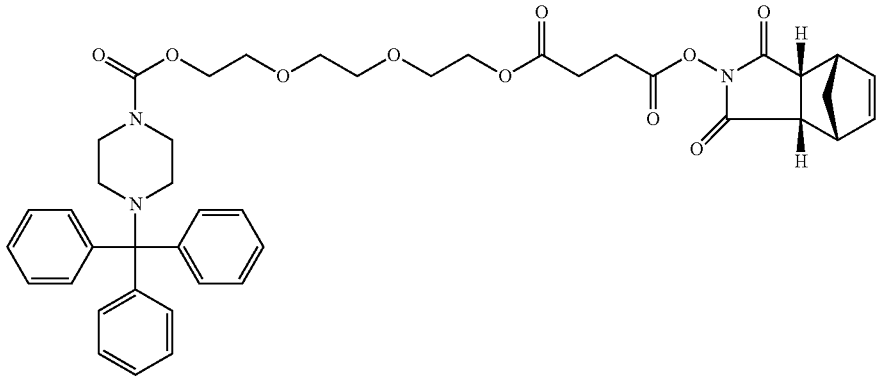

38

To the solution of compound 37 was added N-hydroxy-5-norbornene-2,3-dicarboxylic acid imide (HONB) (1.02 eq), 4-dimethylaminopyridine (DMAP) (0.34 eq), and then 1-(3-dimethylaminopropyl)-N'-ethylcarbodiimide hydrochloride (EDC) (1.1 eq). The mixture was heated to 55° C. Upon reaction completion (4-5 hr), the mixture was cooled to 20° C. and washed successively with 1:1 0.2 M citric acid/brine and brine. The dichloromethane solution underwent solvent exchange to acetone and then to N,N-dimethylformamide, and the product was isolated by precipitation from acetone/N,N-dimethylformamide into saturated aqueous sodium chloride. The crude product was reslurried several times in water to remove residual N,N-dimethylformamide and salts. Yield=70% of Activated EG3 Tail 38 from compound 36.

Example 4: 50 L Solid-phase Synthesis of Golodirsen [Oligomeric Compound (XII)] Crude Drug Substance 1. Materials

TABLE 2

| Starting Materials | | | | |
|---|---|---|---|---|
| Material Name | Chemical Name | CAS Number | Chemical Formula | Molecular Weight |
| Activated A Subunit | Phosphoramidochloridic acid, N,N-dimethyl-,[6-[6-(benzoylamino)-9H-purin-9-yl]-4-(triphenylmethyl)-2-morpholinyl]methyl ester | 1155373-30-0 | $C_{38}H_{37}ClN_7O_4P$ | 722.2 |
| Activated C Subunit | Phosphoramidochloridic acid, N,N-dimethyl-,[6-[4-(benzoylamino)-2-oxo-1(2H)-pyrimidinyl]-4-(triphenylmethyl)-2-morpholinyl]methyl ester | 1155373-31-1 | $C_{37}H_{37}ClN_5O_5P$ | 698.2 |
| Activated DPG Subunit | Propanoic Acid, 2,2-dimethyl-, 4-[[[9-[6-[[[chloro(dimethyl-amino)phosphinyl]oxy]methyl]-4-(triphenylmethyl)-2-morpholinyl]-2-[(2-phenylacetyl)amino]-9H-purin-6-yl]oxy]methyl]phenyl ester | 1155309-89-9 | $C_{51}H_{53}ClN_7O_7p$ | 942.2 |
| Activated T Subunit | Phosphoramidochloridic acid, N,N-dimethyl-,[6-(3,4-dihydro-5-methyl-2,4-dioxo-1(2H)-pyrimidinyl)]-4-(triphenylmethyl)-2-morpholinyl]methyl ester | 1155373-34-4 | $C_{31}H_{34}ClN_4O_5p$ | 609.1 |
| Activated EG3 Tail | Butanedioic acid, 1-[3aR,4S,7R,7aS)-1,3,3a,4,7,7a-hexahydro-1,3-dioxo-4,7-methano-2H-isoindol-2-yl] 4-[2-[2-[2-[[[4-(triphenylmethyl)-1-piperazinyl]carbonyl]oxy]ethoxy]ethoxy]ethyl] ester | 1380600-06-5 | $C_{43}H_{47}N_3O_{10}$ | 765.9 |

Chemical Structures of Starting Materials:
A. Activated EG3 Tail

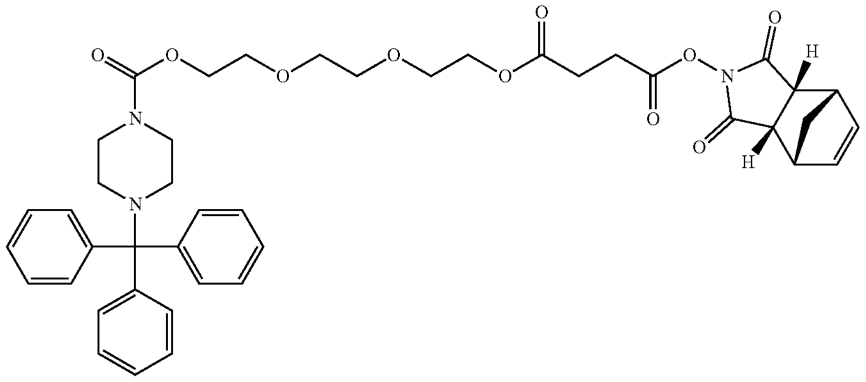

Compound (B)

B. Activated C Subunit (for Preparation, See U.S. Pat. No. 8,067,571)

Compound (C1)

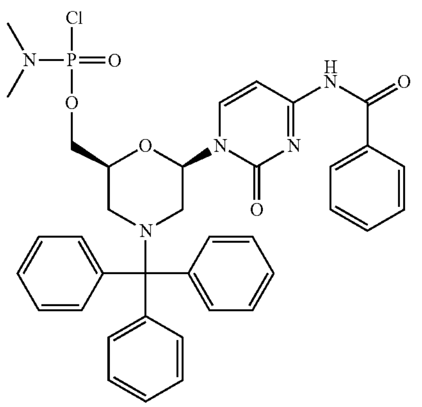

C. Activated a Subunit (for Preparation, See U.S. Pat. No. 8,067,571)

Compound (D1)

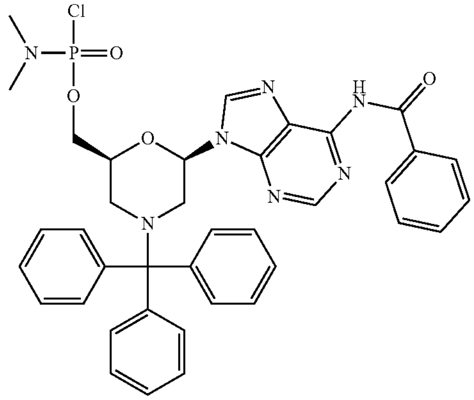

D. Activated DPG Subunit (for Preparation, See WO 2009/064471)

Compound (DPG1)

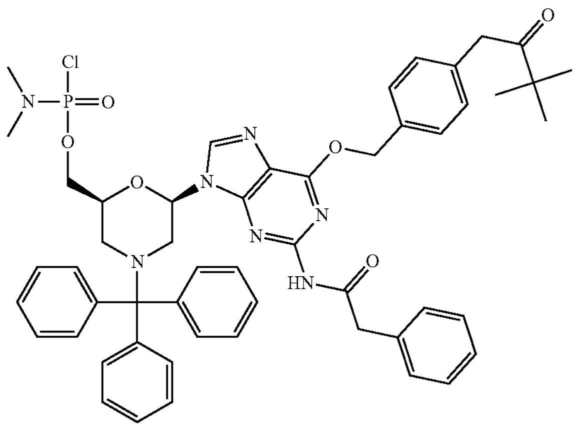

E. Activated T Subunit (for Preparation, See WO 2013/082551)

Compound (T1)

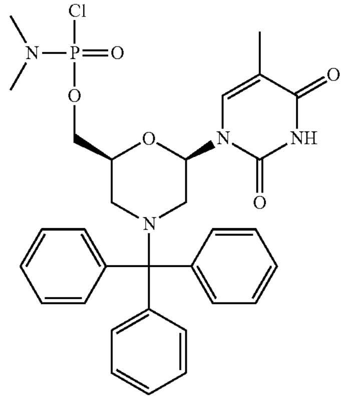

F. Anchor Loaded Resin

Formula (I)

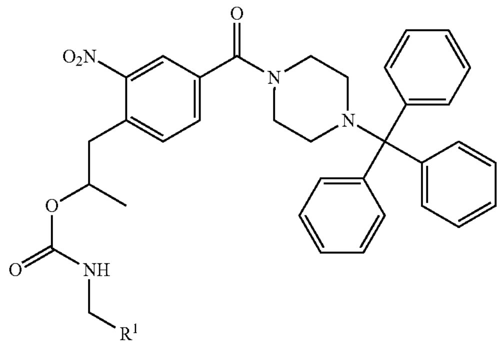

wherein $R^1$ is a support-medium.

TABLE 3

Description of Solutions for Solid Phase Oligomer Synthesis of Golodirsen Crude Drug Substance

| Solution Name | Solution Composition |
|---|---|
| NCP2 Anchor Solution | 37.5 L NMP and 1292 g NCP2 Anchor |
| DEDC Capping Solution | 4.16 L Diethyl Dicarbonate (DEDC), 3.64 L NEM, and 33.8 L DCM |
| CYTFA Solution | 2.02 kg 4-cyanopyridine, 158 L DCM, 1.42 L TFA, 39 L TFE, and 2 L purified water |
| Neutralization Solution | 35.3 L IPA, 7.5 L DIPEA, and 106.5 L DCM |
| Cleavage Solution | 1,530.04 g DTT, 6.96 L NMP, and 2.98 L DBU |

2. Synthesis of Golodirsen Crude Drug Substance

A. Resin Swelling 750 g of Anchor Loaded Resin and 10.5 L of NMP were charged to a 50 L silanized reactor and stirred for 3 hours. The NMP was drained and the Anchor Loaded Resin was washed twice with 5.5 L each of DCM and twice with 5.5 L each of 30% TFE/DCM.

B. Cycle 0: EG3 Tail Coupling

The Anchor Loaded Resin was washed three times with 5.5 L each of 30% TFE/DCM and drained, washed with 5.5 L of CYFTA solution for 15 minutes and drained, and again washed with 5.5 L of CYTFA Solution for 15 minutes without draining to which 122 mL of 1:1 NEM/DCM was charged and the suspension stirred for 2 minutes and drained. The resin was washed once with 5.5 L Neutralization Solution for 10 minutes and drained, twice with 5.5 L of Neutralization Solution for 5 minutes and drained, then twice with 5.5 L each of DCM and drained. A solution of 706.2 g of activated EG3 Tail (MW 765.85) and 234 mL of NEM in 3 L of DMI was charged to the resin and stirred for 3 hours at RT and drained. The resin was washed once with 5.5 L of Neutralization Solution for 10 minutes and drained, once with 5.5 L of Neutralization Solution for 5 minutes and drained, and once with 5.5 L of DCM and drained. A solution of 374.8 g of benzoic anhydride and 195 mL NEM in 2680 mL NMP was charged and stirred for 15 minutes and drained. The resin was once with 5.5 L of Neutralization Solution for 10 minutes and drained, once with 5.5 L of Neutralization Solution for 5 minutes and drained, and once with 5.5 L of DCM and drained and twice with 5.5 L each of 30% TFE/DCM. The resin was suspended in 5.5 L of 30% TFE/DCM and held for 14 hours.

C. Subunit Coupling Cycles 1-30 i. Pre-Coupling Treatments

Prior to each coupling cycle as described in FIG. 1, the resin was: 1) washed with 30% TFE/DCM; 2) a) treated with CYTFA Solution 15 minutes and drained, and b) treated with CYTFA solution for 15 minutes to which was added 1:1 NEM/DCM, stirred, and drained; 3) stirred three times with Neutralization Solution; and 4) washed twice with DCM. See Table 4.

ii. Post Coupling Treatments

After each subunit solution was drained as described in Table 4, the resin was: 1) washed with DCM; and 2) washed three times with 30% TFE/DCM. If the resin was held for a time period prior to the next coupling cycle, the third TFE/DCM wash was not drained and the resin was retained in said TFE/DCM wash solution. See Table 4.

iii. Activated Subunit Coupling Cycles

The coupling cycles were performed as described in Table 4.

iv. Final IPA Washing

After the final coupling step was performed as described in Table 4, the resin was washed 8 times with 19.5 L each of IPA, and dried under vacuum at room temperature for about 63.5 hours to a dried weight of 4857.9 g.

D. Cleavage

The above resin bound Eteplisen Crude Drug Substance was divided into two lots, each lot was treated as follows. A 1619.3 g lot of resin was: 1) stirred with 10 L of NMP for 2 hrs, then the NMP was drained; 2) washed tree times with 10 L each of 30% TFE/DCM; 3) treated with 10 L CYTFA Solution for 15 minutes; and 4) 10 L of CYTFA Solution for 15 minutes to which 130 ml 1:1 NEM/DCM was then added and stirred for 2 minutes and drained. The resin was treated three times with 10 L each of Neutralization Solution, washed six times with 10 L of DCM, and eight times with 10 L each of NMP. The resin was treated with a Cleaving Solution of 1530.4 g DTT and 2980 DBU in 6.96 L NMP for 2 hours to detach the Eteplisen Crude Drug Substance from the resin. The Cleaving Solution was drained and retained in a separate vessel. The reactor and resin were washed with 4.97 L of NMP which was combined with the Cleaving Solution.

TABLE 4

| | Pre-coupling Treatment | | | | Coupling Cycle | | Post-Coupling Treatment | |
|---|---|---|---|---|---|---|---|---|
| Cycle No.: Subunit (SU) | 1 30% TFE/DCM Wash | 2 CYTFA Solution[1] | 3 Neutralization Solution | 4 DCM Wash | Quantity SU (g) NEM (L) DMI (L) | RT Coupling Time (Hrs.) | 1 DCM Wash | 2 30% TFE/DCM Wash |
| 1: DPG | 5.5 L | a) 5.5 L b) 5.5 L, 122 ml | 3 × 5.5 L | 5.5 L | 536.7 g; 195 ml NEM; 3.2 L DMI | 5 | 5.5 L | 3 × 5.5 L |
| 2: T | 7.0 L | a) 7 L b) 7 L, 158 ml | 3 × 7 L | 2 × 7 L | 468.2 g and 195 ml NEM 3.2 L DMI | 4.25 | 7 L | 3 × 7 L |
| 3: T | 8 L | a) 8 L b) 8 L, 182 ml | 3 × 8 L | 2 × 8 L | 536.7 g; 195 ml NEM; 3.4 L DMI | 4.25 | 8 L | 3 × 8 L |
| 4: DPG | 9 L | a) 9 L b) 9 L, 206 ml | 3 × 9 L | 2 × 9 L | 536.7 g; 195 ml NEM; 3.6 L DMI | 4.25 | 9 L | 3 × 9 L |
| 5: C | 9.5 L | a) 9.5 L b) 9.5 L, 220 ml | 3 × 9.5 L | 2 × 9.5 L | 555.2 g; 195 ml NEM; 3.4 L DMI | 4.25 | 9.5 L | 3 × 9.5 L |
| 6: C | 10 L | a) 10 L b) 10 L, 232 ml | 3 × 10 L | 2 × 10 L | 555.2 g; 195 ml NEM; 3.45 L DMI | 4.25 | 10 L | 3 × 10 L |
| 7: T | 11 L | a) 11 L b) 11 L, 256 ml | 3 × 11 L | 2 × 11 L | 536.7 g; 195 ml NEM; 3.57 L DMI | 4.25 | 11 L | 3 × 11 L |
| 8: C | 11 L | a) 11 L b) 11 L, 256 ml | 3 × 11 L | 2 × 11 L | 555.2 g; 195 ml NEM; 3.64 L DMI | 4.25 | 11 L | 3 × 11 L |
| 9: C | 11.5 L | a) 11.5 L b) 11.5 L 268 ml | 3 × 11.5 L | 2 × 11.5 L | 468.2 g; 195 ml NEM; 3.72 L DMI | 4.25 | 11.5 L | 3 × 11.5 L |
| 10: DPG | 12 L | a) 12 L b) 12 L, 280 ml | 3 × 12 L | 2 × 12 L | 536.7 g; 195 ml NEM; 3.96 L DMI | 4.25 | 12 L | 3 × 12 L |

TABLE 4-continued

| | Pre-coupling Treatment | | | | Coupling Cycle | | Post-Coupling Treatment | |
|---|---|---|---|---|---|---|---|---|
| Cycle No.: Subunit (SU) | 1 30% TFE/DCM Wash | 2 CYTFA Solution[1] | 3 Neutralization Solution | 4 DCM Wash | Quantity SU (g) NEM (L) DMI (L) | RT Coupling Time (Hrs.) | 1 DCM Wash | 2 30% TFE/DCM Wash |
| 11: DPG | 13.5 L | a) 13.5 L b) 13.5 L, 204 ml | 3 × 13.5 L | 2 × 13.5 L | 721.7 g; 253 ml NEM; 4.02 L DMI | 4.25 | 13.5 L | 3 × 13.5 L |
| 12: T | 13.5 L | a) 13.5 L b) 13.5 L, 204 ml | 3 × 13.5 L | 2 × 13.5 L | 721.7 g; 253 ml NEM; 4.02 L DMI | 4.25 | 13.5 L | 3 × 13.5 L |
| 13: T | 14 L | a) 14 L b) 14 L, 216 ml | 3 × 14 L | 2 × 14 L | 941.9 g; 253 ml NEM; 4.02 L DMI | 4.25 | 14 L | 3 × 14 L |
| 14: C | 14.5 L | a) 14.5 L b) 14.5 L, 228 ml | 3 × 14.5 L | 2 × 14.5 L | 941.9 g; 253 ml NEM; 4.1 L DMI | 4.25 | 14.5 L | 3 × 14.5 L |
| 15: T | 15.5 L | a) 15.5 L b) 15.5 L, 254 ml | 3 × 15.5 L | 2 × 15.5 L | 721.7 g; 253 ml NEM; 4.26 L DMI | 4.25 | 15.5 L | 3 × 15.5 L |
| 16: DPG | 15.5 L | a) 15.5 L b) 15.5 L, 254 ml | 3 × 15.5 L | 2 × 15.5 L | 721.7 g; 253 ml NEM; 4.26 L DMI | 4.25 | 15.5 L | 3 × 15.5 L |
| 17: A | 16 L | a) 16 L b) 16 L, 366 ml | 3 × 16 L | 2 × 16 L | 941.9 g; 253 ml NEM; 4.4 L DMI | 4.75 | 16 L | 3 × 16 L |
| 18: A | 16.5 L | a) 16.5 L b) 16.5 L, 378 ml | 3 × 16.5 L | 2 × 16.5 L | 721.7 g; 253 ml NEM; 4.4 L DMI | 4.25 | 16.5 L | 3 × 16.5 L |
| 19: DPG | 16.5 L | a) 16.5 L b) 16.5 L, 378 ml | 3 × 16.5 L | 2 × 16.5 L | 608.7 g; 253 ml NEM; 4.57 L DMI | 4.25 | 16.5 L | 3 × 16.5 L |
| 20: DPG | 17 L | a) 17 L b) 17 L, 390 ml | 3 × 17 L | 2 × 17 L | 941.9 g; 253 ml NEM; 4.57 L DMI | 4.75 | 17 L | 3 × 17 L |
| 21: T | 17 L | a) 17 L b) 17 L, 390 ml | 3 × 17 L | 2 × 17 L | 1159.2 g; 311 ml NEM; 4.72 L DMI | 4.25 | 17 L | 3 × 17 L |
| 22: DPG | 17.5 L | a) 17.5 L b) 17.5 L, 402 ml | 3 × 17.5 L | 2 × 17.5 L | 858.7 g; 311 ml NEM; 4.72 L DMI | 4.75 | 17.5 L | 3 × 17.5 L |
| 23: T | 17.5 L | a) 17.5 L b) 17.5 L, 402 ml | 3 × 17.5 L | 2 × 17.5 L | 888.3 g; 311 ml NEM; 4.88 L DMI | 4.25 | 17.5 L | 3 × 17.5 L |
| 24: T | 18 L | a) 18 L b) 18 L, 414 ml | 3 × 18 L | 2 × 18 L | 749.1 g; 311 ml NEM; 4.95 L DMI | 4.25 | 18 L | 3 × 18 L |
| 25: C | 18 L | a) 18 L b) 18 L, 414 ml | 3 × 18 L | 2 × 18 L | 749.1 g; 311 ml NEM; 5.1 L DMI | 4.25 | 18 L | 3 × 18 L |

[1]ml indicates the amount of 1:1 NEM/DCM

E. Deprotection

Figure 2:
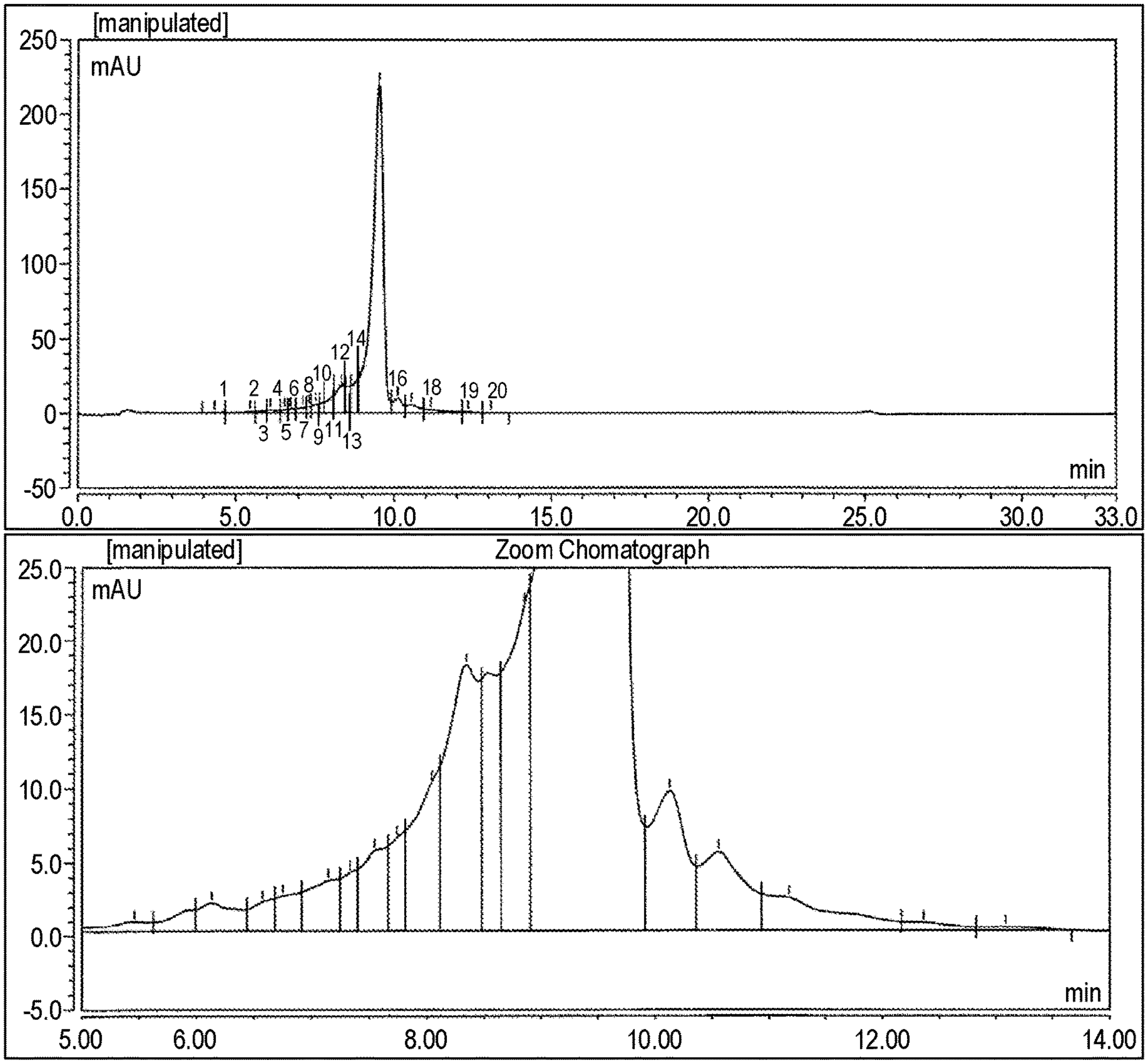

The combined Cleaving Solution and NMP wash were transferred to a pressure vessel to which was added 39.8 L of $NH_4OH$ ($NH_3.H_2O$) that had been chilled to a temperature of −10° to −25° C. in a freezer. The pressure vessel was sealed and heated to 45° C. for 16 hrs then allowed to cool to 25° C. This deprotection solution containing the Golodirsen crude drug substance was diluted 3:1 with purified water prior to solvent removal. During solvent removal, the deprotection solution was pH adjusted to 3.0 with 2M phosphoric acid, then to pH 8.03 with $NH_4OH$. HPLC: C18 77.552% (FIG. 1) and SCX-10 73.768% (FIG. 2).

Example 5: Purification of Golodirsen Crude Drug Substance

Figure 3:
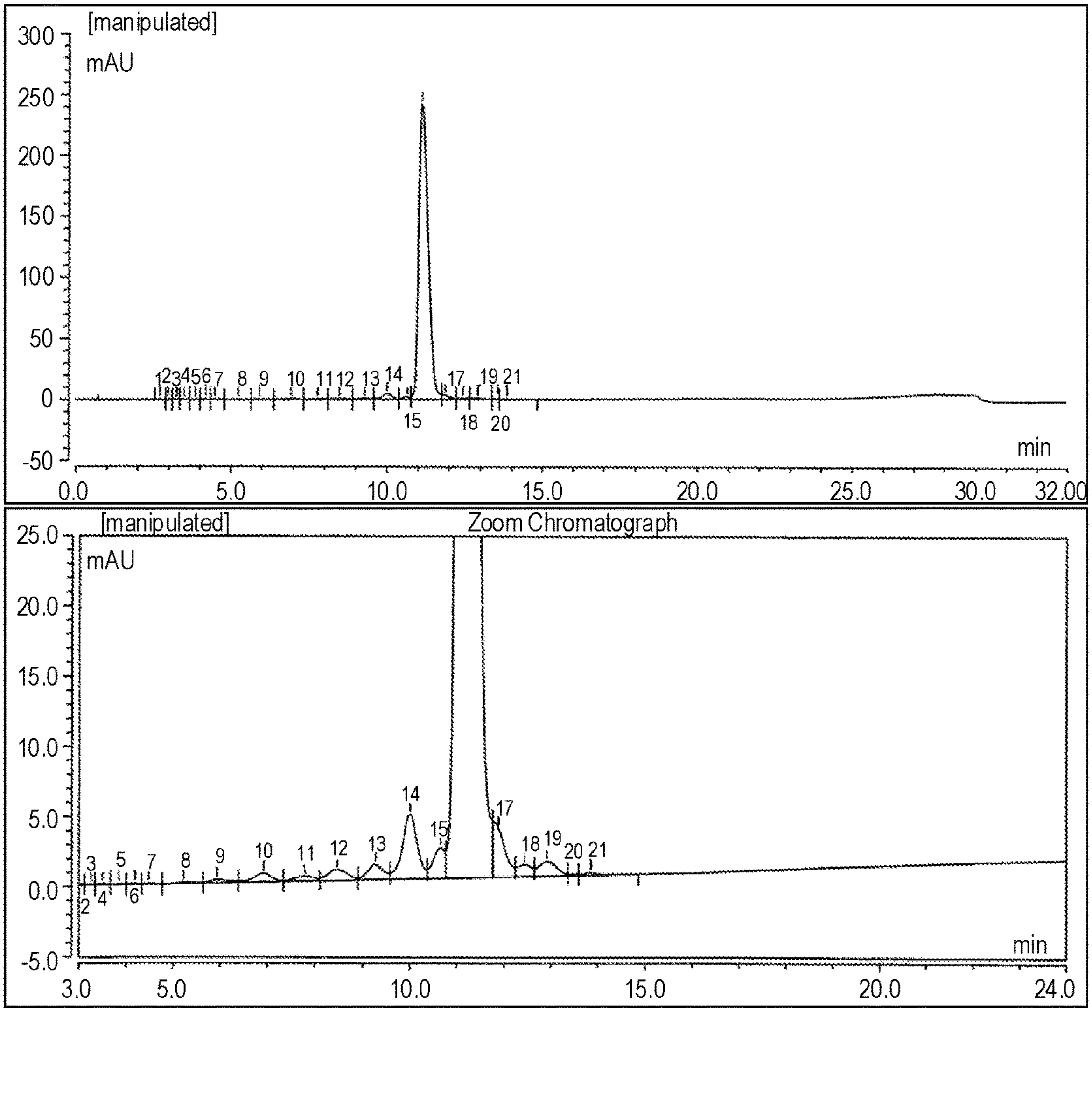
FIG. 3 and FIG. 4 show a representative analytical HPLC chromatogram of a purified Golodirsen drug substance solution (see Example 5).
Figure 4:
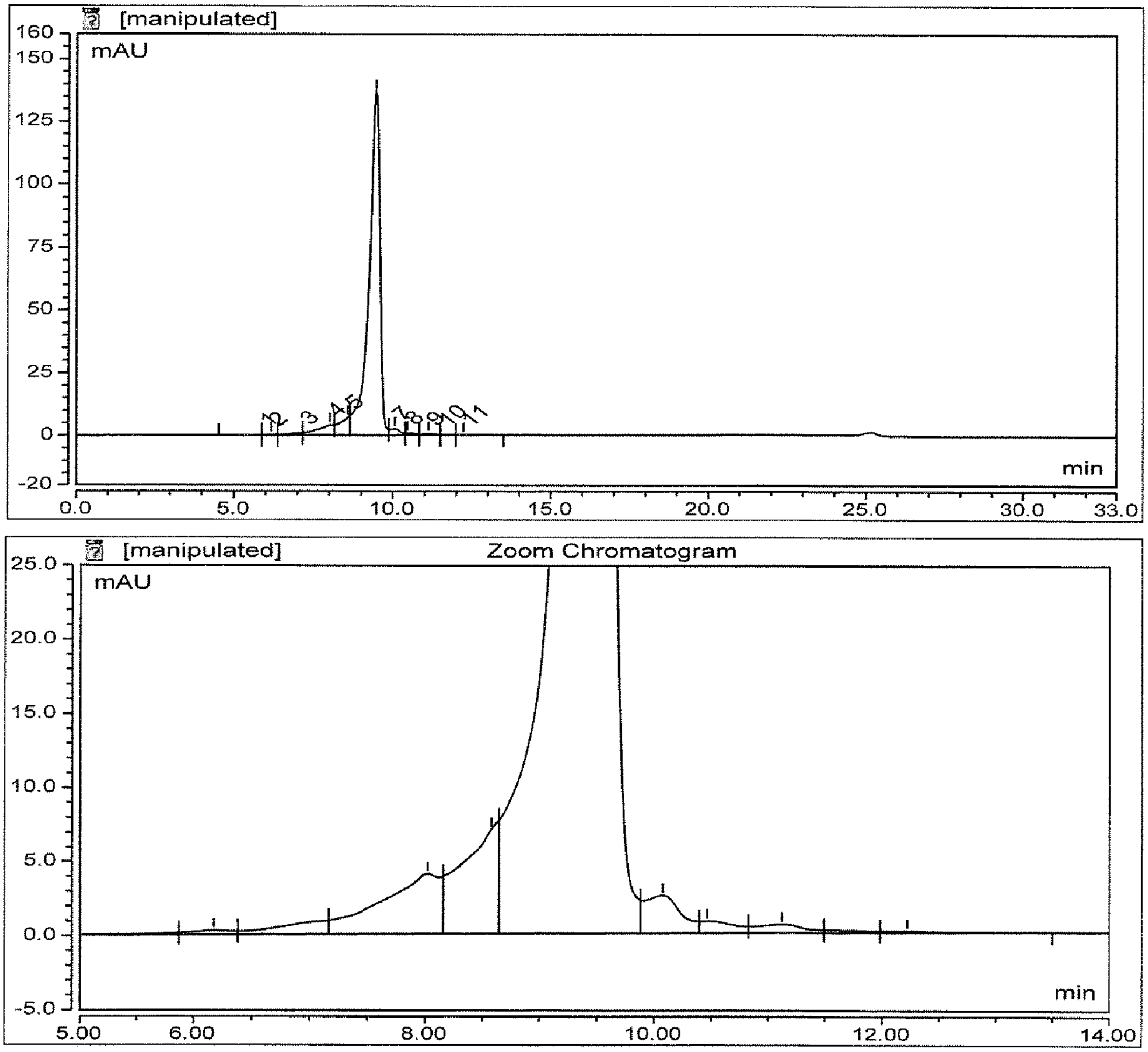

The deprotection solution from Example 4, part E, containing the Golodirsen crude drug substance was loaded onto a column of ToyoPearl Super-Q 650S anion exchange resin (Tosoh Bioscience) and eluted with a gradient of 0-35% B over 17 column volume (Buffer A: 10 mM sodium hydroxide; Buffer B: 1 M sodium chloride in 10 mM sodium hydroxide) and fractions of acceptable purity (C18 and SCX HPLC) were pooled to a purified drug product solution. HPLC: 93.571% (C18; FIG. 3) 88.270% (SCX; FIG. 4).

Figure 5:
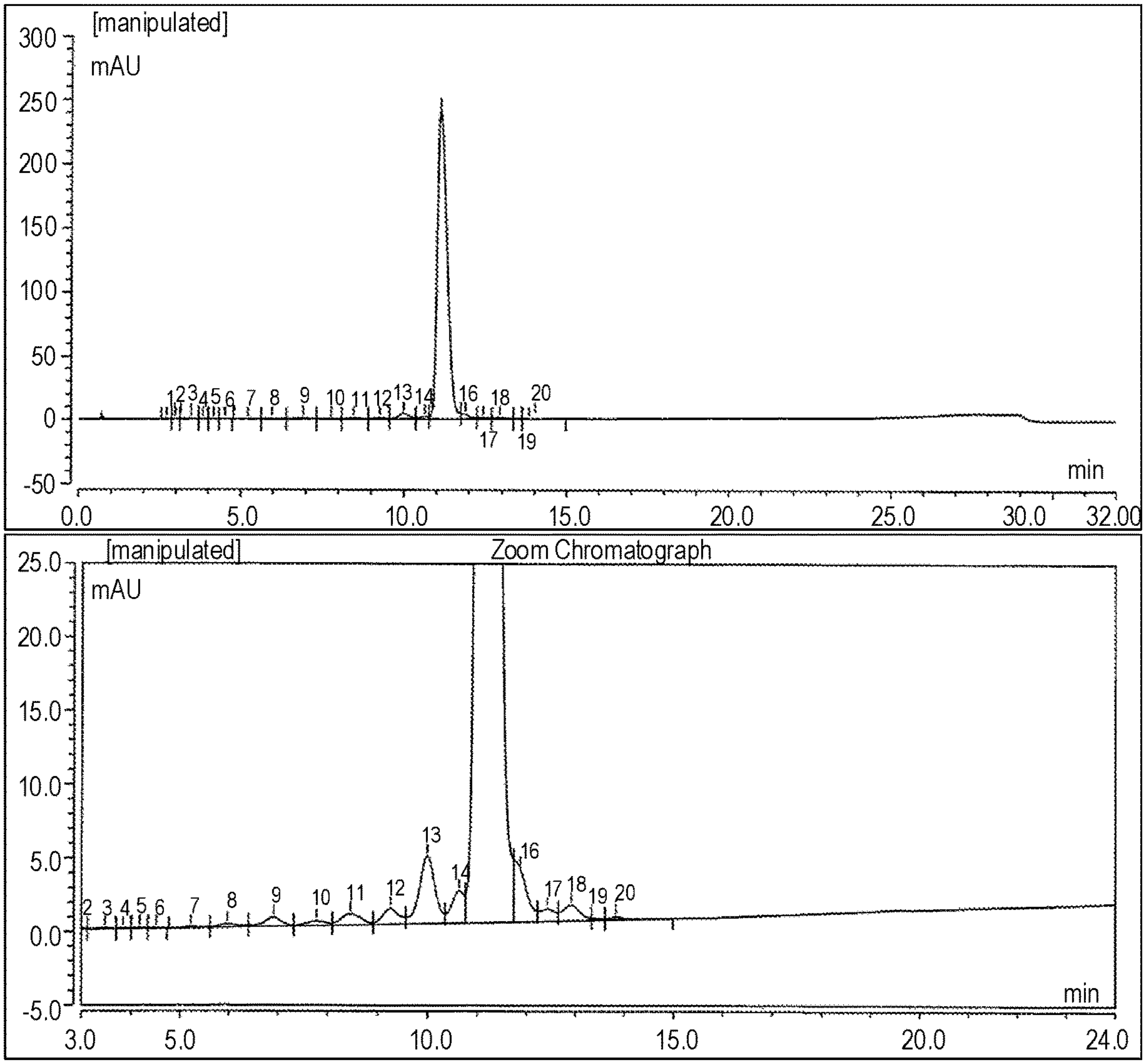
FIG. 5 and FIG. 6 show a representative analytical HPLC chromatogram of a desalted and lyophilized Golodirsen drug substance (see Example 5).
Figure 6:
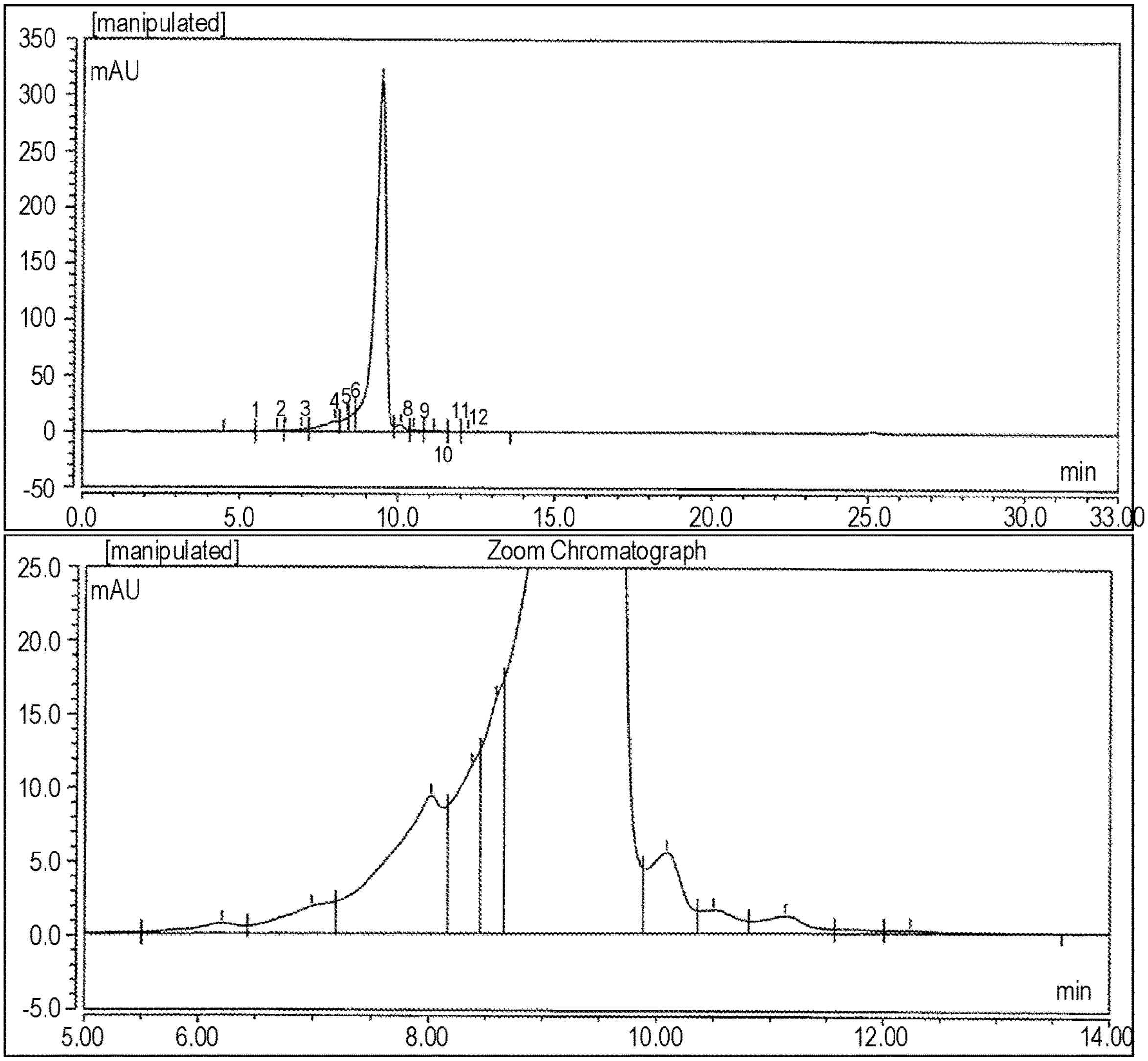

The purified drug substance solution was desalted and lyophilized to 1450.72 g purified Golodirsen drug substance. Yield 54.56%; HPLC: 93.531% (FIG. 5; C18) 88.354% (FIG. 6; SCX).

TABLE 5

| Acronyms | |
|---|---|
| Acronym | Name |
| DBU | 1,8-Diazabicycloundec-7-ene |
| DCM | Dichloromethane |
| DIPEA | N,N-Diisopropylethylamine |
| DMI | 1,3-Dimethyl-2-imidazolidinone |
| DTT | Dithiothreitol |
| IPA | Isopropyl alcohol |
| MW | Molecular weight |
| NEM | N-Ethylmorpholine |
| NMP | N-Methyl-2-pyrrolidone |
| RT | Room temperature |
| TFA | 2,2,2-Trifluoroacetic acid |
| TFE | 2,2,2-Trifluoroethanol |

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

EQUIVALENTS

Those skilled in the art will recognize, or be able to ascertain using no more than routine experimentation, many equivalents of the specific embodiments of the disclosure described herein. Such equivalents are intended to be encompassed by the following claims.

The invention claimed is:
1. A process for preparing an oligomeric compound of Formula (G):
(G)
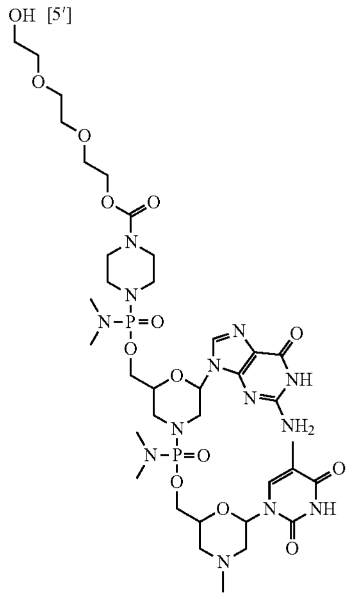
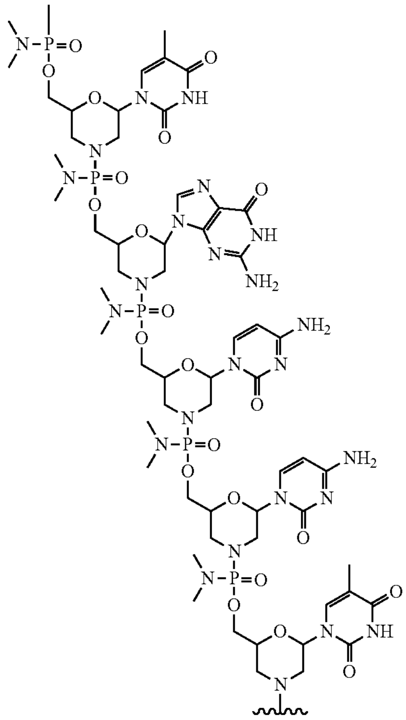
BREAK A
-continued
BREAK A
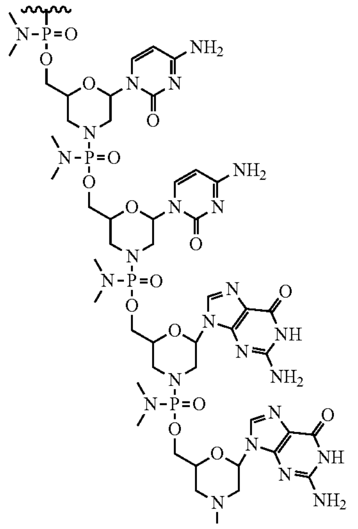
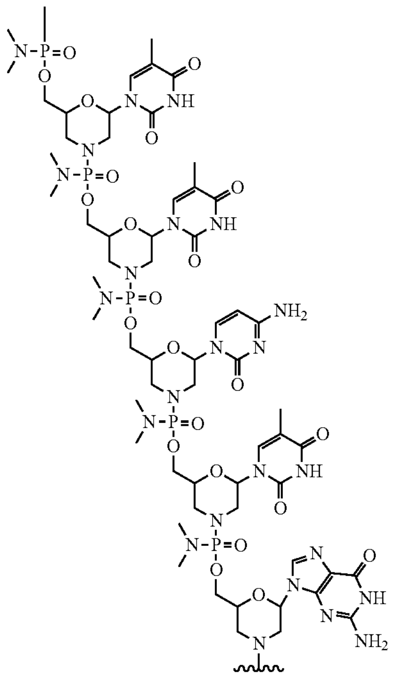
BREAK B

-continued
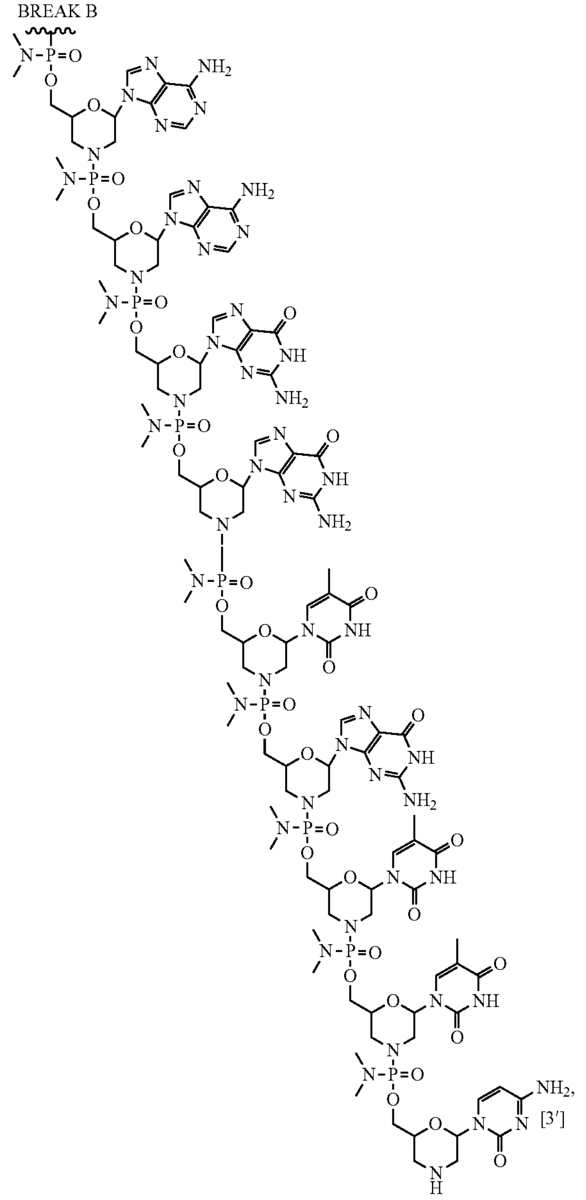 [SMILES: *P(=O)(OCC1CN(P(=O)(OCC2CN(P(=O)(OCC3CN(P(=O)(OCC4CN(P(=O)(OCC5CN(P(=O)(OCC6CN(P(=O)(OCC7CN(P(=O)(OCC8CN(P(=O)(OCC9CNCC(n%10ccc(N)nc%10=O)O9)N(C)C)CC(n9cc(C)c(=O)[nH]c9=O)O8)N(C)C)CC(n8cc(C)c(=O)[nH]c8=O)O7)N(C)C)CC(n7cnc8c(=O)[nH]c(N)nc87)O6)N(C)C)CC(n6cc(C)c(=O)[nH]c6=O)O5)N(C)C)CC(n5cnc6c(=O)[nH]c(N)nc65)O4)N(C)C)CC(n4cnc5c(=O)[nH]c(N)nc54)O3)N(C)C)CC(n3cnc4c(N)ncnc43)O2)N(C)C)CC(n2cnc3c(N)ncnc32)O1)N(C)C]
wherein the process comprises the sequential steps of: (a) contacting a compound of Formula (I):
(I)
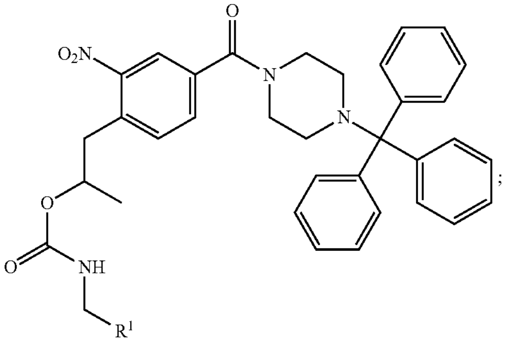
wherein $R^1$ is a support-medium,
with a deblocking agent to form the compound of Formula (II):
(II)
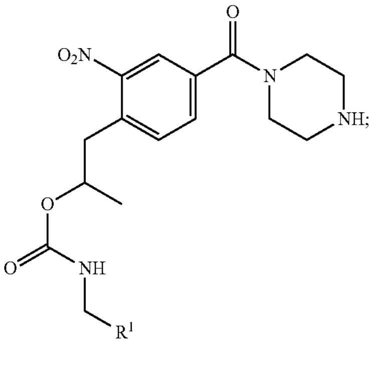
wherein $R^1$ is a support-medium;
(b) contacting the compound of Formula (II) with compound (B):
(B)
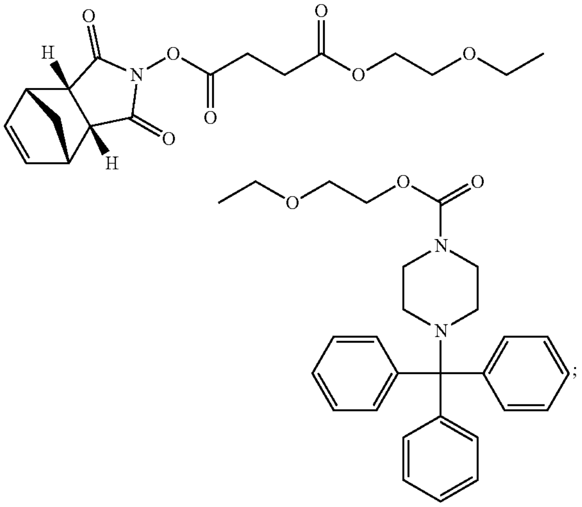
to form a compound of Formula (III):
(III)
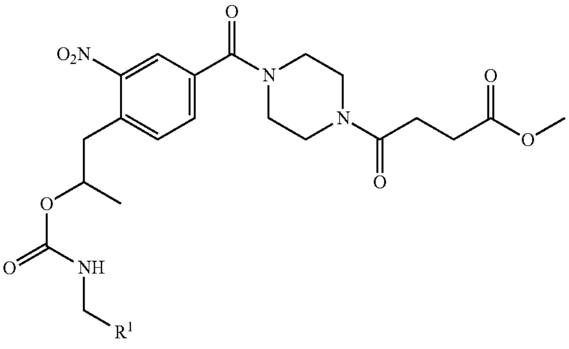

-continued

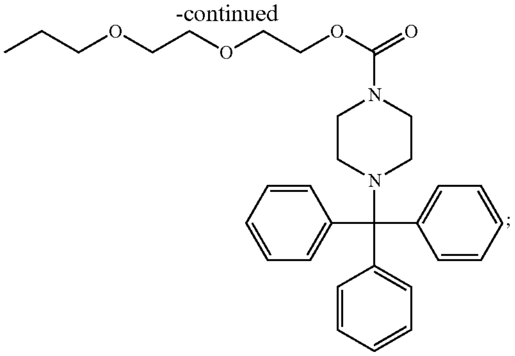

wherein $R^1$ is a support-medium;

(c) contacting the compound of Formula (III) with a deblocking agent to form a compound of Formula (IV):

(IV)

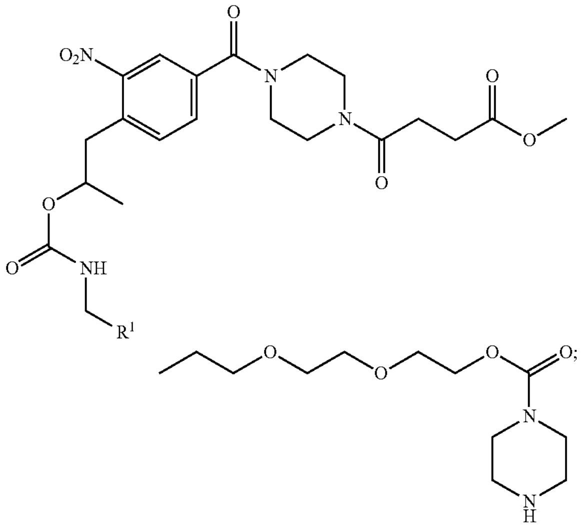

wherein $R^1$ is a support-medium;

(d) contacting the compound of Formula (IV) with a compound of Formula (DPG):

(DPG)

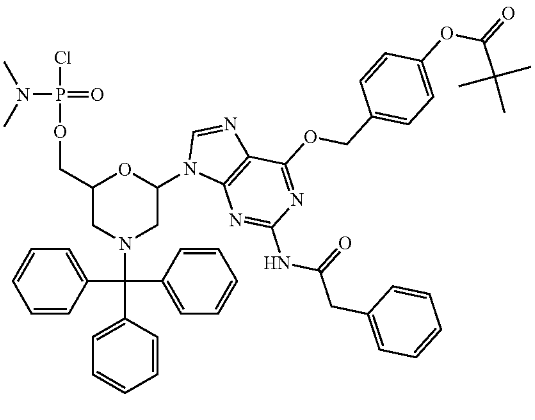

;

to form a compound of Formula (V):

(V)

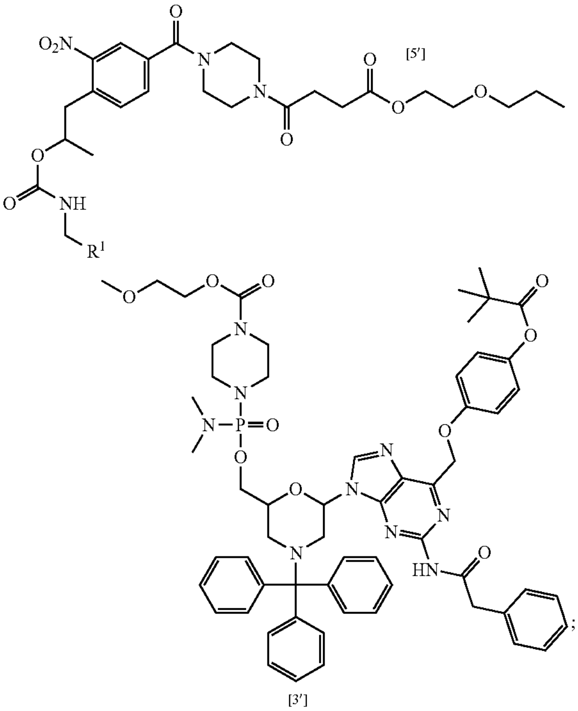

wherein $R^1$ is a support-medium;

(e) contacting the compound of Formula (V) with a deblocking agent to form a compound of Formula (VI):

(VI)

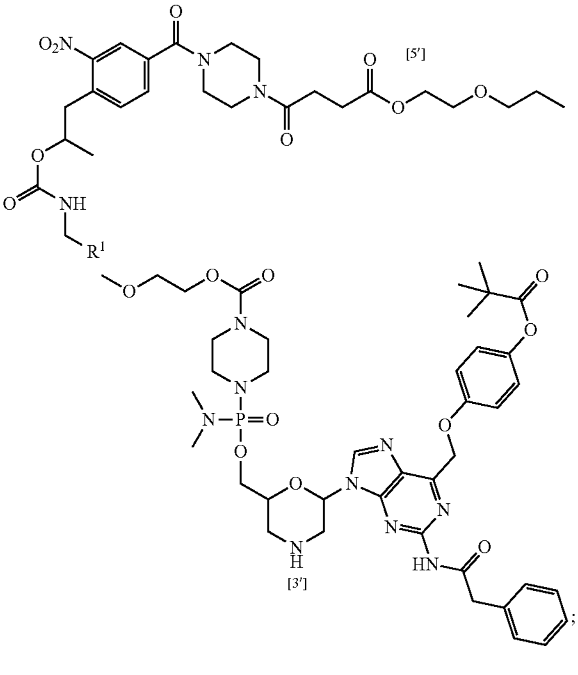

wherein $R^1$ is a support-medium;

(f) contacting the compound of Formula (VI) with compound of Formula (T):

(T)

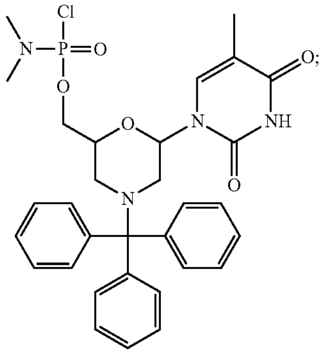

to form a compound of Formula (VII):

(VII)

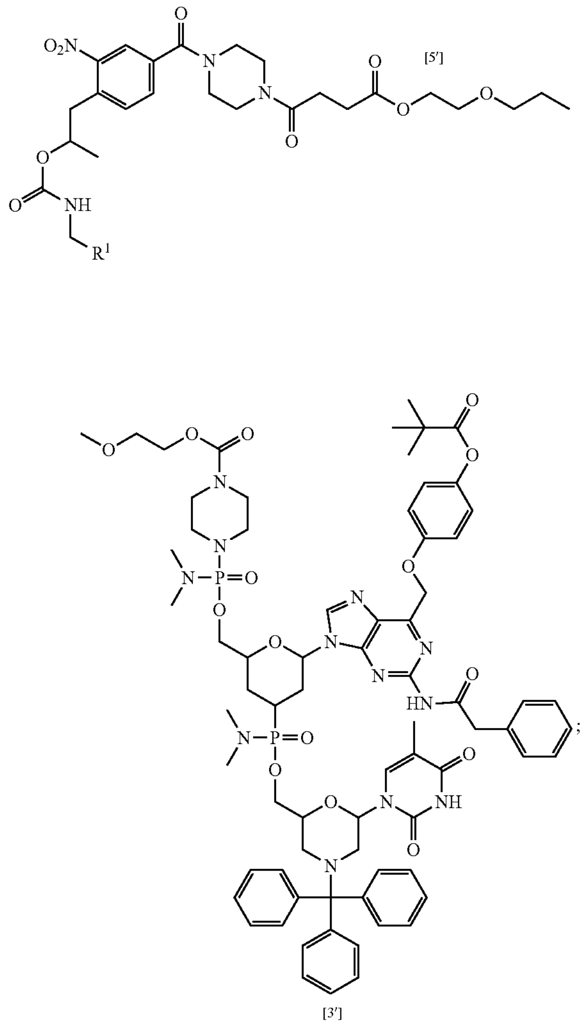

wherein $R^1$ is a support-medium;

(g) performing 23 iterations of the sequential steps of:

(g1) contacting the product formed by the immediately prior step with a deblocking agent; and (g2) contacting the compound formed by the immediately prior step with a compound of Formula (VIII):

(VIII)

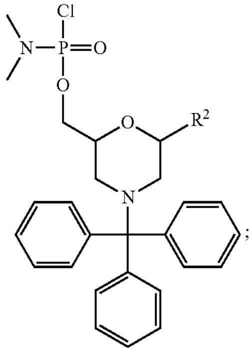

;

wherein $R^2$ is, independently for each compound of Formula (VIII), selected from the group consisting of:

(PC)

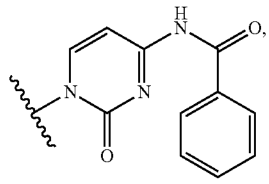

(DPG)

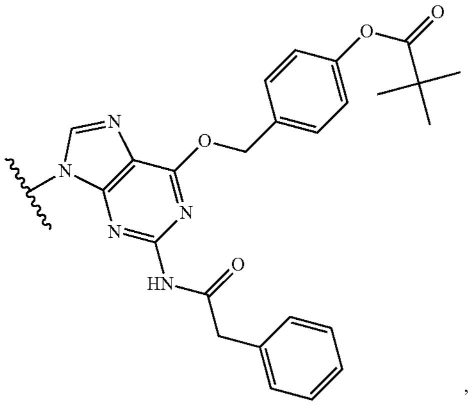

, (T)

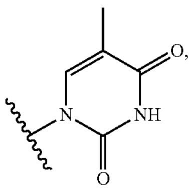

and (PA)

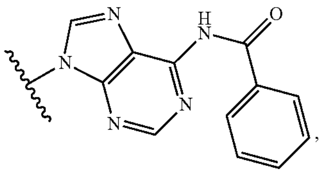

, wherein, for each iteration from 1 to 23, $R^2$ is:

| Iteration No. | $R^2$ |
|---|---|
| 1 | T |
| 2 | DPG |
| 3 | PC |
| 4 | PC |
| 5 | T |
| 6 | PC |
| 7 | PC |
| 8 | DPG |
| 9 | DPG |
| 10 | T |
| 11 | T |
| 12 | PC |
| 13 | T |
| 14 | DPG |
| 15 | PA |
| 16 | PA |
| 17 | DPG |
| 18 | DPG |
| 19 | T |
| 20 | DPG |
| 21 | T |
| 22 | T |
| 23 | PC |

to form a compound of Formula (IX):

(IX)

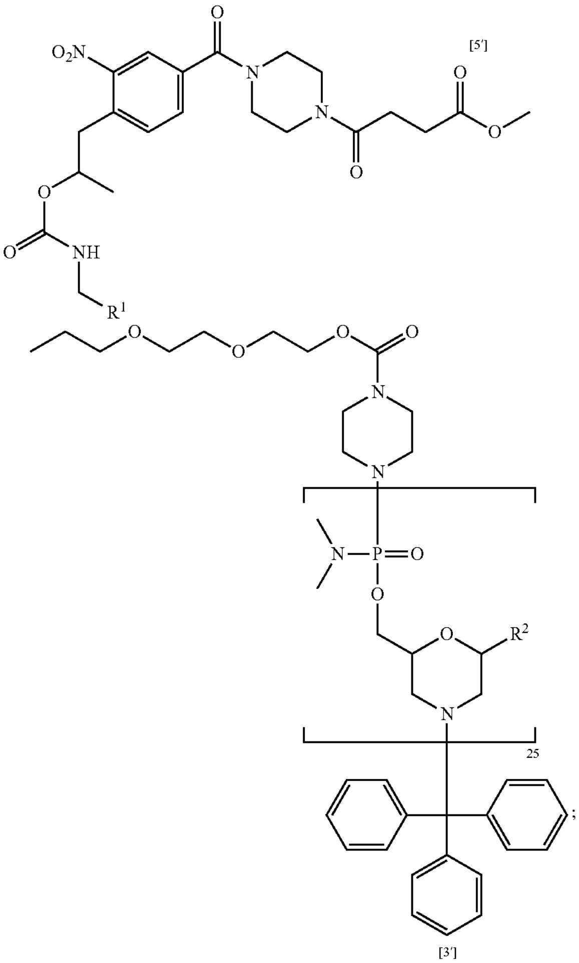

;

wherein $R^1$ is a support-medium, wherein $R^2$ is, independently for each occurrence, selected from the group consisting of:

(PC)

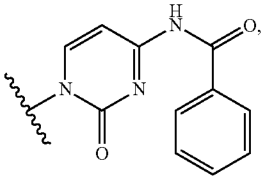

, (DPG)

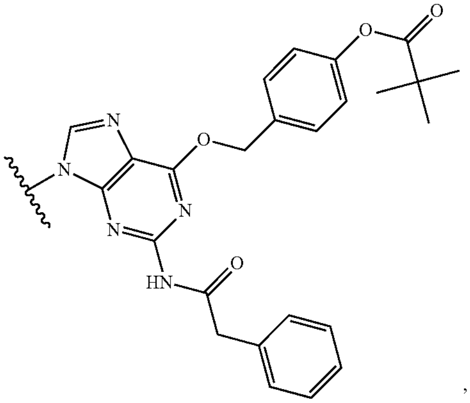

, (T)

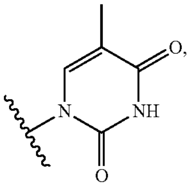

, and (PA)

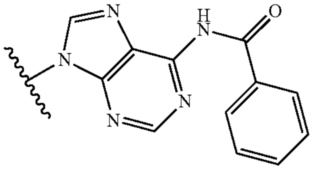

, and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |

-continued

| Position No. 5' to 3' | $R^2$ |
|---|---|
| 19 | DPG |
| 20 | DPG |
| 21 | T |
| 22 | DPG |
| 23 | T |
| 24 | T |
| 25 | PC |

(h) contacting the compound of Formula (IX) with a deblocking agent to form a compound of Formula (X):

(X)

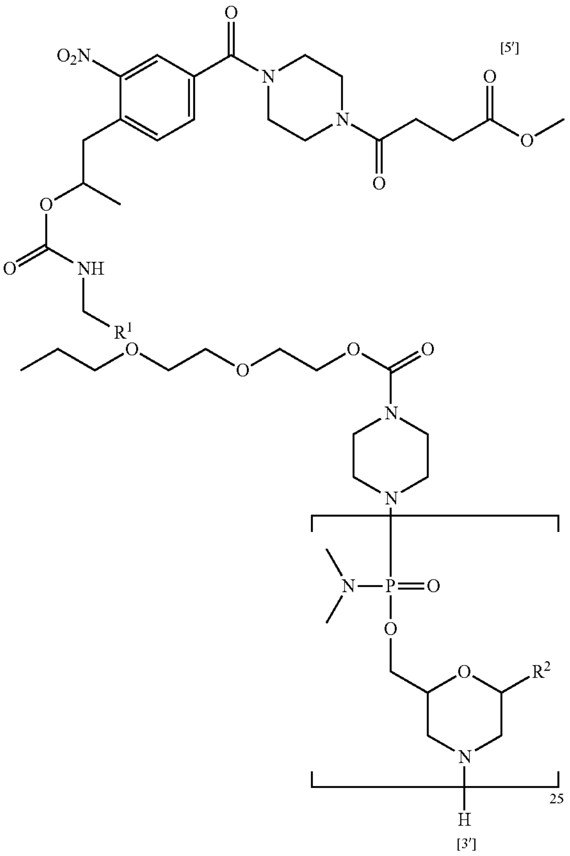

;

wherein $R^1$ is a support-medium, wherein $R^2$ is, independently for each occurrence, selected from the group consisting of:

(PC)

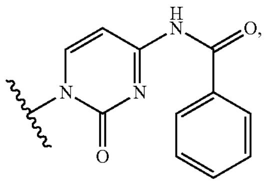

-continued (DPG)

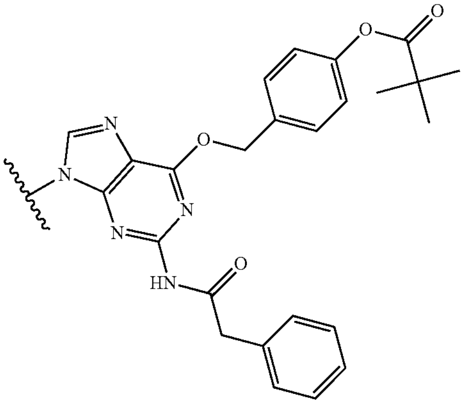

, (T)

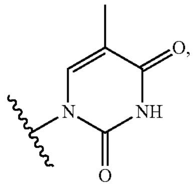

and (PA)

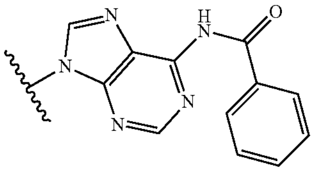

, and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

(i) contacting the compound of Formula (X) with a cleaving agent to form a compound of Formula (XI):

(XI)

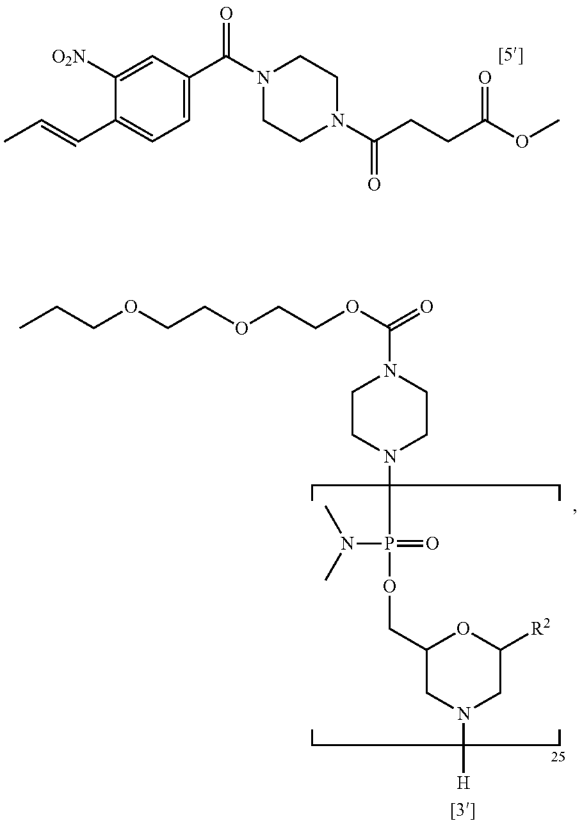

wherein $R^2$ is, independently for each occurrence, selected from the group consisting of:

(PC)

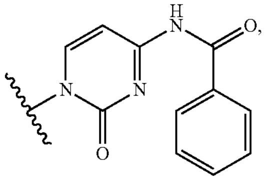

(DPG)

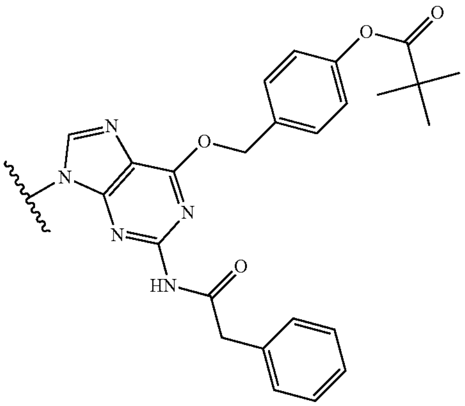

,

-continued (T)

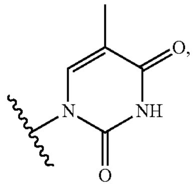

and (PA)

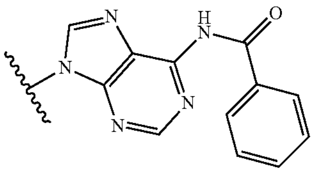

, and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC |

and (j) contacting the compound of Formula (XI) with a deprotecting agent to form the oligomeric compound of Formula (G).

2. The process of claim 1, wherein step (d), step (f) or step (g2) further comprises contacting the compound of Formula (IV), Formula (VI), or the compound formed by the immediately prior step, respectively, with a capping agent.

3. The process of claim 1, wherein the deblocking agent used in each step is cyanoacetic acid.

4. The process of claim 3, wherein the halogenated acid is selected from the group consisting of chloroacetic acid, dichloroacetic acid, trichloroacetic acid, fluoroacetic acid, difluoroacetic acid, and trifluoroacetic acid.

5. The process of claim 1, wherein the support-medium comprises a material selected from the group consisting of glass, modified or functionalized glass, plastics, polysaccharides, nylon or nitrocellulose, ceramics, resins, silica or silica-based materials, carbon, metals, and optical fiber bundles.

6. The process of claim 1, wherein the oligomeric compound of Formula (G) is an oligomeric compound of Formula (XII):
(XII)
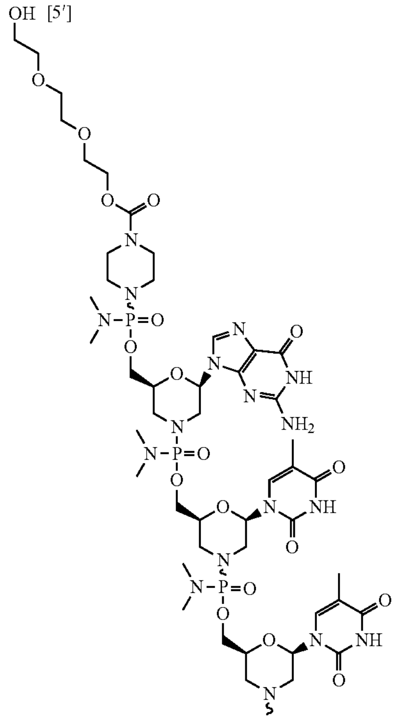
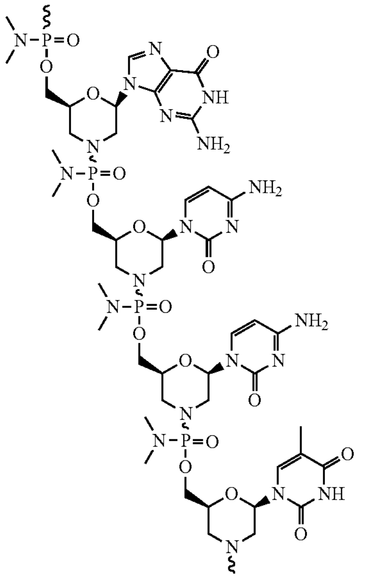
BREAK A
-continued
BREAK A
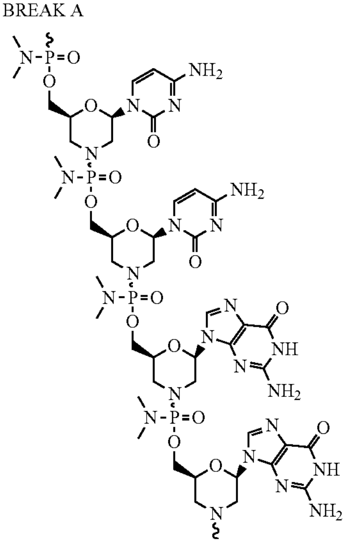
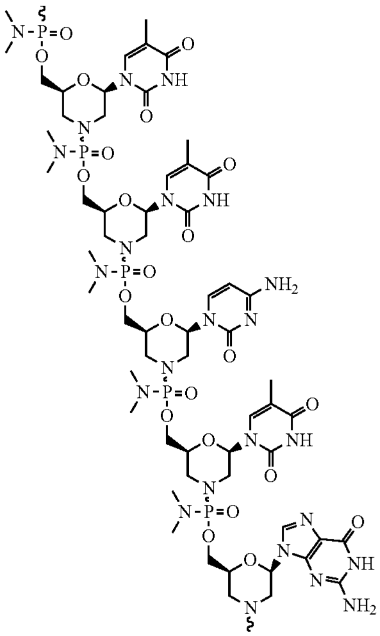
BREAK B -continued
BREAK B
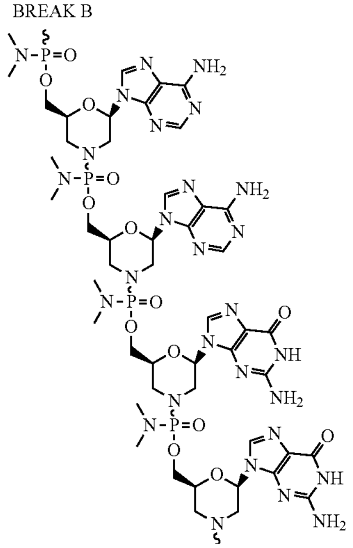
-continued
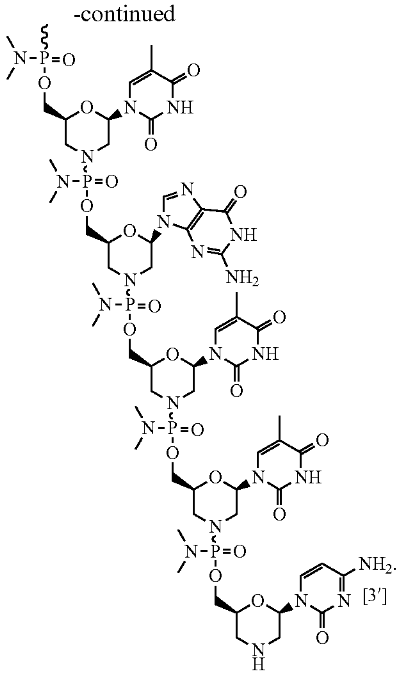
7. A compound of Formula (IX):
(IX)
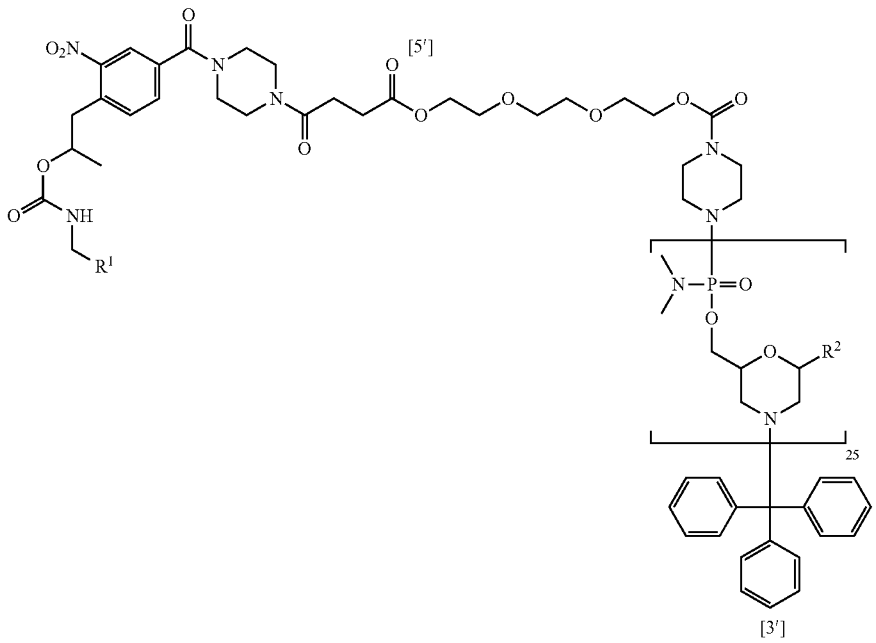
, or a pharmaceutically acceptable salt thereof, wherein:

$R^1$ is a support-medium, and $R^2$ is, independently at each occurrence, selected from the group consisting of:

(PC)

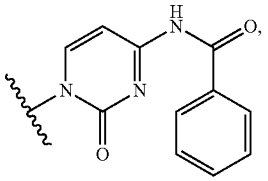

(DPG)

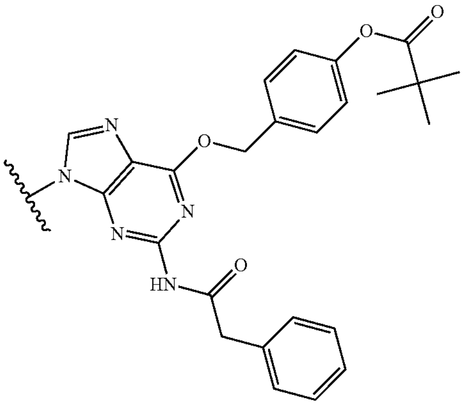

, (T)

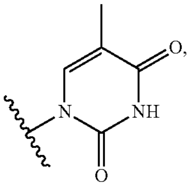

and

-continued (PA)

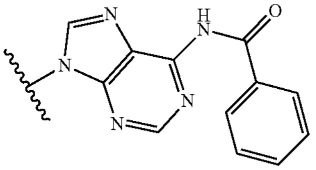

, and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC. |

8. The compound of claim 7, wherein the compound of Formula (IX) is of Formula (IXa):

(IXa)

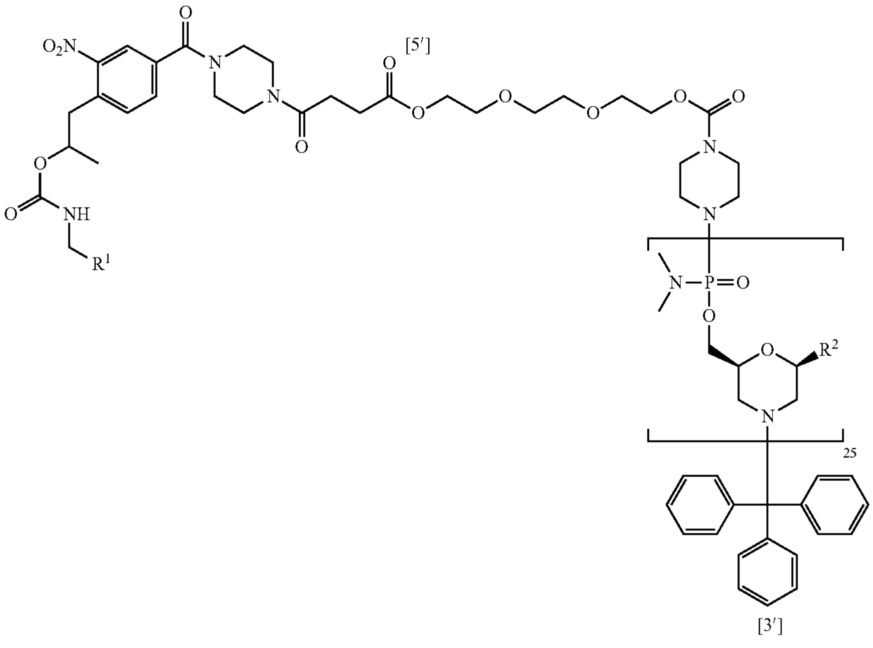

, or a pharmaceutically acceptable salt thereof, wherein $R^1$ is a support-medium, and $R^2$ is, independently at each occurrence, selected from the group consisting of:

(A)

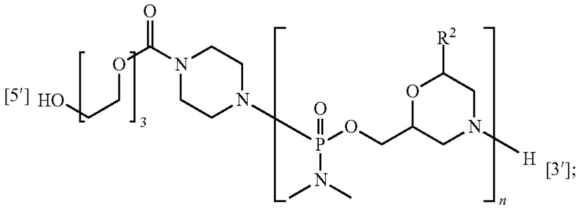

and wherein $R^2$ is at each position from 1 to 25 and 5' to 3':

| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC. |

9. The compound according to claim 7, wherein the support-medium comprises polystyrene with 1% crosslinked divinylbenzene.

10. A compound of Formula (XI):

(X)

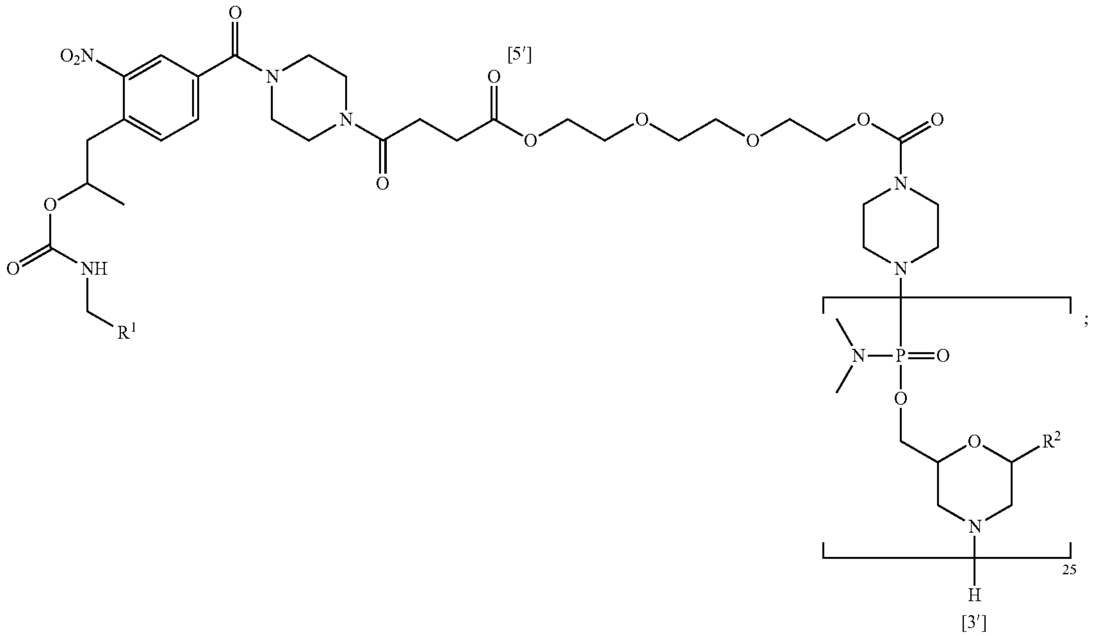

or a pharmaceutically acceptable salt thereof, wherein:
$R^2$ is, independently at each occurrence, selected from the group consisting of:
(PC)
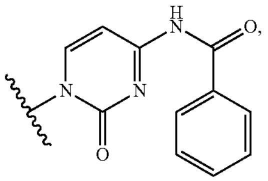
(DPG)
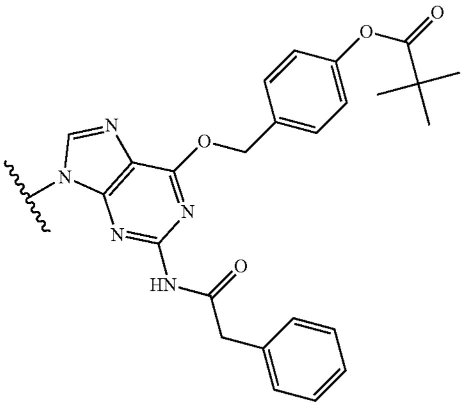
,
-continued
(T)
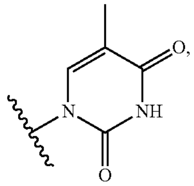
and
(PA)
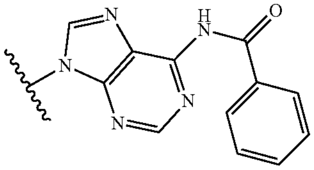
,
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC. |

11. The compound of claim 10, wherein the compound of Formula (XI) is of Formula (XIa):
(XIa)
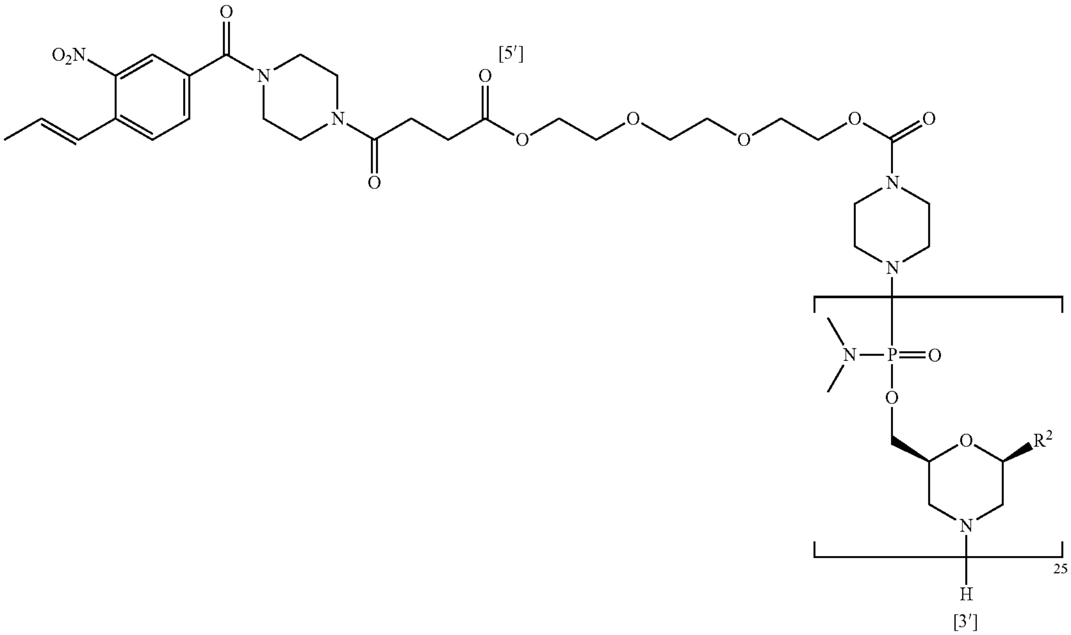
,
or a pharmaceutically acceptable salt thereof, wherein $R^2$ is, independently at each occurrence, selected from the group consisting of:
(PC)
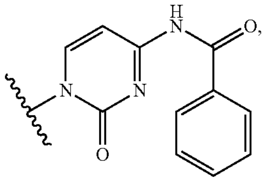
(DPG)
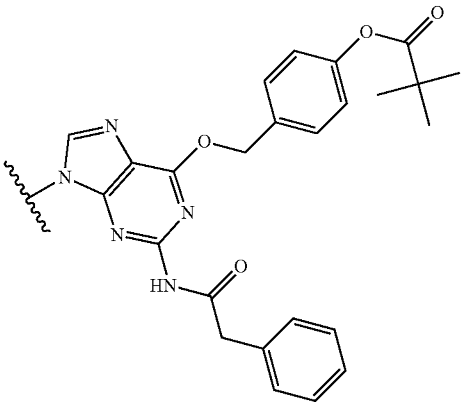
,
-continued
(T)
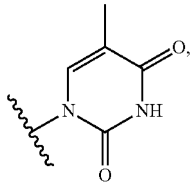
and
(PA)
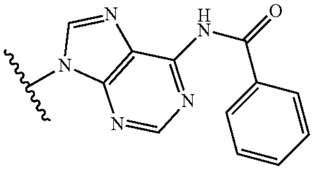
,
and
wherein $R^2$ is at each position from 1 to 25 and 5' to 3':
| Position No. 5' to 3' | $R^2$ |
|---|---|
| 1 | DPG |
| 2 | T |
| 3 | T |
| 4 | DPG |
| 5 | PC |
| 6 | PC |
| 7 | T |
| 8 | PC |
| 9 | PC |
| 10 | DPG |
| 11 | DPG |
| 12 | T |
| 13 | T |
| 14 | PC |

-continued

| Position No. 5' to 3' | $R^2$ |
|---|---|
| 15 | T |
| 16 | DPG |
| 17 | PA |
| 18 | PA |
| 19 | DPG |
| 20 | DPG |
| 21 | T |
| 22 | DPG |
| 23 | T |
| 24 | T |
| 25 | PC. |

12. The process of claim 5, wherein the support-medium comprises plastics selected from the group consisting of acrylics, polystyrene, copolymers of styrene and other materials, polypropylene, polyethylene, polybutylene, and polyurethanes.

13. The process of claim 5, wherein the support-medium comprises polystyrene with 1% crosslinked divinylbenzene.

* * * * *

UNITED STATES PATENT AND TRADEMARK OFFICE

CERTIFICATE OF CORRECTION

PATENT NO. : 11,472,824 B2
APPLICATION NO. : 16/302529
DATED : October 18, 2022
INVENTOR(S) : Cai et al.

It is certified that error appears in the above-identified patent and that said Letters Patent is hereby corrected as shown below:

In the Claims

In Column 212, Claim 10, Line 28, delete:

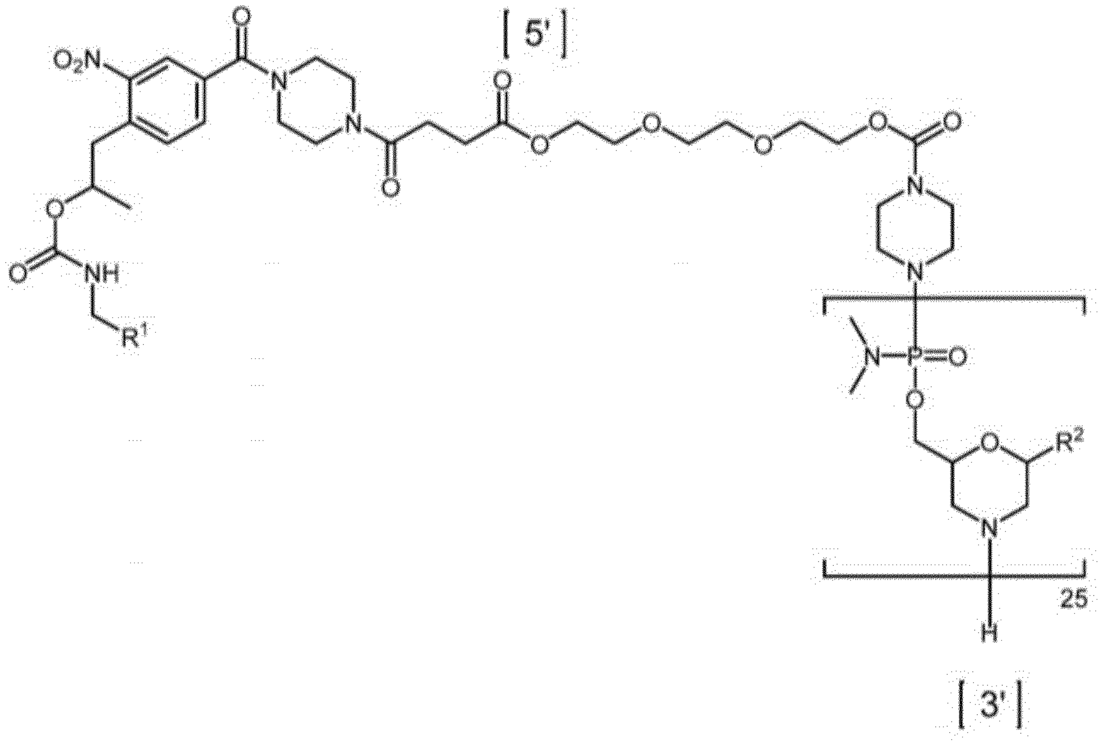

“ (X) ”

Signed and Sealed this
Seventeenth Day of December, 2024

Derrick Brent
*Acting Director of the United States Patent and Trademark Office*

And insert:
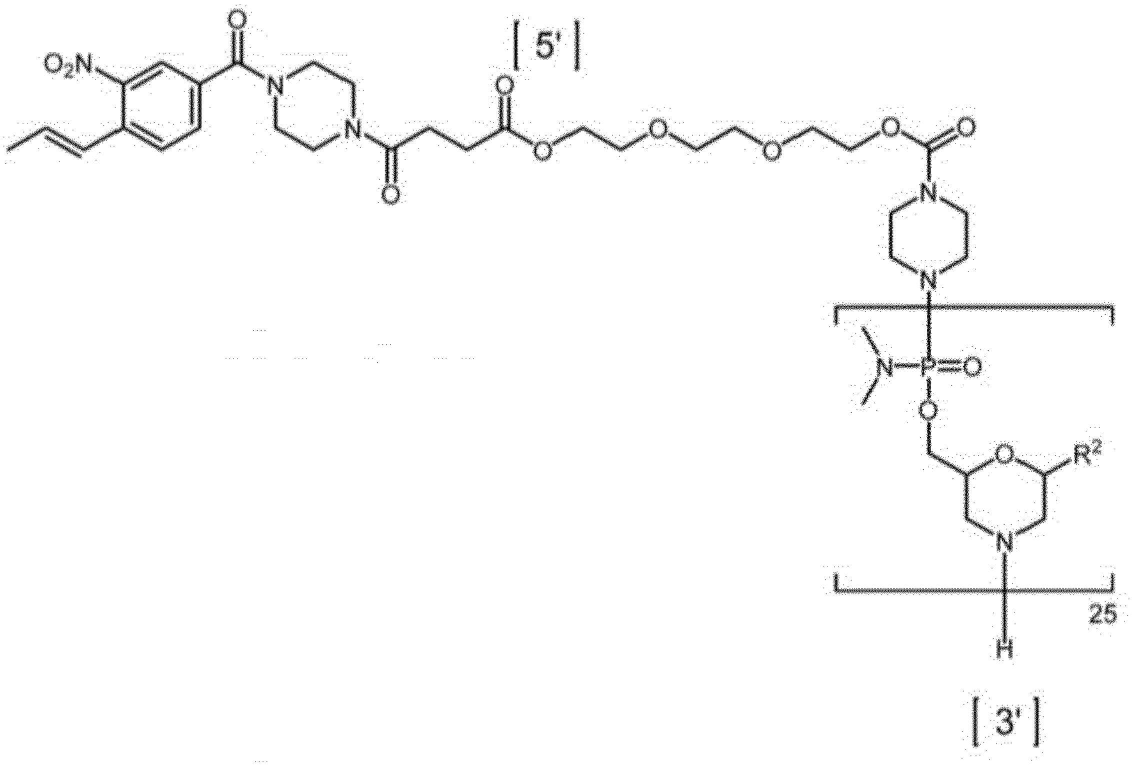
(XI)
-- --

SEQUENCE LISTING

<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: GOLODIRSEN PMO SPR-4053

<400> SEQUENCE: 1
gttgcctccg gttctgaagg tgttc 25